(12) United States Patent
Hoffman et al.

(10) Patent No.: US 10,640,497 B2
(45) Date of Patent: May 5, 2020

(54) MICROBIOCIDAL OXADIAZOLE DERIVATIVES

(71) Applicant: SYNGENTA PARTICIPATIONS AG, Basel (CH)

(72) Inventors: Thomas James Hoffman, Stein (CH); Daniel Stierli, Stein (CH); Martin Pouliot, Stein (CH); Renaud Beaudegnies, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/780,007

(22) PCT Filed: Nov. 30, 2016

(86) PCT No.: PCT/EP2016/079329
§ 371 (c)(1),
(2) Date: May 30, 2018

(87) PCT Pub. No.: WO2017/093348
PCT Pub. Date: Jun. 8, 2017

(65) Prior Publication Data
US 2018/0362515 A1 Dec. 20, 2018

(30) Foreign Application Priority Data

| Dec. 2, 2015 | (EP) | 15197571 |
| Dec. 22, 2015 | (EP) | 15202192 |
| Feb. 26, 2016 | (EP) | 16157729 |

(51) Int. Cl.
| A01N 43/82 | (2006.01) |
| C07D 413/10 | (2006.01) |
| C07D 413/14 | (2006.01) |
| C07D 417/10 | (2006.01) |
| C07D 471/08 | (2006.01) |

(52) U.S. Cl.
CPC .......... *C07D 413/10* (2013.01); *A01N 43/82* (2013.01); *C07D 413/14* (2013.01); *C07D 417/10* (2013.01); *C07D 471/08* (2013.01)

(58) Field of Classification Search
CPC .. C07D 413/10; C07D 413/14; C07D 417/10; C07D 471/08; A01N 43/82
See application file for complete search history.

(56) References Cited

U.S. PATENT DOCUMENTS

| 4,871,753 | A | 10/1989 | Rohr | |
| 5,977,373 | A * | 11/1999 | Gadwood | C07D 417/10 548/128 |
| 2010/0048563 | A1* | 2/2010 | Kesteleyn | C07D 471/04 514/234.5 |
| 2018/0265483 | A1* | 9/2018 | Stierli | A01N 43/82 |
| 2018/0273494 | A1* | 9/2018 | Stierli | C07D 413/04 |
| 2018/0319753 | A1* | 11/2018 | Hoffman | A01N 43/82 |
| 2018/0362515 | A1* | 12/2018 | Hoffman | C07D 413/10 |
| 2018/0368409 | A1* | 12/2018 | Kretschmer | A01N 43/82 |
| 2018/0368410 | A1* | 12/2018 | Hoffman | A01N 43/82 |
| 2018/0370927 | A1* | 12/2018 | Hoffman | A01N 43/82 |

FOREIGN PATENT DOCUMENTS

| CN | 1927860 | A | 3/2007 | |
| EP | 0276432 | A2 | 8/1988 | |
| EP | 2016/079329 | A1 | 5/2017 | |
| EP | 3165093 | A1 | 5/2017 | |
| EP | 3165094 | A1 | 5/2017 | |
| EP | 3187497 | A1 | 7/2017 | |
| JP | 2015253228 | | * 12/2015 | ............. A01N 25/04 |
| JP | 2016190828 | | * 9/2016 | ............. A01N 25/04 |
| JP | 2017190296 | A | 10/2017 | |
| WO | 2008037789 | A1 | 4/2008 | |
| WO | 2011088181 | A1 | 7/2011 | |
| WO | 2011088192 | A1 | 7/2011 | |
| WO | 2011101402 | A1 | 8/2011 | |
| WO | 2012052490 | A1 | 4/2012 | |
| WO | 2013006408 | A1 | 1/2013 | |
| WO | 2013008162 | A1 | 1/2013 | |
| WO | 2013009810 | A1 | 1/2013 | |
| WO | 2013009827 | A1 | 1/2013 | |
| WO | 2013009830 | A1 | 1/2013 | |
| WO | 2013064079 | A1 | 5/2013 | |

(Continued)

OTHER PUBLICATIONS

JP 2015253228 Priority Application English Google Translation (2015) (Year: 2015).*
JP 2016190828 Priority Application English Google Translation (2016) (Year: 2016).*
WO 2017/110862 English-Language Machine Translation (2017) (Year: 2017).*
CAS Abstract and Indexed Compounds WO 2017/110862 (2017) (Year: 2017).*
International Search Report and Written Opinion for PCT/EP2016/079329, dated Jan. 18, 2017.

*Primary Examiner* — Alexander R Pagano
(74) *Attorney, Agent, or Firm* — Baker & Hostetler, LLP; Toni-Junell Herbert

(57) ABSTRACT

Compounds of the formula (I), wherein the substituents are as defined in claim 1, useful as a pesticides, especially as fungicides.

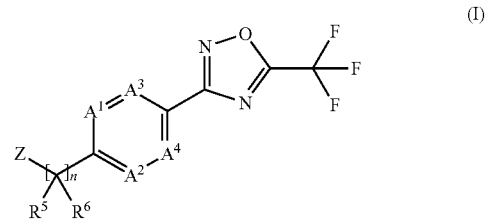

18 Claims, No Drawings

(56) References Cited

FOREIGN PATENT DOCUMENTS

| | | |
|---|---|---|
| WO | 2013066835 A2 | 5/2013 |
| WO | 2013066839 A2 | 5/2013 |
| WO | 2013080120 A1 | 6/2013 |
| WO | 2013/156559 A1 | 10/2013 |
| WO | 2015055706 A2 | 4/2015 |
| WO | 2015185485 A1 | 12/2015 |
| WO | 2017033946 A1 | 3/2017 |
| WO | 2017076739 A1 | 5/2017 |
| WO | 2017076740 A1 | 5/2017 |
| WO | 2017076742 A1 | 5/2017 |
| WO | 2017076757 A1 | 5/2017 |
| WO | 2017076935 A1 | 5/2017 |
| WO | 2017081309 A1 | 5/2017 |
| WO | 2017081310 A1 | 5/2017 |
| WO | 2017081311 A1 | 5/2017 |
| WO | 2017081312 A1 | 5/2017 |
| WO | 2017085098 A1 | 5/2017 |
| WO | WO-2017085100 A1 * | 5/2017 | ............ A01N 43/82 |
| WO | 2017093019 A1 | 6/2017 |
| WO | 2017110861 A1 | 6/2017 |
| WO | 2017110862 A1 | 6/2017 |
| WO | 2017110864 A1 | 6/2017 |
| WO | 2017110865 A1 | 6/2017 |
| WO | 2017111152 A1 | 6/2017 |
| WO | WO-2017110862 A1 * | 6/2017 | ............ A01N 25/04 |
| WO | WO-2017111152 A1 * | 6/2017 | ............ A01N 47/40 |
| WO | WO-2017148797 A1 * | 9/2017 | ............ A01N 43/82 |
| WO | 2017169893 A1 | 10/2017 |
| WO | 2017178245 A1 | 10/2017 |
| WO | WO-2017178245 A1 * | 10/2017 | ............ A01N 43/82 |
| WO | 2017211649 A1 | 12/2017 |
| WO | 2017211650 A1 | 12/2017 |
| WO | 2017211652 A1 | 12/2017 |
| WO | 2017213252 A1 | 12/2017 |
| WO | 2017222951 A1 | 12/2017 |
| WO | 2018030460 A1 | 2/2018 |

* cited by examiner

MICROBIOCIDAL OXADIAZOLE DERIVATIVES

CROSS-REFERENCE TO RELATED APPLICATIONS

This application is a 371 National Stage application of International Application No. PCT/EP2016/079329, filed Nov. 30, 2016, which claims priority to European Patent Application No. 15197571.1, filed Dec. 2, 2015, European Patent Application No. 15202192.9, filed Dec. 22, 2015, and European Patent Application No. 16157729.1, filed Feb. 26, 2016, the entire contents of which applications are hereby incorporated by reference.

The present invention relates to microbiocidal oxadiazole derivatives, eg, as active ingredients, which have microbiocidal activity, in particular, fungicidal activity. The invention also relates to agrochemical compositions which comprise at least one of the oxadiazole derivatives, to processes of preparation of these compounds and to uses of the oxadiazole derivatives or compositions in agriculture or horticulture for controlling or preventing infestation of plants, harvested food crops, seeds or non-living materials by phytopathogenic microorganisms, preferably fungi.

According to the present invention, there is provided a compound of formula (I):

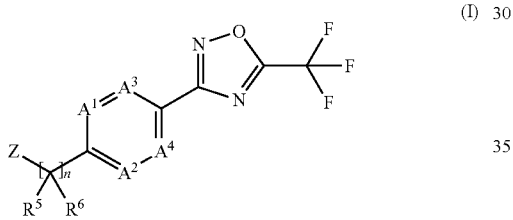

wherein n is 0 or 1 or 2;

$A^1$ represents N or $CR^1$, wherein $R^1$ represents hydrogen, halogen, methyl, ethyl, difluoromethyl, trifluoromethyl, methoxy, ethoxy, or difluoromethoxy;

$A^2$ represents N or $CR^2$, wherein $R^2$ represents hydrogen, halogen, methyl, ethyl, difluoromethyl, trifluoromethyl, methoxy, ethoxy, or difluoromethoxy;

$A^3$ represents N or $CR^3$, wherein $R^3$ represents hydrogen or halogen;

$A^4$ represents N or $CR^4$, wherein $R^4$ represents hydrogen or halogen; and wherein no more than two of $A^1$ to $A^4$ are N;

$R^5$ and $R^6$ independently represent hydrogen, halogen, cyano, difluoromethyl, trifluoromethyl, or $C_{1-4}$alkyl, or together with the carbon atom to which they are bonded represent cyclopropyl;

Z represents a group selected from Z-1, Z-2, Z-3 or Z-4:

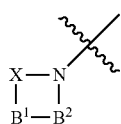

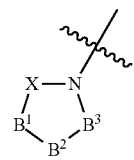

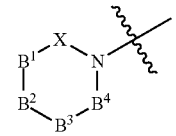

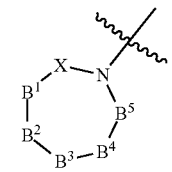

wherein:

X represents C(O) or $S(O)_2$; and (i) $B^1$ and $B^2$ in Z-1 represent $C(R^7)(R^8)$; or (ii) $B^1$, $B^2$ and $B^3$ in Z-2 independently represent $C(R^7)(R^8)$, O, S, $NR^9$ or C(=O), wherein only one of $B^1$, $B^2$ and $B^3$ may be a group selected from O, S, $NR^9$ or C(=O); or (iii) $B^1$, $B^2$, $B^3$ and $B^4$ in Z-3 independently represent $C(R^7)(R^8)$, O, S, $NR^9$ or C(=O), wherein only one of $B^1$, $B^2$, $B^3$ and $B^4$ may be a group selected from O, S or C(=O), and only one of $B^1$, $B^2$, $B^3$ and $B^4$ may be $NR^9$; or (iv) $B^1$ in Z-2 is $C(R^7)(R^8)$ and $B^2$—$B^3$ is a group selected from $NR^9C$(=O), C(=O)$NR^9$, N=N, $C(R^7)$=$C(R^8)$, C(R')=N or N=$C(R^8)$; or $B^3$ in Z-2 is $C(R^7)(R^8)$ and $B^1$—$B^2$ is a group selected from $NR^9C$(=O), C(=O)$NR^9$, N=N, $C(R^7)$=$C(R^8)$, C(R')=N or N=$C(R^8)$; or (v) $B^1$ and $B^2$ in Z-3 are $C(R^7)(R^8)$ and $B^3$—$B^4$ is a group selected from $NR^9C$(=O), C(=O)$NR^9$, N=N, $C(R^7)$=$C(R^8)$, C(R')=N or N=$C(R^8)$; $B^1$ and $B^4$ in Z-3 are $C(R^7)(R^8)$ and $B^2$—$B^3$ is a group selected from $NR^9C$(=O), C(=O)$NR^9$, N=N, $C(R^7)$=$C(R^8)$, $C(R^8)$=N or N=$C(R^8)$; or $B^3$ and $B^4$ in Z-3 are $C(R^7)(R^8)$ and $B^1$—$B^2$ is a group selected from $NR^9C$(=O), C(=O)$NR^9$, N=N, $C(R^7)$=$C(R^8)$, C(R')=N or N=$C(R^8)$; or (vi) $B^1$, $B^2$, $B^3$, $B^4$ and $B^5$ in Z-4 independently represent $C(R^7)(R^8)$, O, S, $NR^9$ or C(=O), wherein only one of $B^1$, $B^2$, $B^3$, $B^4$ and $B^5$ may be a group selected from O, S, $NR^9$ or C(=O); or Z represents a group selected from Z-5, wherein Z-5 represents Z-5a, Z-5b, Z-5c, Z-5d, Z-5e, Z-5f or Z-5g:

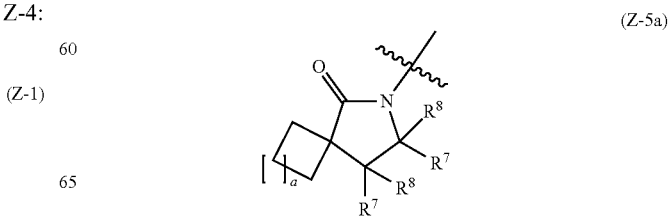

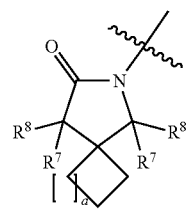

(Z-5b)

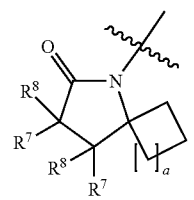

(Z-5c)

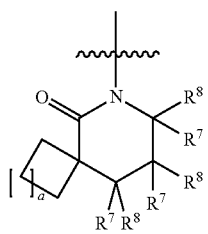

(Z-5d)

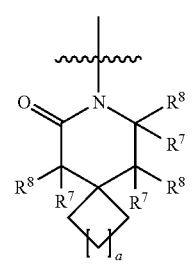

(Z-5e)

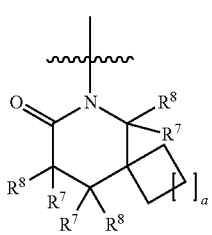

(Z-5f)

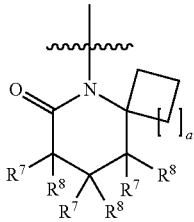

(Z-5g)

wherein a is 0, 1, 2 or 3; or

Z represents a group selected from Z-6, wherein Z-6 represents Z-6a, Z-6b, Z-6c or Z-6d:

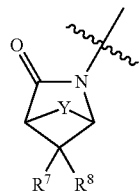

(Z-6a)

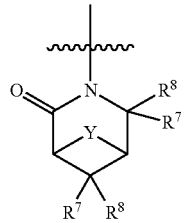

(Z-6b)

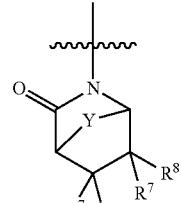

(Z-6c)

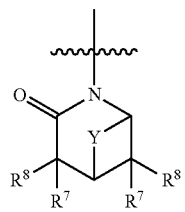

(Z-6d)

wherein Y is $C_{1-4}$alkylene or $C(R^7)=C(R^8)$;

$R^7$ and $R^8$ independently represent hydrogen, halogen, $C_1$-$C_4$alkyl, $C_1$-$C_4$haloalkyl or $C_1$-$C_4$alkoxy;

$R^9$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^{10}$, $C(O)OR^{10}$, $C(O)N(R^{10})R^{11}$, $S(O)_2R^{10}$ or $S(O)_2N(R^{10})R^{11}$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano;

$R^{10}$ represents hydrogen, $C_{1-6}$alkyl, $C_{3-6}$cycloalkyl, $C_{3-6}$cycloalkyl$C_{1-2}$alkyl, $C_{1-4}$alkoxy$C_{1-4}$alkyl, wherein $C_{1-6}$alkyl, $C_{3-6}$cycloalkyl, $C_{3-6}$cycloalkyl$C_{1-2}$alkyl and $C_{1-4}$alkoxy$C_{1-4}$alkyl are optionally substituted by halogen or cyano; and $R^{11}$ represents hydrogen, $C_{1-4}$alkyl, $C_{1-4}$haloalkyl, $C_{1-4}$alkoxy or $C_{1-4}$alkoxy-$C_{1-4}$alkyl; or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I).

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

As used herein, the term "halogen" or "halo" refers to fluorine, chlorine, bromine or iodine, preferably fluorine, chlorine or bromine.

As used herein, cyano means a —CN group.

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_{1-4}$alkyl" and "$C_{1-2}$alkyl" are to be construed accordingly. Examples of $C_{1-6}$alkyl include, but are not limited to, methyl, ethyl, n-propyl, 1-methylethyl (iso-propyl), n-butyl, 1-dimethylethyl (t-butyl) and n-pentyl. A "$C_{1-4}$alkylene" group refers to a corresponding definition of $C_1$-$C_4$alkyl, except that such radical is attached to the rest of the molecule by two single bonds. The term "$C_{2-4}$alkylene" is to be construed accordingly. Examples of $C_1$-$C_4$alkylene, include, but are not limited to, —$CH_2$—, —$CH_2CH_2$— and —$(CH_2)_3$—.

As used herein, the term "$C_{3-6}$alkenyl" refers to a straight or branched hydrocarbon chain radical group consisting solely of carbon and hydrogen atoms, containing at least one double bond that can be of either the (E)- or (Z)-configuration, having from three to six carbon atoms, which is attached to the rest of the molecule by a single bond. Examples of $C_{3-6}$alkenyl include, but are not limited to, prop-1-enyl, but-1-enyl.

As used herein, the term "$C_{3-6}$alkynyl" refers to a straight or branched hydrocarbon chain radical group consisting solely of carbon and hydrogen atoms, containing at least one triple bond, having from three to six carbon atoms, and which is attached to the rest of the molecule by a single bond.

Examples of $C_{3-6}$alkynyl include, but are not limited to, prop-1-ynyl, but-1-ynyl.

As used herein, the term "$C_{1-6}$alkoxy" refers to a radical of the formula —$OR_a$ where $R_a$ is a $C_{1-6}$ alkyl radical as generally defined above. The term "$C_1$-$C_4$ alkoxy" is to be construed accordingly. Examples of $C_{1-6}$alkoxy include, but are not limited to, methoxy, ethoxy, propoxy, iso-propoxy, butoxy.

As used herein, the term "$C_{1-4}$haloalkyl" refers to a $C_{1-4}$alkyl radical as generally defined above substituted by one or more of the same or different halogen atoms. Examples of $C_{1-4}$haloalkyl include, but are not limited to fluoromethyl, difluoromethyl, fluoroethyl, trifluoromethyl, 2,2,2-trifluoroethyl.

As used herein, the term "$C_{3-6}$cycloalkyl" refers to a monocyclic radical and contains 3 to 6 carbon atoms. Examples of $C_{3-6}$cycloalkyl include, but are not limited to, cyclopropyl, 1-methylcyclopropyl, 2-methylcyclopropyl, cyclobutyl, cyclopentyl and cyclohexyl.

As used herein, the term "$C_{3-6}$cycloalkyl$C_{1-2}$alkyl" refers to a $C_{3-6}$cycloalkyl ring as defined above attached to the rest of the molecule by a $C_{1-2}$alkylene radical as defined above. Examples of $C_{3-6}$cycloalkyl$C_{1-2}$alkyl include, but are not limited to cyclopropylmethyl, cyclopropylethyl, cyclobutylmethyl, cyclopentylmethyl and cyclohexylmethyl.

As used herein, the term "$C_{1-4}$alkoxy$C_{1-4}$alkyl" refers to a $C_{1-4}$alkyl radical as generally defined above substituted by a $C_{1-4}$alkoxy group as defined above. Examples of $C_{1-4}$alkoxy$C_{1-4}$alkyl include, but are not limited to methoxymethyl, 2-methoxyethyl.

The presence of one or more possible asymmetric carbon atoms in a compound of formula (I) means that the compounds may occur in chiral isomeric forms, i.e., enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers (including lactam-lactim tautomerism and keto-enol tautomerism) where present. The present invention includes all possible tautomeric forms for a compound of formula (I).

In each case, the compounds of formula (I) according to the invention are in free form, in covalently hydrated form, in oxidized form as an N-oxide or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents n, X, $A^1$, $A^2$, $A^3$, $A^4$, $R^1$, $R^2$, $R^3$, $R^4$, $R^5$, $R^6$, Z (including Z-1, Z-2, Z-3, Z-4, Z-5 (Z-5a to Z-5g) and Z-6 (Z-6a to Z-6d)), $R^7$, $R^8$, $R^9$, $R^{10}$, $R^{11}$, a and Y with reference to the compounds of formula (I). For any one of these substituents, any of the definitions given below may be combined with any definition of any other substituent given below or elsewhere in this document.

n is 0 or 1 or 2. In one embodiment of the invention, n is 1. In another embodiment of the invention, n is 0. In a further embodiment of the invention, n is 2.

X represents C(O) or $S(O)_2$. In one embodiment of the invention, X is C(O). In another embodiment of the invention, X is $S(O)_2$.

$A^1$ represents N or $CR^1$, wherein $R^1$ represents hydrogen, halogen, methyl, ethyl, difluoromethyl, trifluoromethyl, methoxy, ethoxy, or difluoromethoxy. In one embodiment of the invention, $A^1$ is $CR^1$. Preferably, $R^1$ represents hydrogen, halogen, methyl, trifluoromethyl or methoxy. More preferably, $R^1$ represents hydrogen, halogen or methyl. Even more preferably, $R^1$ represents hydrogen or fluoro. Most preferably, $R^1$ represents hydrogen. In another embodiment of the invention, $A^1$ is N.

$A^2$ represents N or $CR^2$, wherein $R^2$ represents hydrogen, halogen, methyl, ethyl, difluoromethyl, trifluoromethyl, methoxy, ethoxy, or difluoromethoxy. In one embodiment of the invention, $A^2$ is $CR^2$. Preferably, $R^2$ represents hydrogen, halogen, methyl, trifluoromethyl or methoxy. More preferably, $R^2$ represents hydrogen or methyl. In another embodiment of the invention, $A^2$ is N.

$A^3$ represents N or $CR^3$, wherein $R^3$ represents hydrogen or halogen. In one embodiment of the invention, $A^3$ represents $CR^3$. Preferably, $R^3$ represents hydrogen.

$A^4$ represents N or $CR^4$, wherein $R^4$ represents hydrogen or halogen. In one embodiment of the invention, $A^4$ represents $CR^4$. Preferably, $R^4$ represents hydrogen.

In the compounds of Formula (I) according to the invention, no more than two of $A^1$ to $A^4$ are N, in particular, at least two of $R^1$ to $R^4$ may be hydrogen. Preferably, at least $R^2$, $R^3$ and $R^4$ are hydrogen. In other embodiments, (i)$^4$ is $CR^1$ and $R^1$ is hydrogen, and $A^2$ is $CR^2$ and $R^2$ is hydrogen; (ii)$^4$ is $CR^1$ and $R^1$ is halogen, and $A^2$ is $CR^2$ and $R^2$ is hydrogen; or (iii) $A^1$ is N and $A^2$ is $CR^2$ and $R^2$ is hydrogen. Preferably, $A^3$ is $CR^3$ and $R^3$ is hydrogen, and $A^4$ is $CR^4$ and $R^4$ is hydrogen.

In some embodiments of the invention, the 6-membered ring comprising $A^1$ to $A^4$ is a phenyl (where $A^1$, $A^2$, $A^3$ and $A^4$ are C—H), a pyridinyl (where $A^1$ is N and $A^2$, $A^3$ and $A^4$ are C—H, or $A^3$ is N and $A^1$, $A^2$ and $A^4$ are C—H), a fluorophenyl (where $A^1$ is C—F and $A^2$, $A^3$ and $A^4$ are C—H, or $A^3$ is C—F and $A^1$, $A^2$ and $A^4$ are C—H) or a difluorophenyl (eg, where $A^1$ and $A^2$ are C—F and $A^3$ and $A^4$ are C—H, or A and $A^3$ are C—F and $A^2$ and $A^4$ are C—H) group.

$R^5$ and $R^6$ independently represent hydrogen, halogen, cyano, difluoromethyl, trifluoromethyl, or $C_{1-4}$alkyl, or together with the carbon atom to which they are bonded represent cyclopropyl. Preferably, $R^5$ and $R^6$ are hydrogen, or $R^5$ is hydrogen and $R^6$ is methyl, or $R^5$ and $R^6$ are methyl. Most preferably, $R^5$ and $R^6$ are hydrogen.

Z represents a group selected from Z-1, Z-2, Z-3, Z-4, Z-5 (Z-5a, Z-5b, Z-5c, Z-5d, Z-5e, Z-5f, Z-5g) or Z-6 (Z-6a, Z-6b, Z-6c, Z-6d) as defined herein. Preferably, Z represents Z-1, Z-2 or Z-3, and, in particular Z-2 or Z-3. More preferably, Z represents Z-1, Z-2 or Z-3 when X is C(O), and, in particular Z represents Z-2 or Z-3, when X is C(O).

In some embodiments of the invention, Z represents:

Z-1 wherein $B^1$ and $B^2$ represent $C(R^7)(R^8)$;

Z-2 wherein $B^1$, $B^2$ and $B^3$ independently represent $C(R^7)(R^8)$, O, $NR^9$ or C(═O), wherein only one of $B^1$, $B^2$ and $B^3$ may be O, $NR^9$ or C(═O);

Z-3 wherein $B^1$, $B^2$, $B^3$ and $B^4$ independently represent $C(R^7)(R^8)$, $NR^9$ or C(═O), wherein one of $B^1$, $B^2$, $B^3$ and $B^4$ may be $NR^9$ and one of $B^1$, $B^2$, $B^3$ and $B^4$ may be C(═O);

Z-3 wherein $B^1$, $B^2$, $B^3$ and $B^4$ independently represent $C(R^7)(R^8)$, O, $NR^9$ or C(═O), wherein only one of $B^1$, $B^2$, $B^3$ and $B^4$ may be O, $NR^9$ or C(═O);

Z-6a wherein Y represents $C(R^7)$═$C(R^8)$; or Z-6c wherein Y represents $C_{2-4}$alkylene.

More preferably, Z represents:

Z-2 wherein $B^1$ and $B^3$ independently represent $C(R^7)(R^8)$, O, $NR^9$ or C(═O) wherein only one of $B^1$ and $B^3$ may be a O, $NR^9$ or C(═O), and $B^2$ represents $C(R^7)(R^8)$; or Z-3 wherein $B^1$, $B^2$ and $B^4$ independently represent $C(R^7)(R^8)$, O, $NR^9$ or C(═O) wherein only one of $B^1$, $B^2$ and $B^4$ may be O, $NR^9$ or C(═O), and $B^3$ represents $C(R^7)(R^8)$.

In other embodiments of the invention, Z represents:

Z-2 wherein $B^1$ and $B^3$ independently represent $C(R^7)(R^8)$, O or C(═O) wherein only one of $B^1$ and $B^3$ may be O or C(═O), and $B^2$ represents $C(R^7)(R^8)$, wherein $R^7$ and $R^8$, independently of each other, are selected from hydrogen or $C_{1-4}$alkyl; or Z-2 wherein $B^1$ and $B^2$ are $C(R^7)(R^8)$ wherein $R^7$ and $R^8$, independently of each other, are selected from hydrogen or $C_{1-4}$alkyl (and preferably hydrogen or methyl), and $B^3$ is O or C(═O) (and preferably O); or Z-3 wherein $B^1$, $B^2$ and $B^4$ independently represent $C(R^7)(R^8)$, O, $NR^9$ or C(═O) wherein only one of $B^1$, $B^2$ and $B^4$ may be a O, $NR^9$ or C(═O), and $B^3$ represents $C(R^7)(R^8)$, wherein $R^7$ and $R^8$, independently of each other, are selected from hydrogen or $C_{1-4}$alkyl; or Z-3 wherein $B^1$, $B^2$ and $B^3$ are $C(R^7)(R^8)$ wherein $R^7$ and $R^8$, independently of each other, are selected from hydrogen or $C_{1-4}$alkyl (and preferably hydrogen or methyl), and $B^4$ is O or C(═O) (and preferably O).

In some embodiments of the invention, Z represents:

Z-3 wherein $B^1$ and $B^3$ represent $C(R^7)(R^8)$, $B^2$ represents $NR^9$ and $B^4$ is C(═O).

Otherwise, according to the invention, when X is C(O) and n is 1, Z is represented by Z-1 wherein $B^1$ and $B^2$ represent $C(R^7)(R^8)$; or Z-2 wherein $B^1$, $B^2$ and $B^3$ independently represent $C(R^7)(R^8)$, O or C(═O), wherein only one of $B^1$, $B^2$ and $B^3$ may be O or C(═O); or Z-3 wherein $B^1$, $B^2$, $B^3$ and $B^4$ independently represent $C(R^7)(R^8)$, O or C(═O), wherein only one of $B^1$, $B^2$, $B^3$ and $B^4$ may be O or C(═O); or Z-6a wherein Y represents $C(R^7)$═$C(R^8)$; or Z-6c wherein Y represents $C_2$-$C_4$alkylene; or when X is $S(O)_2$, Z-2 wherein $B^1$, $B^2$ and $B^3$ independently represent $C(R^7)(R^8)$. More preferably, when X is C(O), Z is Z-2 wherein $B^1$, $B^2$ and $B^3$ independently represent $C(R^7)(R^8)$ or O, wherein only one of $B^1$, $B^2$ and $B^3$ may be O; or Z-3 wherein $B^1$, $B^2$, $B^3$ and $B^4$ independently represent $C(R^7)(R^8)$ or O, wherein only one of $B^1$, $B^2$, $B^3$ and $B^4$ may be O.

In other embodiments of the invention, when X is C(O) and n is 1, Z is represented by Z-1 wherein $B^1$ and $B^2$ represent $C(R^7)(R^8)$; or Z-2 wherein $B^1$, $B^2$ and $B^3$ independently represent $C(R^7)(R^8)$, O or C(═O), wherein only one of $B^1$, $B^2$ and $B^3$ may be O or C(═O); or Z-3 wherein $B^1$, $B^2$, $B^3$ and $B^4$ independently represent $C(R^7)(R^8)$, O or C(═O), wherein only one of $B^1$, $B^2$, $B^3$ and $B^4$ may be O or C(═O); or Z-6a wherein Y represents $C(R^7)$═$C(R^8)$; or Z-6c wherein Y represents $C_2$-$C_4$alkylene; or when X is $S(O)_2$, Z-2 wherein $B^1$, $B^2$ and $B^3$ independently represent $C(R^7)(R^8)$.

In some embodiments of the invention, in Z-3, $B^1$, $B^2$, $B^3$ and $B^4$ may independently represent $C(R^7)(R^8)$, O, S, $NR^9$ or C(═O), wherein only one of $B^1$, $B^2$, $B^3$ and $B^4$ may be a group selected from O, S, $NR^9$ or C(═O).

Preferred Z groups include:

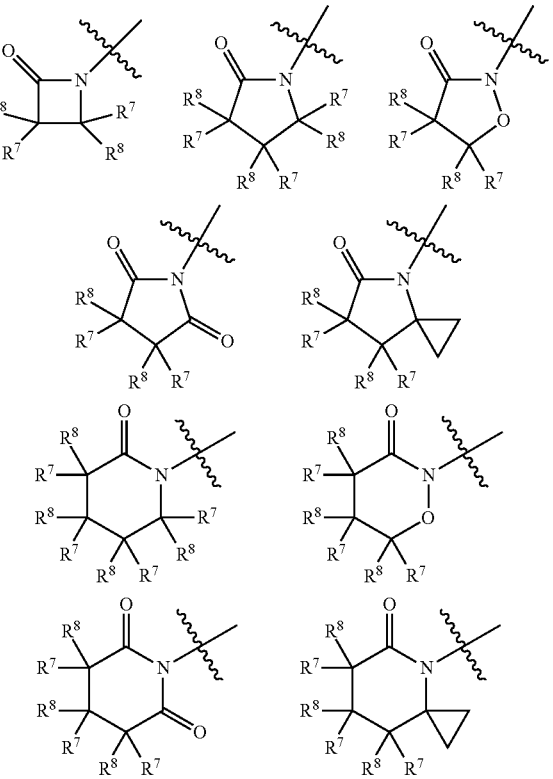

-continued

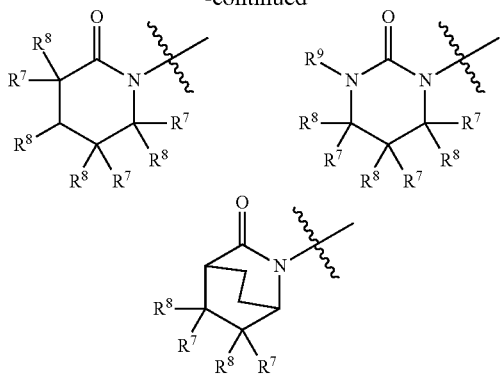

$R^7$ and $R^8$ independently represent hydrogen, halogen, $C_1$-$C_4$alkyl, $C_1$-$C_4$haloalkyl or $C_1$-$C_4$alkoxy. Preferably, $R^7$ and $R^8$ independently represent hydrogen, fluoro, chloro, methyl, ethyl, difluoromethyl, trifluoromethyl or methoxy. More preferably, $R^7$ and $R^8$ independently represent hydrogen, methyl, difluoromethyl, trifluoromethyl or methoxy. Even more preferably, $R^7$ is hydrogen or methyl, and $R^8$ represents hydrogen, methyl, difluoromethyl, trifluoromethyl or methoxy. Still more preferably, $R^7$ and $R^8$ independently represent hydrogen or methyl.

$R^9$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^{10}$, $C(O)OR^{10}$, $C(O)N(R^{10})R^{11}$, $S(O)_2R^{10}$ or $S(O)_2N(R^1)R^{11}$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano. Preferably, $R^9$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^{10}$, $C(O)OR^{10}$ or $C(O)N(R^{10})R^{11}$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano. More preferably, $R^9$ represents hydrogen, $C_{1-4}$alkyl, $C_{1-4}$alkoxy, $C(O)R^{10}$, $C(O)OR^{10}$, $C(O)N(R^{10})R^1$, $S(O)_2R^{10}$ or $S(O)_2N(R^1)R^{11}$. Even more preferably, $R^9$ represents hydrogen, $C_{1-4}$alkyl, $C(O)R^{10}$, $C(O)OR^{10}$ or $C(O)N(R^{10})R^{11}$.

$R^{10}$ represents hydrogen, $C_{1-6}$alkyl, $C_{3-6}$cycloalkyl, $C_{3-6}$cycloalkylC$_{1-2}$alkyl, $C_{1-4}$alkoxyC$_{1-4}$alkyl, wherein $C_{1-6}$alkyl, $C_{3-6}$cycloalkyl, $C_{3-6}$cycloalkyl-C$_{1-2}$alkyl and $C_{1-4}$alkoxy-C$_{1-4}$alkyl are optionally substituted by halogen or cyano. Preferably, $R^{10}$ represents hydrogen, $C_{1-4}$alkyl or $C_{1-4}$alkoxyC$_{1-4}$alkyl.

$R^{11}$ represents hydrogen, $C_{1-4}$alkyl, $C_{1-4}$haloalkyl, $C_{1-4}$alkoxy or $C_{1-4}$alkoxyC$_{1-4}$alkyl. Preferably, $R^{11}$ represents hydrogen or $C_{1-4}$alkyl.

In some embodiments according to the invention (in the compounds of Formula (I)):
Preferably, $A^1$ is N or $CR^1$, wherein $R^1$ is hydrogen or halogen;
$A^2$ is $CR^2$ and $R^2$ is hydrogen; $A^3$ is $CR^3$ and $R^3$ is hydrogen; and $A^4$ is $CR^4$ and $R^4$ is hydrogen;
n is 0 or 1;
$R^5$ and $R^6$ are hydrogen, or $R^5$ is hydrogen and $R^6$ is methyl, or $R^5$ and $R^6$ are methyl;
X is $C(O)$ or $S(O)_2$;
Z represents Z-2 wherein $B^1$ and $B^3$ independently represent $C(R^7)(R^8)$, O, $NR^9$ or $C(=O)$ wherein only one of $B^1$ and $B^3$ may be a O, $NR^9$ or $C(=O)$, and $B^2$ represents $C(R^7)(R^8)$; or Z-3 wherein $B^1$, $B^2$ and $B^4$ independently represent $C(R^7)(R^8)$, O, $NR^9$ or $C(=O)$ wherein only one of $B^1$, $B^2$ and $B^4$ may be a O, $NR^9$ or $C(=O)$, and $B^2$ represents $C(R^7)(R^8)$;

$R^7$ and $R^8$ independently represent hydrogen, methyl, difluoromethyl, trifluoromethyl or methoxy;
$R^9$ represents hydrogen, $C_{1-4}$alkyl, $C(O)R^{10}$, $C(O)OR^{10}$ or $C(O)N(R^{10})R^{11}$
$R^{10}$ represents hydrogen, $C_{1-4}$alkyl or $C_{1-4}$alkoxyC$_{1-4}$alkyl; and
$R^{11}$ represents hydrogen or $C_{1-4}$alkyl.
More preferably, $A^1$ represents $CR^1$ and $R^1$ is hydrogen; $A^2$ is $CR^2$ and $R^2$ is hydrogen; $A^3$ is $CR^3$ and $R^3$ is hydrogen; and $A^4$ is $CR^4$ and $R^4$ is hydrogen;
n is 1;
$R^5$ and $R^6$ are hydrogen;
X is $C(O)$;
Z represents Z-2 wherein $B^1$ and $B^3$ independently represent $C(R^7)(R^8)$, O, $NR^9$ or $C(=O)$ wherein only one of $B^1$ and $B^3$ may be a O, $NR^9$ or $C(=O)$, and $B^2$ represents $C(R^7)(R^8)$; or Z-3 wherein $B^1$, $B^2$ and $B^4$ independently represent $C(R^7)(R^8)$, O, $NR^9$ or $C(=O)$ wherein only one of $B^1$, $B^2$ and $B^4$ may be a O, $NR^9$ or $C(=O)$, and $B^2$ represents $C(R^7)(R^8)$;
$R^7$ and $R^8$ independently represent hydrogen, methyl, difluoromethyl, trifluoromethyl or methoxy;
$R^9$ represents hydrogen, $C_{1-4}$alkyl, $C(O)R^{10}$, $C(O)OR^{10}$ or $C(O)N(R^{10})R^{11}$;
$R^{10}$ represents hydrogen, $C_{1-4}$alkyl or $C_{1-4}$alkoxyC$_{1-4}$alkyl; and
$R^{11}$ represents hydrogen or $C_{1-4}$alkyl.
In other embodiments according to the invention:
Preferably, $A^1$ represents N or $CR^1$, wherein $R^1$ is selected from hydrogen or fluoro; $A^2$ is $CR^2$ and $R^2$ is hydrogen; $A^3$ is $CR^3$ and $R^3$ is hydrogen; and $A^4$ is $CR^4$ and $R^4$ is hydrogen;
n is 1;
$R^5$ and $R^6$ are hydrogen, or $R^5$ is hydrogen and $R^6$ is methyl, or $R^5$ and $R^6$ are methyl;
Z when X is $C(O)$ represents Z-1, Z-2, Z-3, Z-5a or Z-5c, or
Z when X is $S(O)_2$ represents Z-2 or Z-3; and
$R^7$ and $R^8$ independently represent hydrogen, chloro, fluoro, methyl, ethyl, difluoromethyl, trifluoromethyl or methoxy.
More preferably, $A^1$ represents N or $CR^1$, wherein $R^1$ is selected from hydrogen or fluoro; $A^2$ is $CR^2$ and $R^2$ is hydrogen; $A^3$ is $CR^3$ and $R^3$ is hydrogen; and $A^4$ is $CR^4$ and $R^4$ is hydrogen;
n is 1;
$R^5$ and $R^6$ are hydrogen, or $R^5$ is hydrogen and $R^6$ is methyl, or $R^5$ and $R^6$ are methyl;
X is $C(O)$;
Z represents Z-1, Z-2, Z-3, Z-6a or Z-6c; and
$R^7$ and $R^8$ independently represent hydrogen, chloro, fluoro, methyl, ethyl, difluoromethyl, trifluoromethyl or methoxy.
Even more preferably, $A^1$ represents N or $CR^1$, wherein $R^1$ is hydrogen; $A^2$ is $CR^2$ and $R^2$ is hydrogen, $A^3$ is $CR^3$ and $R^3$ is hydrogen, and $A^4$ is $CR^4$ and $R^4$ is hydrogen;
n is 1;
$R^5$ and $R^6$ are hydrogen;
X is $C(O)$;
Z represents Z-1 wherein $B^1$ and $B^2$ represent $C(R^7)(R^8)$; Z-2 wherein $B^1$, $B^2$ and $B^3$ independently represent $C(R^7)(R^8)$, O or $C(=O)$, wherein only one of $B^1$, $B^2$ and $B^3$ may be O or $C(=O)$; Z-3 wherein $B^1$, $B^2$, $B^3$ and $B^4$ independently represent $C(R^7)(R^8)$, O or $C(=O)$, wherein only one of $B^1$, $B^2$, $B^3$ and $B^4$ may be O or C(=O); Z-6a wherein Y is C($R^7$)=(C$R^8$) or Z-6c wherein Y is $C_{2-4}$alkylene; and $R^7$ and $R^8$ independently represent hydrogen, methyl, difluoromethyl, trifluoromethyl or methoxy.

Still more preferably, $A^1$ represents C$R^1$ and $R^1$ is hydrogen, $A^2$ is C$R^2$ and $R^2$ is hydrogen, $A^3$ is C$R^3$ and $R^3$ is hydrogen, and $A^4$ is C$R^4$ and $R^4$ is hydrogen;

n is 1;

$R^5$ and $R^6$ are hydrogen;

X is C(O);

Z represents Z-2 wherein $B^1$, $B^2$ and $B^3$ independently represent C($R^7$)($R^8$) or O, wherein only one of $B^1$, $B^2$ and $B^3$ may be O, or Z-3 wherein $B^1$, $B^2$, $B^3$ and $B^4$ independently represent C($R^7$)($R^8$) or O, wherein only one of $B^1$, $B^2$, $B^3$ and $B^4$ may be O; and $R^7$ and $R^8$ independently represent hydrogen or methyl.

Further more preferably, $A^1$ represents C$R^1$ and $R^1$ is hydrogen, $A^2$ is C$R^2$ and $R^2$ is hydrogen, $A^3$ is C$R^3$ and $R^3$ is hydrogen, and $A^4$ is C$R^4$ and $R^4$ is hydrogen;

n is 1;

$R^5$ and $R^6$ are hydrogen;

X is C(O);

Z represents Z-2 wherein $B^1$, $B^2$ and $B^3$ independently represent C($R^7$)($R^8$), or Z-3 wherein $B^1$, $B^2$, $B^3$ and $B^4$ independently represent C($R^7$)($R^8$); and $R^7$ and $R^8$ independently represent hydrogen or methyl.

In still further embodiments of the invention:

Preferably, $A^1$ is N or C$R^1$ wherein $R^1$ is hydrogen or fluorine, $A^2$ is C$R^2$ and $R^2$ is hydrogen, $A^3$ is N or C$R^3$ and $R^3$ is hydrogen or fluorine, and $A^4$ is C$R^4$ and $R^4$ is hydrogen;

n is 1;

$R^5$ and $R^6$ are hydrogen, or $R^5$ is hydrogen and $R^6$ is methyl, or $R^5$ and $R^6$ are methyl;

X is C(O);

Z represents:

Z-1 wherein $B^1$ and $B^2$ are C($R^7$)($R^8$) and wherein $R^7$ is hydrogen and $R^8$ is hydrogen, methyl, ethyl, difluoromethyl, trifluoromethyl or methoxy;

Z-2 wherein $B^1$ is C($R^7$)($R^8$) wherein $R^7$ and $R^8$ are independently selected from hydrogen and $C_{1-4}$alkyl, $B^2$ is C($R^7$)($R^8$) wherein $R^7$ and $R^8$ are independently selected from hydrogen and $C_{1-4}$alkyl; and $B^3$ is C($R^7$)($R^8$) wherein $R^7$ and $R^8$ are independently selected from hydrogen and $C_{1-4}$alkyl, O or C(=O);

Z-3 wherein $B^1$ is selected from C($R^7$)($R^8$) and wherein $R^7$ and $R^8$ are independently selected from hydrogen and $C_{1-4}$alkyl, or N$R^9$ wherein $R^9$ is selected from hydrogen or $C_{1-4}$alkyl; $B^2$ is selected from C($R^7$)($R^8$) wherein $R^7$ and $R^8$ are independently selected from hydrogen and $C_{1-4}$alkyl, or N$R^9$ wherein $R^9$ is selected from C(O)N($R^{10}$)$R^{11}$ or S(O)$_2$N($R^{10}$)$R^{11}$, wherein $R^{10}$ is selected from hydrogen, or methyl and $R^{11}$ is selected from hydrogen, methyl or methoxy; $B^3$ is C($R^7$)($R^8$) wherein $R^7$ and $R^8$ are independently selected from hydrogen and $C_{1-4}$alkyl; and $B^4$ is selected from C($R^7$)($R^8$) wherein $R^7$ and $R^8$ are independently selected from hydrogen and $C_{1-4}$alkyl, 0 or C(=O), wherein only one of $B^1$ and $B^2$ may be N$R^9$;

Z-5c wherein a is 0 or 1, and $R^7$ and $R^8$ are independently selected from hydrogen and $C_1$-4alkyl;

Z-5g wherein a is 0 or 1, and $R^7$ and $R^8$ are independently selected from hydrogen and $C_1$-4alkyl; or Z-6c wherein Y is $C_{2-3}$alkylene, and $R^7$ and $R^8$ are independently selected from hydrogen and $C_{1-4}$alkyl.

More preferably, $A^1$ is C$R^1$ and $R^1$ is hydrogen, $A^2$ is C$R^2$ and $R^2$ is hydrogen, $A^3$ is C$R^3$ and $R^3$ is hydrogen, and $A^4$ is C$R^4$ and $R^4$ is hydrogen;

n is 1;

$R^5$ and $R^6$ are hydrogen;

X is C(O);

Z represents:

Z-1 wherein $B^1$ and $B^2$ are C($R^7$)($R^8$) and wherein $R^7$ is hydrogen and $R^8$ is hydrogen, methyl, difluoromethyl, trifluoromethyl or methoxy;

Z-2 wherein $B^1$ is C($R^7$)($R^8$) wherein $R^7$ and $R^8$ are independently selected from hydrogen and methyl, $B^2$ is C($R^7$)($R^8$) wherein $R^7$ and $R^8$ are independently selected from hydrogen and methyl; and $B^3$ is C($R^7$)($R^8$) wherein $R^7$ and $R^8$ are independently selected from hydrogen and methyl, O or C(=O);

Z-3 wherein $B^1$ is selected from C($R^7$)($R^8$) and wherein $R^7$ and $R^8$ are independently selected from hydrogen and methyl, or N$R^9$ wherein $R^9$ is selected from hydrogen or $C_{1-4}$alkyl; $B^2$ is selected from C($R^7$)($R^8$) wherein $R^7$ and $R^8$ are independently selected from hydrogen and methyl, or N$R^9$ wherein $R^9$ is selected from C(O)N($R^{10}$)$R^{11}$ or S(O)$_2$N($R^{10}$)$R^{11}$, wherein $R^{10}$ is selected from hydrogen or methyl and $R^{11}$ is selected from hydrogen, methyl or methoxy; $B^3$ is C($R^7$)($R^8$) wherein $R^7$ and $R^8$ are independently selected from hydrogen and methyl; and $B^4$ is selected from C($R^7$)($R^8$) wherein $R^7$ and $R^8$ are independently selected from hydrogen and methyl, O or C(=O), wherein only one of $B^1$ and $B^2$ may be N$R^9$;

Z-5c wherein a is 0, and $R^7$ and $R^8$ are independently selected from hydrogen and methyl;

Z-5g wherein a is 0, and $R^7$ and $R^8$ are independently selected from hydrogen and methyl; or Z-6c wherein Y is $C_{2-3}$alkylene, and $R^7$ and $R^8$ are independently selected from hydrogen and methyl.

Even more preferably, $A^1$ is C$R^1$ and $R^1$ is hydrogen, $A^2$ is C$R^2$ and $R^2$ is hydrogen, $A^3$ is C$R^3$ and $R^3$ is hydrogen, and $A^4$ is C$R^4$ and $R^4$ is hydrogen;

n is 1;

$R^5$ and $R^6$ are hydrogen;

X is C(O);

Z represents:

Z-1 wherein $B^1$ and $B^2$ are C($R^7$)($R^8$) and wherein $R^7$ is hydrogen and $R^8$ is hydrogen, methyl, difluoromethyl or trifluoromethyl;

Z-2 wherein $B^1$ is C($R^7$)($R^8$) wherein $R^7$ and $R^8$ are independently selected from hydrogen and methyl, $B^2$ is C($R^7$)($R^8$) wherein $R^7$ and $R^8$ are independently selected from hydrogen and methyl; and $B^3$ is C($R^7$)($R^8$) wherein $R^7$ and $R^8$ are independently selected from hydrogen and methyl, O or C(=O);

Z-3 wherein $B^1$ is selected from C($R^7$)($R^8$) and wherein $R^7$ and $R^8$ are independently selected from hydrogen and methyl, or N$R^9$ wherein $R^9$ is selected from hydrogen or methyl; $B^2$ is selected from C($R^7$)($R^8$) wherein $R^7$ and $R^8$ are independently selected from hydrogen and methyl, or N$R^9$ wherein $R^9$ is selected from C(O)N($R^{10}$)$R^{11}$ or S(O)$_2$N($R^{10}$)$R^{11}$, wherein $R^{10}$ is selected from hydrogen or methyl and $R^{11}$ is selected from hydrogen, methyl or methoxy; $B^3$ is C($R^7$)($R^8$) wherein $R^7$ and $R^8$ are independently selected from hydrogen and methyl; and $B^4$ is selected from C($R^7$)

($R^8$) wherein $R^7$ and $R^8$ are independently selected from hydrogen and methyl, or C(=O), wherein only one of $B^1$ and $B^2$ may be $NR^9$;

Z-5c wherein a is 0, and $R^7$ and $R^8$ are independently selected from hydrogen and methyl;

Z-5g wherein a is 0, and $R^7$ and $R^8$ are independently selected from hydrogen and methyl; or Z-6c wherein Y is ethylene, and $R^7$ and $R^8$ are independently selected from hydrogen and methyl.

Preferably, the compound according to Formula (I) is selected from a compound A-1 to A-70 described in Table A (below), a compound B-1 to B-4 described in Table B (below), a compound C-1 to C-3 described in Table C (below), or compound D-1 described in Table D (below).

The compounds of the present invention may be enantiomers of the compound of Formula (I) as represented by a Formula (I-a) or a Formula (I-b), wherein n is 1, and $R^5$ and $R^6$ are different.

present in a reversible equilibrium with the corresponding covalently hydrated forms (ie, the compounds of formula (I-I) and formula (I-II) as shown below) at the $CF_3$-oxadiazole motif. This dynamic equilibrium may be important for the biological activity of the compounds of Formula (I).

The designations of n, $A^1$, $A^2$, $A^3$, $A^4$, Z (X, Y, a, $B^1$, $B^2$, $B^3$, $B^4$, $B^5$), $R^1$, $R^2$, $R^3$, $R^4$, $R^5$, $R^6$, $R^7$, $R^8$, $R^9$, $R^{10}$ and $R^{11}$, with reference to the compounds of formula (I) of the present invention apply generally to the compounds of Formula (I-I) and Formula (I-II), as well as to the specific disclosures of combinations of n, $A^1$, $A^2$, $A^3$, $A^4$, Z (X, Y, a, $B^1$, $B^2$, $B^3$, $B^4$, $B^5$), $R^1$, $R^2$, $R^3$, $R^4$, $R^5$, $R^6$, $R^7$, $R^8$, $R^9$, $R^{10}$ and $R^{11}$ as represented in Tables 1a to 1d below, or the compounds A-1 to A-70 described in Table A (below), the compounds B-1 to B-4 described in Table B (below), the compounds C-1 to C-3 described in Table C (below), or compound D-1 described in Table D (below).

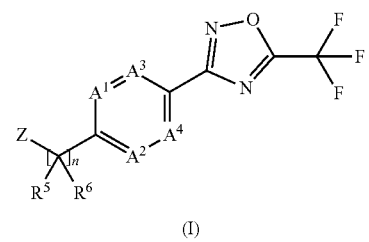

(I)

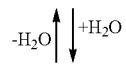

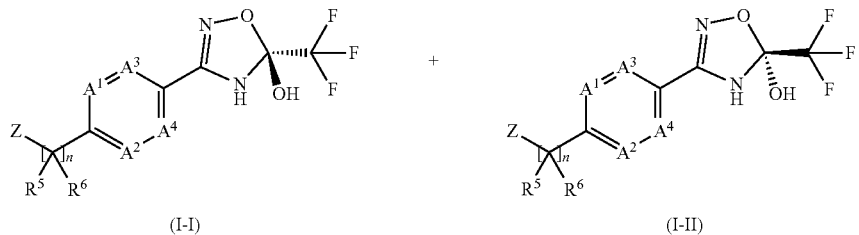

(I-I)            (I-II)

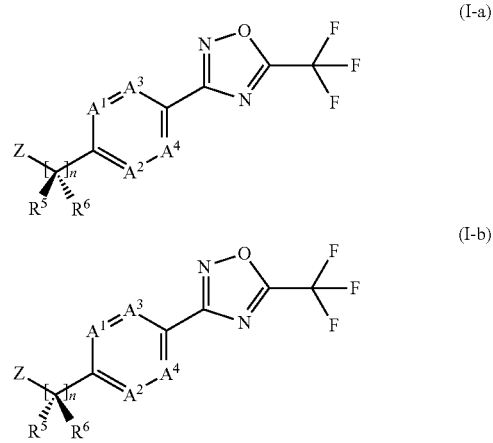

It is understood that when in aqueous media, the compounds of formula (I) according to the invention may be Compounds of the present invention can be made as shown in the following schemes 1 to 10, in which, unless otherwise stated, the definition of each variable is as defined above for a compound of formula (I).

Compounds of formula (I) can be prepared from compounds of formula (III), wherein X is F, Cl, Br, I, or $OSO_2Me$, via treatment with compounds of formula (II), in the presence of a base (e.g. lithium hexamethyldisilylazide, n-butyllithium, $Cs_2CO_3$, CSF, $K_2CO_3$ or NaH) in a suitable solvent (e.g. dimethylformamide, acetone or tetrahydrofuran) at a temperature between −78° C. and 25° C. Additionally, some reactions might only proceed at higher temperature and/or in the presence of a catalyst system such as CuI/dimethylethylenediamine or $Pd(OAc)_2$/Xantphos. For related examples, see: WO 2004/087646; WO 2013/132253; Garcia, M. et al Org. Biomol. Chem. 2004, 11, 1633; Guyonner, M. and Baudoin, O. Org. Lett. 2012, 14, 398; Philipps, D. P. et al. Tetrahedron Lett. 2009, 50, 7293. This reaction is shown in Scheme 1.

Scheme 1

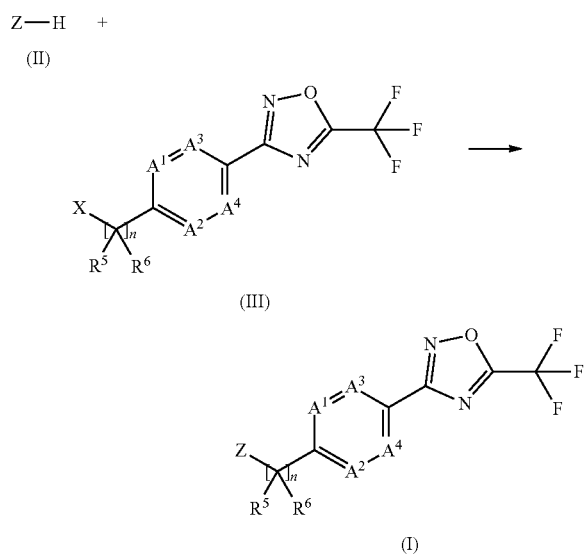

Alternatively, compounds of formula (I), or compounds of formula (XII), can be prepared from compounds of formula (IV) or (IVa), respectively, by treatment with trifluoroacetic anhydride in the presence of a base (e.g. pyridine or 4-dimethylaminopyridine) in a suitable solvent, such as tetrahydrofuran or ethanol, at a temperature between 25° C. and 75° C. For related examples see: WO 2003/028729 and WO 2010/045251. This reaction is shown in Scheme 2.

Scheme 2

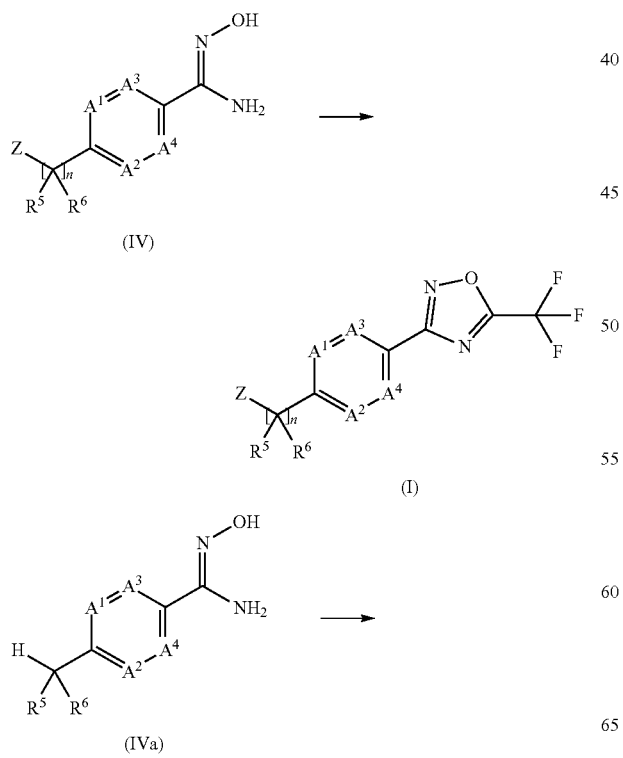

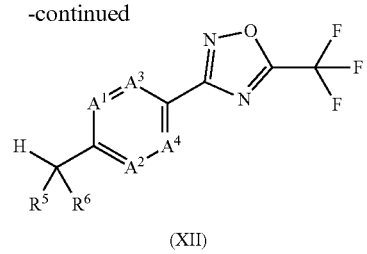

Compounds of formula (IV) and (IVa) can be prepared from compounds of formula (V) and (Va), respectively, by treating them with a hydroxylamine hydrochloride salt in the presence of a base, such as triethylamine, in a suitable solvent, such as methanol, at a temperature between 0° C. and 65° C. For related examples, see Kitamura, S. et al. Chem. Pharm. Bull. (2001), 49, 268 and WO 2013/066838. This reaction is shown in Scheme 3.

Scheme 3

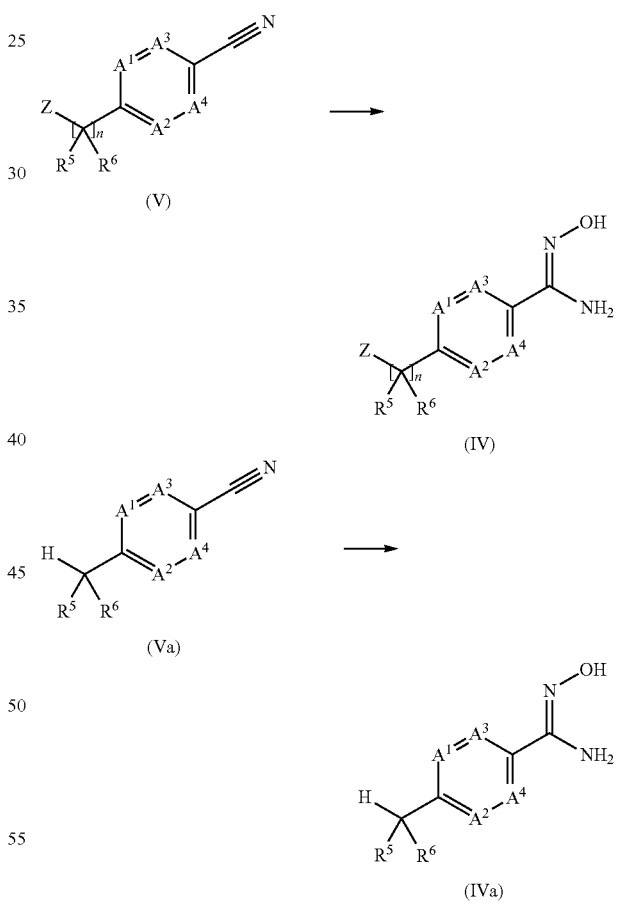

Compounds of formula (V) and (Va) can be prepared from compounds of formula (VI) and (VIa), respectively, wherein V is Br or I, via metal-promoted reaction with a suitable cyanide reagent, such as Pd(0)/Zn(CN)$_2$ or CuCN, in a suitable solvent (e.g. dimethylformamide or N-methylpyrrolidone) at elevated temperature between 100° C. and 120° C. For related examples, see US 2007/0155739 and WO 2009/022746. This reaction is shown in Scheme 4.

Scheme 4

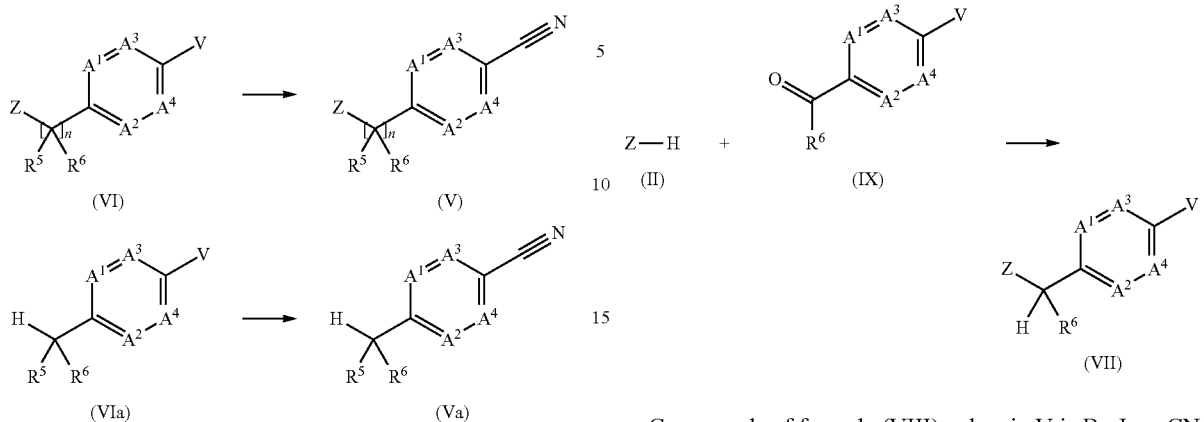

Compounds of formula (VI), wherein V is Br or I, or CN (also corresponding to compound (V)), can be prepared from compounds of formula (VIII), wherein X is F, Cl, Br, I, or $OSO_2Me$, via treatment with compounds of formula (II), in the presence of a base (e.g. lithium hexamethyldisilylazide, n-butyllithium, $Cs_2CO_3$, CSF, $K_2CO_3$ or NaH) in a suitable solvent (e.g. dimethylformamide, acetone or tetrahydrofuran) at a temperature between −78° C. and 25° C. Additionally, some reactions might only proceed at higher temperature and/or in the presence of a catalyst system such as CuI/dimethylethylenediamine or $Pd(OAc)_2$/Xantphos. For related examples, see: WO 2004/087646; WO 2013/132253; Garcia, M. et al *Org. Biomol. Chem.* 2004, 11, 1633; Guyonner, M. and Baudoin, O. *Org. Lett.* 2012, 14, 398; Philipps, D. P. et al. *Tetrahedron Lett.* 2009, 50, 7293. This reaction is shown in Scheme 5.

Scheme 5

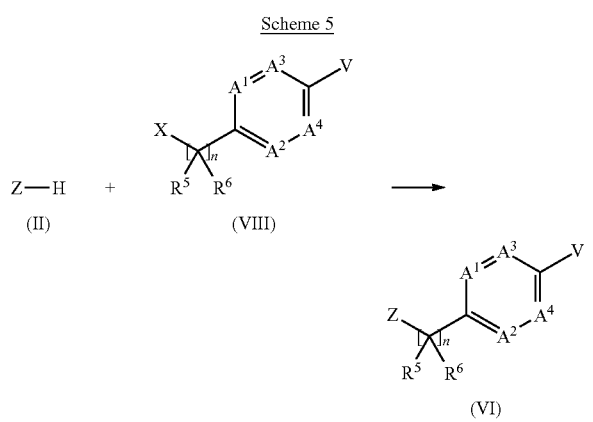

Compounds of formula (VII) (i.e., compounds of Formula (VI) wherein $R^5$ is H) wherein V is Br, I, or CN, can be prepared from carbonyl compounds of formula (IX), via treatment with compounds of formula (II) in the presence of a base, such as triethylamine, in a suitable solvent (eg, methanol or ethanol) at a temperature between 0° C. and 100° C.; followed by the addition of a reducing reagent (e.g. $NaBH_4$ or $NaBH_3CN$). For related examples, see: WO 2013/071232 and WO 2013/066838. This reaction is shown in Scheme 6.

Scheme 6

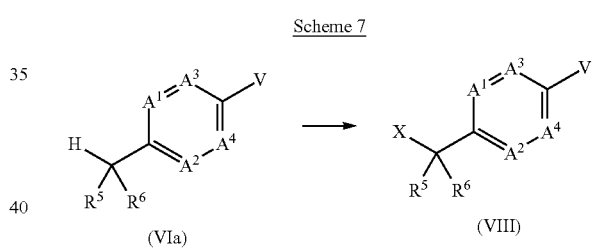

Compounds of formula (VIII), wherein V is Br, I, or CN and X is Cl or Br, are either commercially available or can be prepared from compounds of formula (VIa), by treatment with a halogen source, (eg, N-bromosuccimide (NBS) or N-chlorosuccimide (NCS)) and a radical initiator, such as $(PhCO_2)_2$ or azobisisobutyronitrile (AIBN), in the presence of ultraviolet light, in a suitable solvent, such as tetrachloromethane, at temperatures between 55° C. and 100° C. For related examples, see Liu, S. et al *Synthesis* (2001), 14, 2078 and Kompella, A. et al *Org. Proc. Res. Dev.* (2012), 16, 1794. This reaction is shown in Scheme 7. Compounds of formula (VIa) are commercially available.

Scheme 7

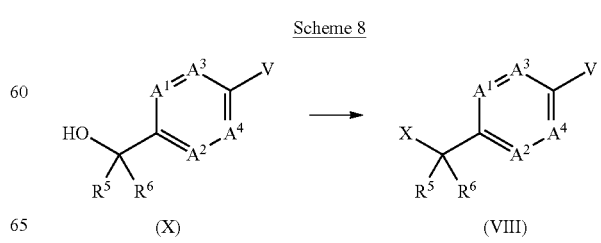

Alternatively, compounds of formula (VIII), wherein X is Cl, Br, I, or $OSO_2Me$ are either commercially available or can be prepared from compounds of formula (X), wherein V is Br, I or CN, by treatment with a halogen source (eg, $CBr_4$, $CCl_4$ or $I_2$) in the presence of triphenylphosphine, or with methanesulfonyl chloride ($ClSO_2Me$), in a suitable solvent, (eg, dichloromethane or 1,2-dichloroethane) at a temperature between 0° C. and 80° C. For related examples, see Liu, H. et al *Bioorg. Med. Chem.* (2008), 16, 10013; WO 2014/020350; and Kompella, A. et al *Bioorg. Med. Chem. Lett.* (2001), 1, 3161. Compounds of formula (X) are commercially available. This reaction is shown in Scheme 8.

Scheme 8

Compounds of formula (IX), wherein V is Br, I, or CN are either commercially available or can be prepared from compounds of formula (XI) (compound (X) when $R^5$ is H), by treatment with an oxidizing reagent (eg, $KMnO_4$ or $MnO_2$) in a suitable solvent, (eg, dioxane or dichloromethane) at a temperature between 25° C. and 110° C. For related examples, see WO 2003/0087940 and WO 2008/104306. Compounds of formula (XI) are commercially available. This reaction is shown in Scheme 9.

Scheme 9

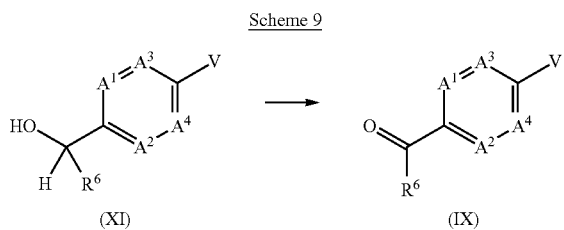

Compounds of formula (III) wherein X is Cl or Br, can be prepared from compounds of formula (XII) by treatment with a halogen source (eg, N-bromosuccimide (NBS) or N-chlorosuccimide (NCS)) and a radical initiator (eg, $(PhCO_2)_2$ or azobisisobutyronitrile (AIBN)) in a suitable solvent, such as tetrachloromethane, at temperatures between 55° and 100° C. in the presence of ultraviolet light. For related examples, see Liu, S. et al Synthesis (2001), 14, 2078 and Kompella, A. et al Org. Proc. Res. Dev. (2012), 16, 1794. This reaction is shown in Scheme 10.

Scheme 10

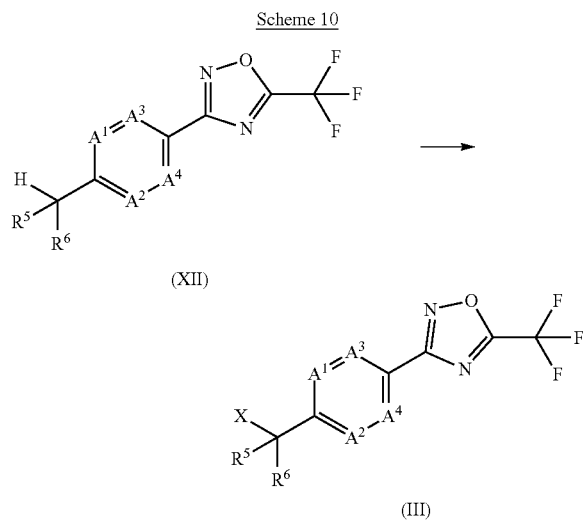

As already indicated, surprisingly, it has now been found that the novel compounds of formula (I) according to the invention have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of formula (I) before planting: seed, for example, can be dressed before being sown. The active compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula (I) are for example, effective against fungi and fungal vectors of disease as well as phytopathogenic bacteria and viruses. These fungi and fungal vectors of disease as well as phytopathogenic bacteria and viruses are for example:

Absidia corymbifera, Alternaria spp, Aphanomyces spp, Ascochyta spp, Aspergillus spp. including A. flavus, A. fumigatus, A. nidulans, A. niger, A. terrus, Aureobasidium spp. including A. pullulans, Blastomyces dermatitidis, Blumeria graminis, Bremia lactucae, Botryosphaeria spp. including B. dothidea, B. obtusa, Botrytis spp. including B. cinerea, Candida spp. including C. albicans, C. glabrata, C. krusei, C. lusitaniae, C. parapsilosis, C. tropicalis, Cephaloascus fragrans, Ceratocystis spp, Cercospora spp. including C. arachidicola, Cercosporidium personatum, Cladosporium spp, Claviceps purpurea, Coccidioides immitis, Cochliobolus spp, Colletotrichum spp. including C. musae, Cryptococcus neoformans, Diaporthe spp, Didymella spp, Drechslera spp, Elsinoe spp, Epidermophyton spp, Erwinia

*amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp., *Stereum hirsutum, Thanatephorus cucumeris, Thielaviopsis basicola, Tilletia* spp, *Trichoderma* spp. including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

The compounds of formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as 8-endotoxins, e.g. CryIAb, CryIAc, CryIF, CryIFa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example CryIAb, CryIAc, CryIF, CryIFa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated CryIAb, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIAb toxin); YieldGard Rootworm® (maize variety that expresses a Cry3Bb1 toxin); YieldGard Plus® (maize variety that expresses a CryIAb and a Cry3Bb1 toxin); Starlink® (maize variety that expresses a Cry9C toxin); Herculex I® (maize variety that expresses a CryIFa2 toxin and the enzyme phosphinothricine N-acetyltransferase (PAT) to achieve tolerance to the herbicide glufosinate ammonium); NuCOTN 33B® (cotton variety that expresses a CryIAc toxin); Bollgard I® (cotton variety that expresses a CryIAc toxin); Bollgard II® (cotton variety that expresses a CryIAc and a Cry2Ab toxin); VipCot® (cotton variety that expresses a Vip3A and a CryIAb toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIAb toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIAb toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIAb toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "*The Pesticide Manual*", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid m ethoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichlorophenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N,N-dimethyl-5-p- tolylimidazole-1-sulfonamide, N-allyl-4, 5-dimethyl-2-trimethylsilylthiophene-3-carboxamide, N—(I-cyano-1,2-dimethylpropyl)-2-(2, 4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-m ethylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-m ethoxyacrylate, methyl (E)-2-[2-[(3-methyl-pyridin-2-yloxymethyl)phenyl]-3-m ethoxyacrylate, methyl (E)-2-[2-[6-(2-methyl-phenoxy)pyrimidin-4-yloxy]phenyl]-3-m ethoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethyl pyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenzoquat, diflumetorim, O, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneaminooxycarbonyl) amino] thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, solatenol, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG- 505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as defined herein, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula I per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

Table 1a (below) discloses 46 combinations (compounds 1a.001 to 1a.046) of $A^1$, $A^2$, $A^3$, $A^4$, $R^5$, $R^7$ and $R^8$ substituents in accordance with compounds as defined for Formula (T-1). Formula (T-1) corresponds to Formula (I) as defined for the present invention.

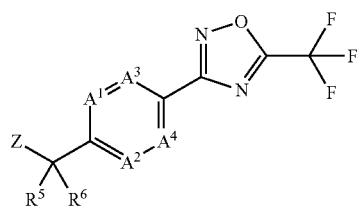

(T-1)

Each of Tables 2a to 22a (which follow Table 1a) make available 46 additional individual compounds of the formula (T-1) in which Z and $R^6$ are as specifically defined in Tables 2a to 22a (Formulae T-1a.2 to T-1a.22), which refer to Table 1a wherein $A^1$, $A^2$, $A^3$, $A^4$, $R^5$, $R^7$ and $R^8$ are specifically defined.

TABLE 1a

| Compound no. | $A^1$ | $A^2$ | $A^3$ | $A^4$ | $R^5$ | $R^7$ | $R^8$ |
|---|---|---|---|---|---|---|---|
| 1a.001 | C—H | C—H | C—H | C—H | H | H | H |
| 1a.002 | C—H | C—H | C—H | C—H | H | H | CH₃ |
| 1a.003 | C—H | C—H | C—H | C—H | H | CH₃ | CH₃ |
| 1a.004 | C—H | C—H | C—H | C—H | CH₃ | H | H |
| 1a.005 | C—H | C—H | C—H | C—H | CH₃ | H | CH₃ |
| 1a.006 | C—H | C—H | C—H | C—H | CH₃ | CH₃ | CH₃ |
| 1a.007 | C—F | C—H | C—H | C—H | H | H | H |
| 1a.008 | C—F | C—H | C—H | C—H | H | H | CH₃ |
| 1a.009 | C—F | C—H | C—H | C—H | H | CH₃ | CH₃ |
| 1a.010 | C—F | C—H | C—H | C—H | CH₃ | H | H |
| 1a.011 | C—F | C—H | C—H | C—H | CH₃ | H | CH₃ |
| 1a.012 | C—F | C—H | C—H | C—H | CH₃ | CH₃ | CH₃ |
| 1a.013 | C—CH₃ | C—H | C—H | C—H | H | H | H |
| 1a.014 | C—CH₃ | C—H | C—H | C—H | H | H | CH₃ |
| 1a.015 | C—CH₃ | C—H | C—H | C—H | H | CH₃ | CH₃ |
| 1a.016 | C—CH₃ | C—H | C—H | C—H | CH₃ | H | H |
| 1a.017 | N | C—H | C—H | C—H | H | H | H |
| 1a.018 | N | C—H | C—H | C—H | H | H | CH₃ |
| 1a.019 | N | C—H | C—H | C—H | H | CH₃ | CH₃ |
| 1a.020 | N | C—H | C—H | C—H | CH₃ | H | H |
| 1a.021 | N | C—H | C—H | C—H | CH₃ | H | CH₃ |

TABLE 1a-continued

| Compound no. | $A^1$ | $A^2$ | $A^3$ | $A^4$ | $R^5$ | $R^7$ | $R^8$ |
|---|---|---|---|---|---|---|---|
| 1a.022 | N | C—H | C—H | C—H | CH₃ | CH₃ | CH₃ |
| 1a.023 | C—Cl | C—H | C—H | C—H | H | H | H |
| 1a.024 | C—Cl | C—H | C—H | C—H | H | H | CH₃ |
| 1a.025 | C—Cl | C—H | C—H | C—H | H | CH₃ | CH₃ |
| 1a.026 | C—Cl | C—H | C—H | C—H | CH₃ | H | H |
| 1a.027 | C—OCH₃ | C—H | C—H | C—H | H | H | H |
| 1a.028 | C—OCH₃ | C—H | C—H | C—H | H | H | CH₃ |
| 1a.029 | C—OCH₃ | C—H | C—H | C—H | H | CH₃ | CH₃ |
| 1a.030 | C—OCH₃ | C—H | C—H | C—H | CH₃ | H | H |
| 1a.031 | C—CF₃ | C—H | C—H | C—H | H | H | H |
| 1a.032 | C—CF₃ | C—H | C—H | C—H | H | H | CH₃ |
| 1a.033 | C—CF₃ | C—H | C—H | C—H | H | CH₃ | CH₃ |
| 1a.034 | C—CF₃ | C—H | C—H | C—H | CH₃ | H | H |
| 1a.035 | C—H | C—H | C—F | C—H | H | H | H |
| 1a.036 | C—H | C—H | C—F | C—H | H | H | CH₃ |
| 1a.037 | C—H | C—H | C—F | C—H | H | CH₃ | CH₃ |
| 1a.038 | C—H | C—H | C—F | C—H | CH₃ | H | H |
| 1a.039 | C—H | C—H | N | C—H | H | H | H |
| 1a.040 | C—H | C—H | N | C—H | H | H | CH₃ |
| 1a.041 | C—H | C—H | N | C—H | H | CH₃ | CH₃ |
| 1a.042 | C—H | C—H | N | C—H | CH₃ | H | H |
| 1a.043 | N | N | C—H | C—H | H | H | H |
| 1a.044 | N | N | C—H | C—H | H | H | CH₃ |
| 1a.045 | N | N | C—H | C—H | H | CH₃ | CH₃ |
| 1a.046 | N | N | C—H | C—H | CH₃ | H | H |

Table 2a: This table discloses compounds 2a.001 to 2a.046 of the formula (T-1a.2), which is a compound of formula (I) wherein $R^6$ is H and $A^1$, $A^2$, $A^3$, $A^4$, $R^5$, $R^7$ and $R^8$ have the specific meanings given in the Table 1a.

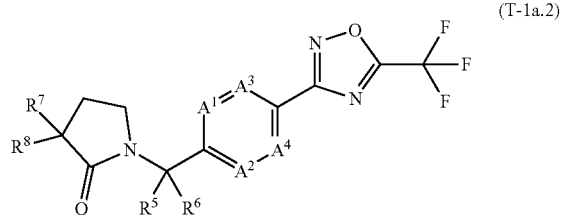

(T-1a.2)

Table 3a: This table discloses compounds 3a.001 to 3a.046 of the formula (T-1a.3), which is a compound of formula (I) wherein $R^6$ is H and $A^1$, $A^2$, $A^3$, $A^4$, $R^5$, $R^7$ and $R^8$ have the specific meanings given in the Table 1a.

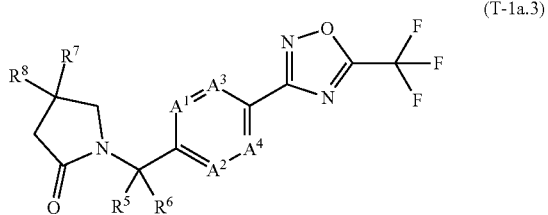

(T-1a.3)

Table 4a: This table discloses compounds 4a.001 to 4a.046 of the formula (T-1a.4), which is a compound of formula (I) wherein $R^6$ is H and $A^1$, $A^2$, $A^3$, $A^4$, $R^5$, $R^7$ and $R^8$ have the specific meanings given in the Table 1a.

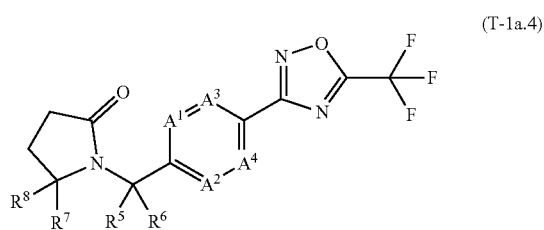
(T-1a.4)

Table 5a: This table discloses compounds 5a.001 to 5a.046 of the formula (T-1a.5), which is a compound of formula (I) wherein $R^6$ is H and $A^1, A^2, A^3, A^4, R^5, R^7$ and $R^8$ have the specific meanings given in the Table 1a.

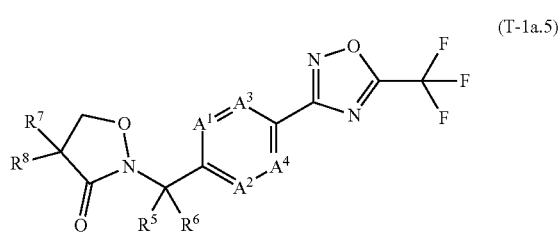
(T-1a.5)

Table 6a: This table discloses compounds 6a.001 to 6a.046 of the formula (T-1a.6), which is a compound of formula (I) wherein $R^6$ is H and $A^1, A^2, A^3, A^4, R^5, R^7$ and $R^8$ have the specific meanings given in the Table 1a.

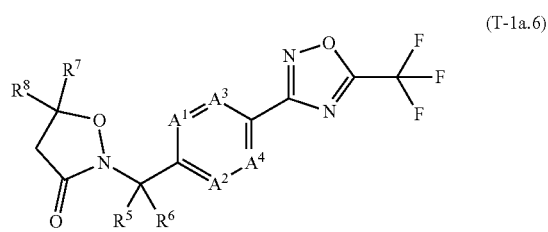
(T-1a.6)

Table 7a: This table discloses compounds 7a.001 to 7a.046 of the formula (T-1a.7), which is a compound of formula (I) wherein $R^6$ is H and $A^1, A^2, A^3, A^4, R^5, R^7$ and $R^8$ have the specific meanings given in the Table 1a.

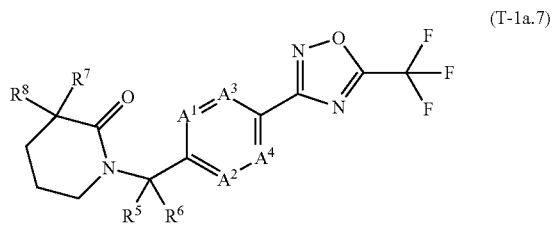
(T-1a.7)

Table 8a: This table discloses compounds 8a.001 to 8a.046 of the formula (T-1a.8), which is a compound of formula (I) wherein $R^6$ is H and $A^1, A^2, A^3, A^4, R^5, R^7$ and $R^8$ have the specific meanings given in the Table 1a.

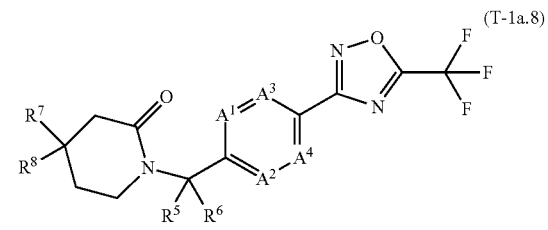
(T-1a.8)

Table 9a: This table discloses compounds 9a.001 to 9a.046 of the formula (T-1a.9), which is a compound of formula (I) wherein $R^6$ is H and $A^1, A^2, A^3, A^4, R^5, R^7$ and $R^8$ have the specific meanings given in the Table 1a.

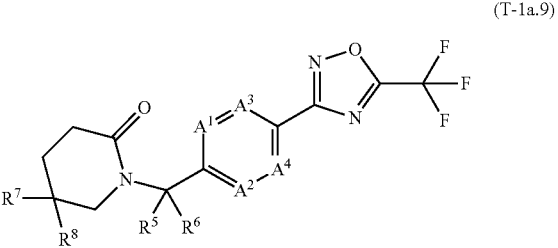
(T-1a.9)

Table 10a: This table discloses compounds 10a.001 to 10a.046 of the formula (T-1a.10), which is a compound of formula (I) wherein $R^6$ is H and $A^1, A^2, A^3, A^4, R^5, R^7$ and $R^8$ have the specific meanings given in the Table 1a.

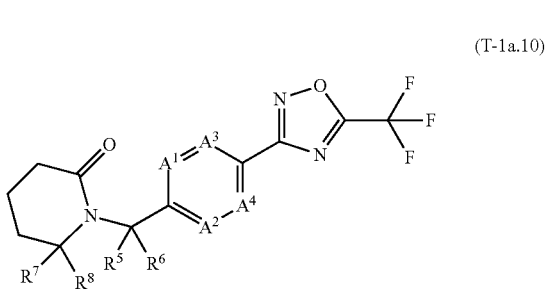
(T-1a.10)

Table 11a: This table discloses compounds 11a.001 to 11a.046 of the formula (T-1a.11), which is a compound of formula (I) wherein $R^6$ is H and $A^1, A^2, A^3, A^4, R^5, R^7$ and $R^8$ have the specific meanings given in the Table 1a.

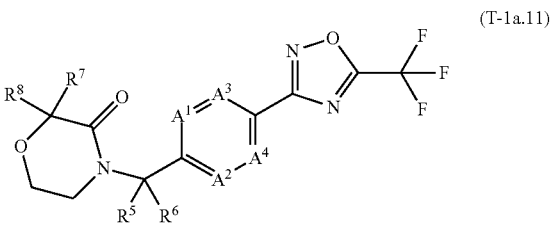
(T-1a.11)

Table 12a: This table discloses compounds 12a.001 to 12a.046 of the formula (T-1a.12), which is a compound of formula (I) wherein $R^6$ is H and $A^1, A^2, A^3, A^4, R^5, R^7$ and $R^8$ have the specific meanings given in the Table 1a.

(T-1a.12)

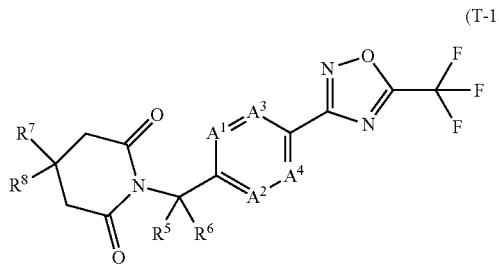

(T-1a.16)

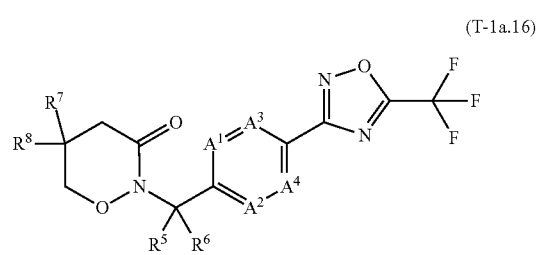

Table 13a: This table discloses compounds 13a.001 to 13a.046 of the formula (T-1a.13), which is a compound of formula (I) wherein $R^6$ is H and $A^1$, $A^2$, $A^3$, $A^4$, $R^5$, $R^7$ and $R^8$ have the specific meanings given in the Table 1a.

Table 17a: This table discloses compounds 17a.001 to 17a.046 of the formula (T-1a.17), which is a compound of formula (I) wherein $R^6$ is H and $A^1$, $A^2$, $A^3$, $A^4$, $R^5$, $R^7$ and $R^8$ have the specific meanings given in the Table 1a.

(T-1a.13)

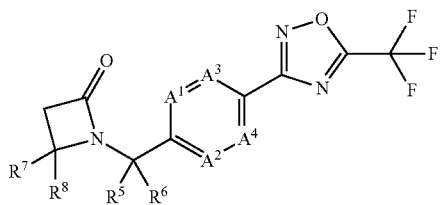

(T-1a.17)

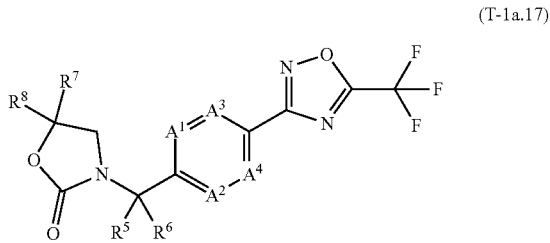

Table 14a: This table discloses compounds 14a.001 to 14a.046 of the formula (T-1a.14), which is a compound of formula (I) wherein $R^6$ is H and $A^1$, $A^2$, $A^3$, $A^4$, $R^5$, $R^7$ and $R^8$ have the specific meanings given in the Table 1.

Table 18a: This table discloses compounds 18a.001 to 18a.046 of the formula (T-1a.18), which is a compound of formula (I) wherein $R^6$ is H and $A^1$, $A^2$, $A^3$, $A^4$, $R^5$, $R^7$ and $R^8$ have the specific meanings given in the Table 1a.

(T-1a.14)

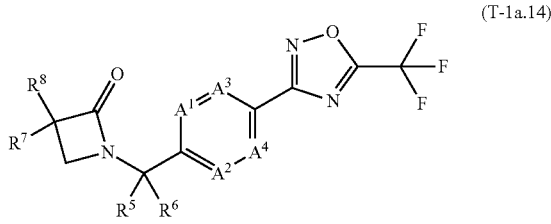

(T-1a.18)

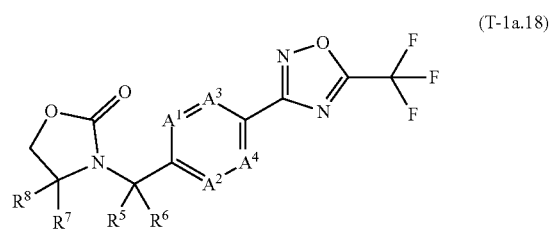

Table 15a: This table discloses compounds 15a.001 to 15a.046 of the formula (T-1a.15), which is a compound of formula (I) wherein $R^6$ is H and $A^1$, $A^2$, $A^3$, $A^4$, $R^5$, $R^7$ and $R^8$ have the specific meanings given in the Table 1a.

Table 19a: This table discloses compounds 19a.001 to 19a.046 of the formula (T-1a.19), which is a compound of formula (I) wherein $R^6$ is H and $A^1$, $A^2$, $A^3$, $A^4$, $R^5$, $R^7$ and $R^8$ have the specific meanings given in the Table 1a.

(T-1a.15)

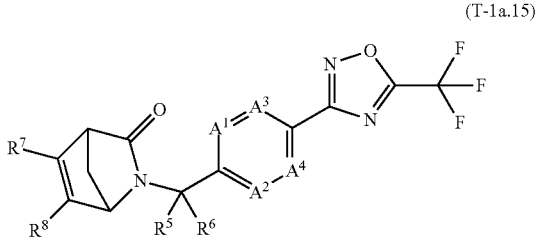

(T-1a.19)

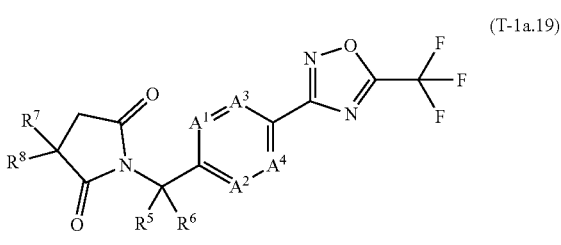

Table 16a: This table discloses compounds 16a.001 to 16a.046 of the formula (T-1a.16), which is a compound of formula (I) wherein $R^6$ is H and $A^1$, $A^2$, $A^3$, $A^4$, $R^5$, $R^7$ and $R^8$ have the specific meanings given in the Table 1a.

Table 20a: This table discloses compounds 20a.001 to 20a.046 of the formula (T-1a.20), which is a compound of formula (I) wherein $R^6$ is H and $A^1$, $A^2$, $A^3$, $A^4$, $R^5$, $R^7$ and $R^8$ have the specific meanings given in the Table 1a.

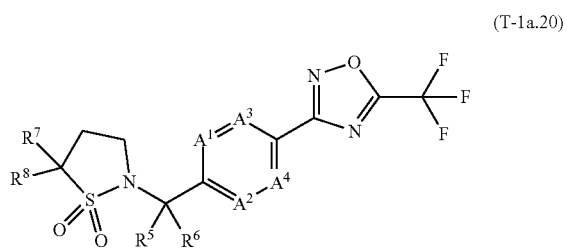
(T-1a.20)

Table 21a: This table discloses compounds 21a.001 to 21a.046 of the formula (T-1a.21), which is a compound of formula (I) wherein $R^6$ is H and $A^1$, $A^2$, $A^3$, $A^4$, $R^5$, $R^7$ and $R^8$ have the specific meanings given in the Table 1a.

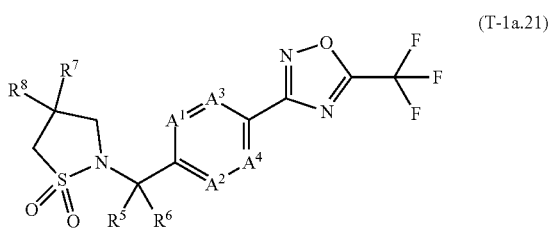
(T-1a.21)

Table 22a: This table discloses compounds 22a.001 to 22a.046 of the formula (T-1a.22), which is a compound of formula (I) wherein $R^6$ is H and $A^1$, $A^2$, $A^3$, $A^4$, $R^5$, $R^7$ and $R^8$ have the specific meanings given in the Table 1a.

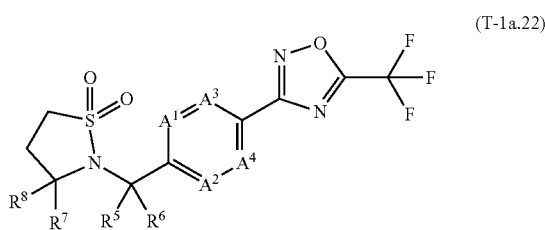
(T-1a.22)

Table 1b (below) discloses 138 combinations (compounds 1b.001 to 1 b.138) of $A^1$, $A^2$, $A^3$, $A^4$, $R^5$, $R^7$, $R^8$ and $R^9$ substituents in accordance with compounds as defined for Formula (T-1), wherein heterocycle Z contains a $NR^9$ ring member. Formula (T-1) corresponds to Formula (I) as defined for the present invention.

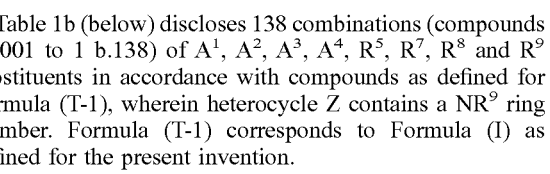
(T-1)

Each of Tables 2b to 4b (which follow Table 1b) make available 138 additional individual compounds of the formula (T-1) in which Z and $R^6$ are as specifically defined in Tables 2b to 4b (Formulae T-1b.2 to T-1b.4), which refer to Table 1b wherein $A^1$, $A^2$, $A^3$, $A^4$, $R^5$, $R^7$, $R^8$ and $R^9$ are specifically defined.

TABLE 1b

| Compound no. | $A^1$ | $A^2$ | $A^3$ | $A^4$ | $R^5$ | $R^7$ | $R^8$ | $R^9$ |
|---|---|---|---|---|---|---|---|---|
| 1b.001 to 1b.046 | Represents the 46 substitution patterns described in Table 1a | | | | | | | H |
| 1b.047 to 1b.092 | Represents the 46 substitution patterns described in Table 1a | | | | | | | Me |
| 1b.093 to 1b.138 | Represents the 46 substitution patterns described in Table 1a | | | | | | | OMe |

Table 2b: This table discloses compounds 2b.001 to 2b.138 of the formula (T-1b.2), which is a compound of formula (I) wherein $R^6$ is H and $A^1$, $A^2$, $A^3$, $A^4$, $R^5$, $R^7$, $R^8$ and $R^9$ have the specific meanings given in the Table 1b.

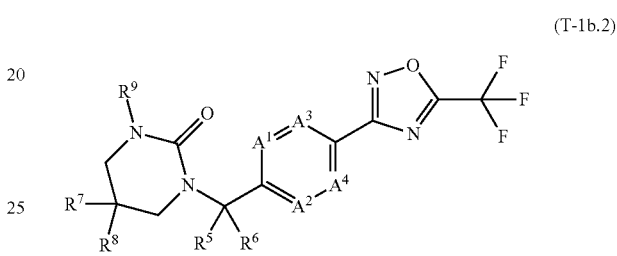
(T-1b.2)

Table 3b: This table discloses compounds 3b.001 to 3b.138 of the formula (T-1b.3), which is a compound of formula (I) wherein $R^6$ is H and $A^1$, $A^2$, $A^3$, $A^4$, $R^5$, $R^7$, $R^8$ and $R^9$ have the specific meanings given in the Table 1b.

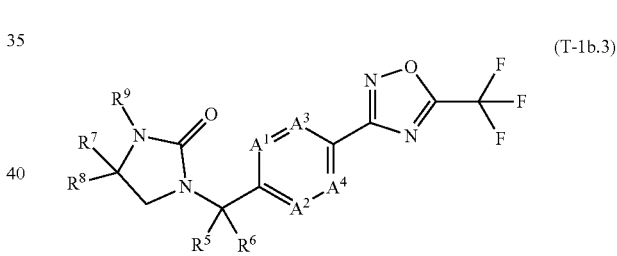
(T-1b.3)

Table 4b: This table discloses compounds 4b.001 to 4b.138 of the formula (T-1b.4), which is a compound of formula (I) wherein $R^6$ is H and $A^1$, $A^2$, $A^3$, $A^4$, $R^5$, $R^7$, $R^8$ and $R^9$ have the specific meanings given in the Table 1b.

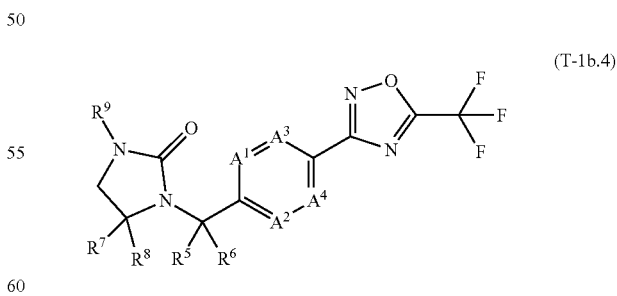
(T-1b.4)

Table 1c (below) discloses 690 combinations (compounds 1c.001 to 1c.690) of $A^1$, $A^2$, $A^3$, $A^4$, $R^5$, $R^7$, $R^8$, $R^9$, $R^{10}$ and $R^{11}$ substituents in accordance with compounds as defined for Formula (T-1), wherein heterocycle Z contains a $NR^9$ ring member. Formula (T-1) corresponds to Formula (I) as defined for the present invention.

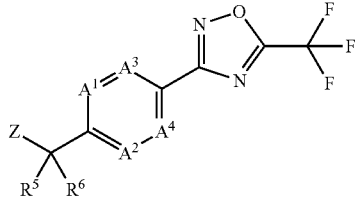

(T-1)

Table 2c (which follows Table 1c) makes available 690 additional individual compounds of the formula (T-1) in which Z and $R^6$ are as specifically defined in Table 2c (Formula T-1c.2), which refers to Table 1c wherein $A^1$, $A^2$, $A^3$, $A^4$, $R^5$, $R^7$, $R^8$, $R^9$, $R^{10}$ and $R^{11}$ are specifically defined.

in accordance with compounds as defined for Formula (T-2). Formula (T-2) corresponds to Formula (I) as defined for the present invention.

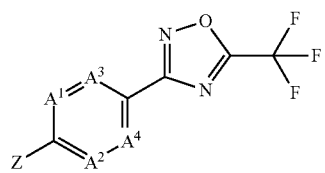

(T-2)

Each of Tables 2d to 13d (which follow Table 1d) make available 30 additional individual compounds of the formula TABLE 1c

| Compound no. | $A^1$ | $A^2$ | $A^3$ | $A^4$ | $R^5$ | $R^7$ | $R^8$ | $R^9$ | $R^{10}$ |
|---|---|---|---|---|---|---|---|---|---|
| 1c.001 to 1c.046 | Represents the 46 substitution patterns described in Table 1a for $A^1$, $A^2$, $A^3$, $A^4$, $R^5$, $R^7$ and $R^8$ | | | | | | | C(O)$R^{10}$ | H |
| 1c.047 to 1c.092 | Represents the 46 substitution patterns described in Table 1a for $A^1$, $A^2$, $A^3$, $A^4$, $R^5$, $R^7$ and $R^8$ | | | | | | | C(O)$R^{10}$ | $CH_3$ |
| 1c.093 to 1c.138 | Represents the 46 substitution patterns described in Table 1a for $A^1$, $A^2$, $A^3$, $A^4$, $R^5$, $R^7$ and $R^8$ | | | | | | | C(O)O$R^{10}$ | $CH_3$ |
| 1c.139 to 1c.184 | Represents the 46 substitution patterns described in Table 1a for $A^1$, $A^2$, $A^3$, $A^4$, $R^5$, $R^7$ and $R^8$ | | | | | | | C(O)O$R^{10}$ | $CH_2CH_3$ |
| 1c.185 to 1c.230 | Represents the 46 substitution patterns described in Table 1a for $A^1$, $A^2$, $A^3$, $A^4$, $R^5$, $R^7$ and $R^8$ | | | | | | | C(O)N(H)$R^{10}$ | H |
| 1c.231 to 1c.276 | Represents the 46 substitution patterns described in Table 1a for $A^1$, $A^2$, $A^3$, $A^4$, $R^5$, $R^7$ and $R^8$ | | | | | | | C(O)N(H)$R^{10}$ | $CH_3$ |
| 1c.277 to 1c.322 | Represents the 46 substitution patterns described in Table 1a for $A^1$, $A^2$, $A^3$, $A^4$, $R^5$, $R^7$ and $R^8$ | | | | | | | C(O)N(Me)$R^{10}$ | $CH_3$ |
| 1c.323 to 1c.368 | Represents the 46 substitution patterns described in Table 1a for $A^1$, $A^2$, $A^3$, $A^4$, $R^5$, $R^7$ and $R^8$ | | | | | | | C(O)N(Et)$R^{10}$ | H |
| 1c.369 to 1c.414 | Represents the 46 substitution patterns described in Table 1a for $A^1$, $A^2$, $A^3$, $A^4$, $R^5$, $R^7$ and $R^8$ | | | | | | | C(O)N(Et)$R^{10}$ | $CH_3$ |
| 1c.415 to 1c.460 | Represents the 46 substitution patterns described in Table 1a for $A^1$, $A^2$, $A^3$, $A^4$, $R^5$, $R^7$ and $R^8$ | | | | | | | C(O)N(OMe)$R^{10}$ | H |
| 1c.461 to 1c.506 | Represents the 46 substitution patterns described in Table 1a for $A^1$, $A^2$, $A^3$, $A^4$, $R^5$, $R^7$ and $R^8$ | | | | | | | C(O)N(OMe)$R^{10}$ | $CH_3$ |
| 1c.507 to 1c.552 | Represents the 46 substitution patterns described in Table 1a for $A^1$, $A^2$, $A^3$, $A^4$, $R^5$, $R^7$ and $R^8$ | | | | | | | $SO_2R^{10}$ | $CH_3$ |
| 1c.553 to 1c.598 | Represents the 46 substitution patterns described in Table 1a for $A^1$, $A^2$, $A^3$, $A^4$, $R^5$, $R^7$ and $R^8$ | | | | | | | $SO_2$N(H)$R^{10}$ | H |
| 1c.599 to 1c.644 | Represents the 46 substitution patterns described in Table 1a for $A^1$, $A^2$, $A^3$, $A^4$, $R^5$, $R^7$ and $R^8$ | | | | | | | $SO_2$N(H)$R^{10}$ | $CH_3$ |
| 1c.645 to 1c.690 | Represents the 46 substitution patterns described in Table 1a for $A^1$, $A^2$, $A^3$, $A^4$, $R^5$, $R^7$ and $R^8$ | | | | | | | $SO_2$N($CH_3$)$R^{10}$ | $CH_3$ |

Table 2c: This table discloses compounds 2c.001 to 2c.690 of the formula (T-1c.2), which is a compound of formula (I) wherein $R^6$ is H and $A^1$, $A^2$, $A^3$, $A^4$, $R^5$, $R^7$, $R^8$, $R^9$, $R^{10}$ and $R^{11}$ have the specific meanings given in the Table 1c.

(T-1c.2)

Table 1d (below) discloses 30 combinations (compounds 1d.001 to 1d.030) of $A^1$, $A^2$, $A^3$, $A^4$, $R^7$ and $R^8$ substituents (T-2) in which Z is as specifically defined in Tables 2d to 13d (Formulae T-2d.2 to T-2d.13), which refer to Table 1d wherein $A^1$, $A^2$, $A^3$, $A^4$, $R^7$ and $R^8$ are specifically defined.

TABLE 1d

| Compound no. | $A^1$ | $A^2$ | $A^3$ | $A^4$ | $R^7$ | $R^8$ |
|---|---|---|---|---|---|---|
| 1d.001 | C—H | C—H | C—H | C—H | H | H |
| 1d.002 | C—H | C—H | C—H | C—H | H | $CH_3$ |
| 1d.003 | C—H | C—H | C—H | C—H | $CH_3$ | $CH_3$ |
| 1d.004 | C—F | C—H | C—H | C—H | H | H |
| 1d.005 | C—F | C—H | C—H | C—H | H | $CH_3$ |
| 1d.006 | C—F | C—H | C—H | C—H | $CH_3$ | $CH_3$ |
| 1d.007 | C—$CH_3$ | C—H | C—H | C—H | H | H |
| 1d.008 | C—$CH_3$ | C—H | C—H | C—H | H | $CH_3$ |
| 1d.009 | C—$CH_3$ | C—H | C—H | C—H | $CH_3$ | $CH_3$ |
| 1d.010 | N | C—H | C—H | C—H | H | H |
| 1d.011 | N | C—H | C—H | C—H | H | $CH_3$ |
| 1d.012 | N | C—H | C—H | C—H | $CH_3$ | $CH_3$ |
| 1d.013 | C—Cl | C—H | C—H | C—H | H | H |

TABLE 1d-continued

| Compound no. | A¹ | A² | A³ | A⁴ | R⁷ | R⁸ |
|---|---|---|---|---|---|---|
| 1d.014 | C—Cl | C—H | C—H | C—H | H | CH₃ |
| 1d.015 | C—Cl | C—H | C—H | C—H | CH₃ | CH₃ |
| 1d.016 | C—OCH₃ | C—H | C—H | C—H | H | H |
| 1d.017 | C—OCH₃ | C—H | C—H | C—H | H | CH₃ |
| 1d.018 | C—OCH₃ | C—H | C—H | C—H | CH₃ | CH₃ |
| 1d.019 | C—CF₃ | C—H | C—H | C—H | H | H |
| 1d.020 | C—CF₃ | C—H | C—H | C—H | H | CH₃ |
| 1d.021 | C—CF₃ | C—H | C—H | C—H | CH₃ | CH₃ |
| 1d.022 | C—H | C—H | C—F | C—H | H | H |
| 1d.023 | C—H | C—H | C—F | C—H | H | CH₃ |
| 1d.024 | C—H | C—H | C—F | C—H | CH₃ | CH₃ |
| 1d.025 | C—H | C—H | N | C—H | H | H |
| 1d.026 | C—H | C—H | N | C—H | H | CH₃ |
| 1d.027 | C—H | C—H | N | C—H | CH₃ | CH₃ |
| 1d.028 | N | N | C—H | C—H | H | H |
| 1d.029 | N | N | C—H | C—H | H | CH₃ |
| 1d.030 | N | N | C—H | C—H | CH₃ | CH₃ |

Table 2d: This table discloses compounds 2d.001 to 2d.030 of the formula (T-2d.2), which is a compound of formula (I) wherein A¹, A², A³, A⁴, R⁷ and R⁸ have the specific meanings given in the Table 1d.

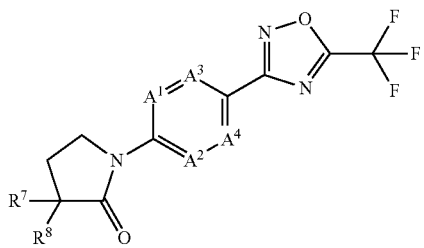

(T-2d.2)

Table 3d: This table discloses compounds 3d.001 to 3d.030 of the formula (T-2d.3), which is a compound of formula (I) wherein A¹, A², A³, A⁴, R⁷ and R⁸ have the specific meanings given in the Table 1d.

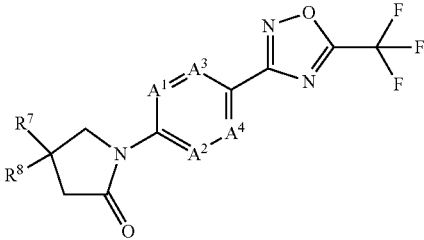

(T-2d.3)

Table 4d: This table discloses compounds 4d.001 to 4d.030 of the formula (T-2d.4), which is a compound of formula (I) wherein A¹, A², A³, A⁴, R⁷ and R⁸ have the specific meanings given in the Table 1d.

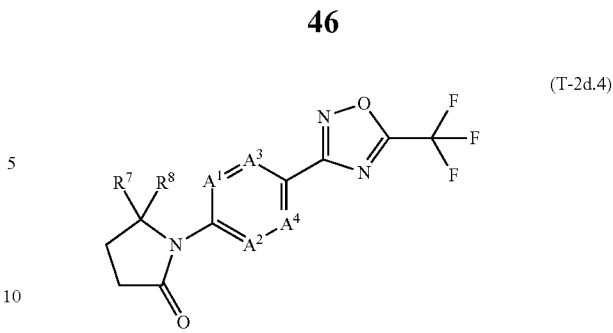

(T-2d.4)

Table 5d: This table discloses compounds 5d.001 to 5d.030 of the formula (T-2d.5), which is a compound of formula (I) wherein A¹, A², A³, A⁴, R⁵, R⁷ and R⁸ have the specific meanings given in the Table 1d.

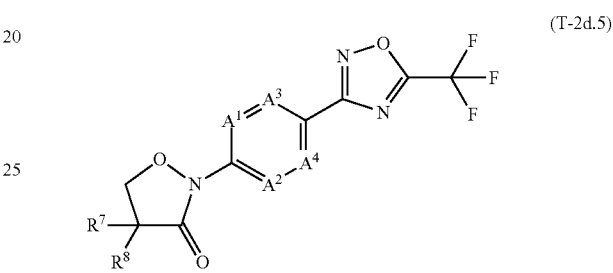

(T-2d.5)

Table 6d: This table discloses compounds 6d.001 to 6d.030 of the formula (T-2d.6), which is a compound of formula (I) wherein A¹, A², A³, A⁴, R⁷ and R⁸ have the specific meanings given in the Table 1d.

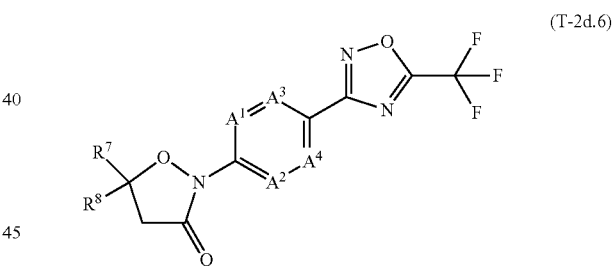

(T-2d.6)

Table 7d: This table discloses compounds 7d.001 to 7d.030 of the formula (T-2d.7), which is a compound of formula (I) wherein A¹, A², A³, A⁴, R⁷ and R⁸ have the specific meanings given in the Table 1d.

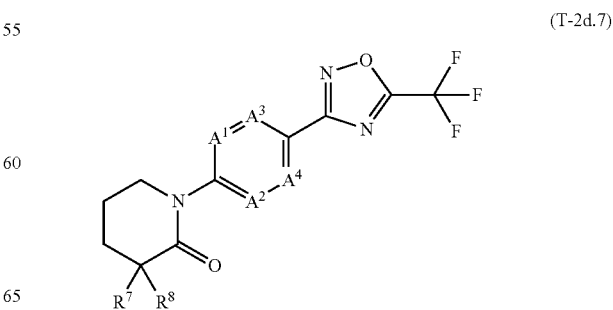

(T-2d.7)

Table 8d: This table discloses compounds 8d.001 to 8d.030 of the formula (T-2d.8), which is a compound of formula (I) wherein $A^1$, $A^2$, $A^3$, $A^4$, $R^7$ and $R^8$ have the specific meanings given in the Table 1d.

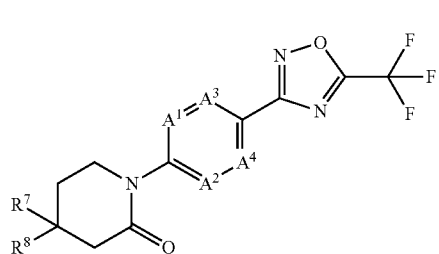
(T-2d.8)

Table 9d: This table discloses compounds 9d.001 to 9d.030 of the formula (T-2d.9), which is a compound of formula (I) wherein $A^1$, $A^2$, $A^3$, $A^4$, $R^7$ and $R^8$ have the specific meanings given in the Table 1d.

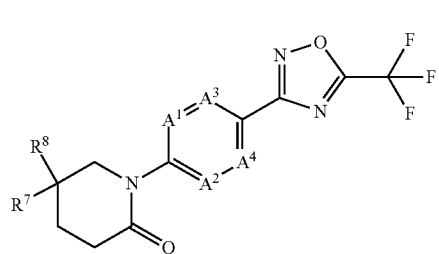
(T-2d.9)

Table 10d: This table discloses compounds 10d.001 to 10d.030 of the formula (T-2d.10), which is a compound of formula (I) wherein $A^1$, $A^2$, $A^3$, $A^4$, $R^7$ and $R^8$ have the specific meanings given in the Table 1d.

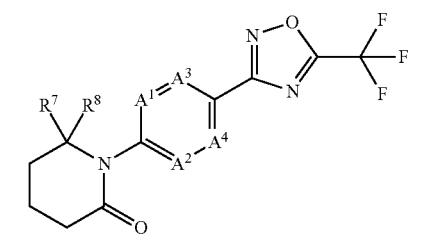
(T-2d.10)

Table 11d: This table discloses compounds 11d.001 to 11d.030 of the formula (T-2d.11), which is a compound of formula (I) wherein $A^1$, $A^2$, $A^3$, $A^4$, $R^7$ and $R^8$ have the specific meanings given in the Table 1d.

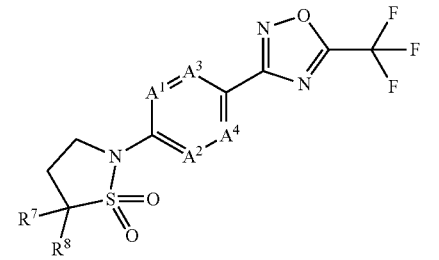
(T-2d.11)

Table 12d: This table discloses compounds 12d.001 to 12d.030 of the formula (T-2d.12), which is a compound of formula (I) wherein $A^1$, $A^2$, $A^3$, $A^4$, $R^7$ and $R^8$ have the specific meanings given in the Table 1d.

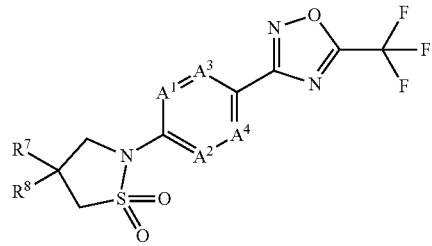
(T-2d.12)

Table 13d: This table discloses compounds 13d.001 to 13d.030 of the formula (T-2d.13), which is a compound of formula (I) wherein $A^1$, $A^2$, $A^3$, $A^4$, $R^7$ and $R^8$ have the specific meanings given in the Table 1d.

(T-2d.13)

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, temperatures are given in degrees Celsius (° C.) and "mp." means melting point. LC/MS means Liquid Chromatography Mass Spectrometry and the description of the apparatus and the method is as follows:

The Description of the LC/MS Apparatus and the Method A is:

SQ Detector 2 from Waters

Ionisation method: Electrospray

Polarity: positive and negative ions

Capillary (kV) 3.0, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650

Mass range: 100 to 900 Da

DAD Wavelength range (nm): 210 to 500

Method Waters ACQUITY UPLC with the following HPLC gradient conditions:
(Solvent A: Water/Methanol 20:1+0.05% formic acid and Solvent B: Acetonitrile+0.05% formic acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.
The Description of the LC/MS Apparatus and the Method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the following HPLC gradient conditions
(Solvent A: Water/Methanol 9:1+0.1% formic acid and Solvent B: Acetonitrile+0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
The Description of the LC/MS Apparatus and the Method C is:
SQ Detector 2 from Waters
Ionisation method: Electrospray
ACQUITY H Class UPLC, Mass Spectrometer from Waters
Polarity: positive and Negative Polarity Switch
Scan Type MS1 Scan
Capillary (kV) 3.00, Cone (V) 40.00, Desolvation Temperature (° C.) 500, Cone Gas Flow (L/Hr) 50, Desolvation Gas Flow (L/Hr) 1000
Mass range: 0 to 2000 Da
DAD Wavelength range (nm): 200 to 350
Method Waters ACQUITY UPLC with the following HPLC gradient conditions
(Solvent A: Water+0.1% formic acid and Solvent B: Acetonitrile)

| Time (minutes) | A (%) | B (%) | Flow rate (ml/min) |
|---|---|---|---|
| 0 | 70 | 30 | 0.5 |
| 0.05 | 70 | 30 | 0.5 |
| 0.8 | 5 | 95 | 0.5 |
| 1.8 | 5 | 95 | 0.5 |
| 2.45 | 70 | 30 | 0.5 |
| 2.50 | 70 | 30 | 0.5 |

Type of column: Waters ACQUITY UPLC BEH $C_{18}$; Column length: 50 mm; Internal diameter of column: 2.1 mm; Particle Size: 1.7 micron; Temperature: 35° C.

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (1)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

LIST OF ABBREVIATIONS

AIBN=azobisisobutyronitrile
DMF=dimethylformamide
DIPEA=N,N-di-isopropylethylamine
EtOAc=ethyl acetate
KHMDS=potassium bis(trimethylsilyl)amide
HCl=hydrochloric acid
mp=melting point
° C.=degrees Celsius
MeOH=methyl alcohol
NaOH=sodium hydroxide
NBS=N-bromosuccinimide
min=minutes
RT=room temperature
TFAA=trifluoroacetic acid anhydride
THF=tetrahydrofuran
$t_R$=Retention time
LC/MS=Liquid Chromatography Mass Spectrometry (description of the apparatus and the methods used for LC/MS analysis are given above)

PREPARATION EXAMPLES

Example 1: This Example Illustrates the Preparation 2-[[4-[5-(trifluoromethyl)-1,2,4-oxadiazol-3-yl]phenyl]methyl]isoxazolidin-3-one (Compound A-5 of Table A)

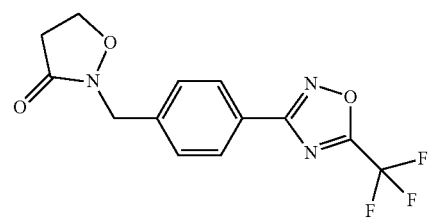 [SMILES: O=C1CCON1Cc1ccc(-c2noc(C(F)(F)F)n2)cc1]

Step 1: Preparation of N'-hydroxy-4-methyl-benzamidine

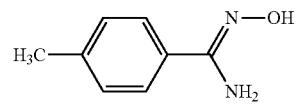

To a stirred suspension of 4-methylbenzonitrile (35 g, 0.29 mol) in ethanol (220 mL) and water (440 mL) at RT was added hydroxylamine hydrochloride (41.1 g, 0.58 mol), potassium carbonate (65.4 g, 0.47 mol) and 8-hydroxyquinoline (0.22 g, 1.5 mmol). The reaction mixture was heated at 80° C. for 4 hours. The mixture was cooled to RT and diluted with 2N HCl until pH 8. Ethanol was evaporated under reduced pressure. The mixture was filtered, washed with water and dried under vacuum to afford the title compound. LC/MS (Method A) retention time=0.23 minutes, 151.0 (M+H).

Step 2: Preparation of 3-(p-tolyl)-5-(trifluoromethyl)-1,2,4-oxadiazole

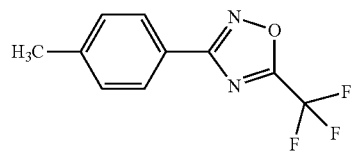 [SMILES: Cc1ccc(-c2noc(C(F)(F)F)n2)cc1]

To a stirred solution of N'-hydroxy-4-methyl-benzamine (38.7 g, 0.25 mol) in 2-methyltetrahydrofuran (750 mL) was added TFAA at 0° C. The reaction mixture was stirred at 15° C. for two hours and then diluted with water. The organic layer was separated, washed successively with sodium bicarbonate solution, ammonium chloride solution and water, dried over sodium sulfate, filtered and evaporated to dryness. The crude product was purified by flash chromatography over silica gel (750 g pre-packed column) with heptane/EtOAc 99:1 to 90:10 to afford the title compound as a clear oil, which solidified upon storage.

LC/MS (Method A) retention time=1.15 minutes, mass not detected.

$^1$H NMR (400 MHz, CDCl$_3$) δ ppm: 8.00 (d, 2H), 7.32 (d, 2H), 2.45 (s, 3H).

$^{19}$F NMR (400 MHz, CDCl$_3$) δ ppm: −65.41 (s).

Step 3a: Preparation of 3-[4-(bromomethyl)phenyl]-5-(trifluoromethyl)-1,2,4-oxadiazole

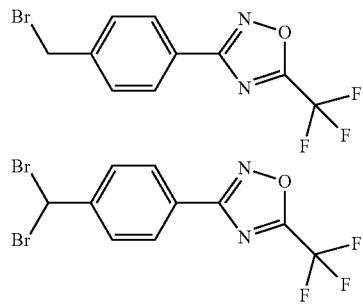

A stirred mixture of 3-(p-tolyl)-5-(trifluoromethyl)-1,2,4-oxadiazole (56.0 g, 0.24 mol) and NBS (45.4 g, 0.25 mol) in tetrachloromethane (480 mL) under argon was heated to 70° C. AIBN (4.03 g, 24 mmol) was added and the reaction mixture stirred at 65° C. for 18 hours. The mixture was cooled to RT and diluted with dichloromethane and water. Layers were separated. The organic layer was washed with a sodium bicarbonate solution, dried over sodium sulfate, filtered and evaporated to dryness. The crude residue was purified by flash chromatography over silica gel (750 g pre-packed column) with cyclohexane/EtOAc 100:0 to 95:5 to afford the title compound as a white solid mp: 58-63° C.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

3-[4-(dibromomethyl)phenyl]-5-(trifluoromethyl)-1,2,4-oxadiazole was isolated as by-product as a white solid mp: 61-66° C.

$^1$H NMR (400 MHz, CDCl$_3$) δ ppm: 8.15 (d, 2H), 7.73 (d, 2H), 6.68 (s, 1H).

$^{19}$F NMR (400 MHz, CDCl$_3$) δ ppm: −65.34 (s).

Step 3b: Preparation of 3-[4-(bromomethyl)phenyl]-5-(trifluoromethyl)-1,2,4-oxadiazole from 3-[4-(dibromomethyl)phenyl]-5-(trifluoromethyl)-1,2,4-oxadiazole

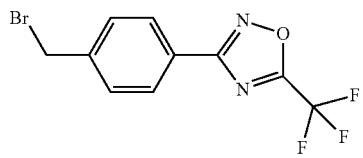 [SMILES: FC(F)(F)c1nc(-c2ccc(CBr)cc2)no1]

To a stirred 1:9 ratio mixture of 3-[4-(bromomethyl)phenyl]-5-(trifluoromethyl)-1,2,4-oxadiazole and 3-[4-(dibromomethyl)phenyl]-5-(trifluoromethyl)-1,2,4-oxadiazole (10.2 g) in acetonitrile (95 mL), water (1.9 mL) and DIPEA (6.20 ml, 35.7 mmol) was added diethylphosphite (4.7 mL, 35.7 mmol) at 5° C. The mixture was stirred at 5-10° C. for two hours, water and 1M HCl were added and acetonitrile was evaporated under reduced pressure. The white slurry was extracted three times with dichloromethane. The combined organic layers were dried over sodium sulfate, and filtered. The solvent was removed under reduced pressure and the resultant crude residue was purified by flash chromatography over silica gel (40 g pre-packed column) with cyclohexane/EtOAc 99:1 to 9:1 to afford 3-[4-(bromomethyl)phenyl]-5-(trifluoromethyl)-1,2,4-oxadiazole.

$^1$H NMR (400 MHz, CDCl$_3$) δ ppm: 8.11 (d, 2H), 7.55 (d, 2H), 4.53 (s, 2H).

$^{19}$F NMR (400 MHz, CDCl$_3$) δ ppm: −65.32 (s).

Step 4: Preparation of 2-[[4-[5-(trifluoromethyl)-1,2,4-oxadiazol-3-yl]phenyl]methyl]isoxazolidin-3-one

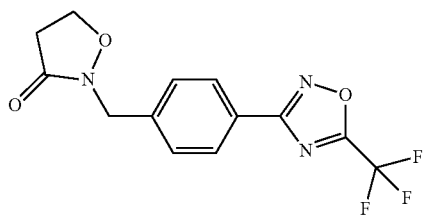 [SMILES: O=C1CCON1Cc1ccc(-c2noc(C(F)(F)F)n2)cc1]

A solution of 3-[4-(bromomethyl)phenyl]-5-(trifluoromethyl)-1,2,4-oxadiazole (150 mg, 0.46 mmol), isoxazolidin-3-one (1.5 equiv., 61 mg, 0.7 mmol), and potassium carbonate (2 equiv., 130 mg, 0.93 mmol) in acetonitrile (4.7 mL) was heated in a microwave oven for 30 minutes at 120° C. Solids were removed by filtration and washed with ethyl acetate and the mother liquors evaporated to give a crude residue which was purified by flash chromatography over silica gel (cyclohexane:EtOAc eluent gradient 1:0 to 1:1) to afford the title compound as a yellow solid. LC/MS (Method A) retention time=0.96 minutes, 314 (M+H). mp: 54-58° C.

$^1$H NMR (400 MHz, CDCl$_3$) δ ppm: 8.22 (d, 2H), 7.49 (d, 2H), 4.75 (s, 2H), 4.30 (t, 2H), 2.80 (t, 3H)

Example 2: This Example Illustrates the Preparation of 4,4-dimethyl-1-[[4-[5-(trifluoromethyl)-1,2,4-oxadiazol-3-yl]phenyl]methyl]piperidine-2,6-dione (Compound A-11 of Table A)

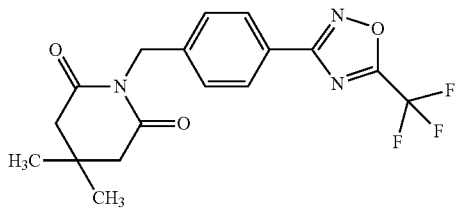 [SMILES: CC1(C)CC(=O)N(Cc2ccc(-c3noc(C(F)(F)F)n3)cc2)C(=O)C1]

To a stirred solution of n-BuLi in hexanes (1.6 M, 0.285 mL, 0.456 mmol) and THF (1.1 mL) at −78° C. was added a solution of 4,4-dimethylpiperidine-2,6-dione (0.055 g, 0.39 mmol) in THF (0.3 mL). The reaction mixture was stirred for 30 minutes at −78° C. and then 3-[4-(bromomethyl)phenyl]-5-(trifluoromethyl)-1,2,4-oxadiazole (0.100 g, 0.326 mmol) was added. The reaction mixture was then warmed to 0° C. and stirred at this temperature for 1 h. The reaction mixture was further warmed to RT and stirred overnight before being quenched at 0° C. with a saturated NH$_4$Cl solution. The mixture was extracted with ethyl acetate and the combined organic layers washed with brine, dried over Na$_2$SO$_4$, filtered and concentrated. The residue obtained was purified by flash chromatography over silica gel using cyclohexane/AcOEt as eluent to give 4,4-dimethyl-1-[[4-[5-(trifluoromethyl)-1,2,4-oxadiazol-3-yl]phenyl]methyl]piperidine-2,6-dione as a colorless oil. LC/MS (Method A) retention time=1.14 minutes, 368 (M+H).

$^1$H NMR (400 MHz, CDCl$_3$) δ ppm 0.96-1.04 (s, 6H) 2.48 (s, 4H) 4.95 (s, 2H) 7.45 (d, 2H) 7.97 (d, 2H)

Example 3: This Example Illustrates the Preparation of 4-[[4-[5-(trifluoromethyl)-1,2,4-oxadiazol-3-yl]phenyl]methyl]morpholin-3-one (Compound A-3 of Table A)

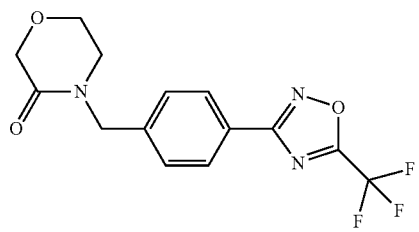 [SMILES: O=C1COCCN1Cc1ccc(-c2noc(C(F)(F)F)n2)cc1]

Step 1: 4-[(3-oxomorpholin-4-yl)methyl]benzonitrile

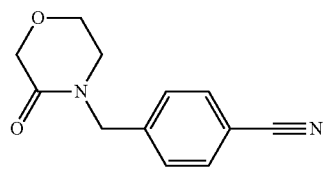 [SMILES: N#Cc1ccc(CN2CCOCC2=O)cc1]

A solution of 4-(bromomethyl)benzonitrile (2.0 g, 10.2 mmol), morpholin-3-one (2.5 equiv., 2.11 g, 20.9 mmol), and potassium carbonate (2 equiv., 2.82 g, 20.4 mmol) in acetonitrile (4.7 mL) was heated at 85° C. for 19 hours. After cooling to 25° C., the solvent was removed under reduced pressure. The residue obtained was dissolved in ethyl acetate and washed with water. The organic layer was then dried over sodium sulfate, and concentrated under reduced pressure. The crude yellow residue obtained was purified by flash chromatography over silica gel (cyclohexane:EtOAc eluent gradient 9:1 to 0:1) to give 1.13 g (51% yield) of the title compound as a yellow oil. LC/MS (Method A) retention time=0.58 minutes, 217 (M+H).

$^1$H NMR (400 MHz, CDCl$_3$) δ ppm: 7.65 (d, 2H), 7.38 (d, 2H), 4.68 (s, 2H), 4.25 (t, 2H), 3.85 (t, 2H), 3.30 (t, 2H).

Step 2: N-hydroxy-4-[(3-oxomorpholin-4-yl)methyl]benzamidine

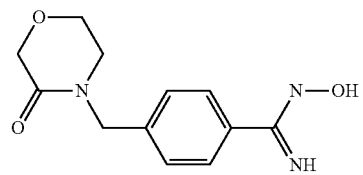 [SMILES: N=C(NO)c1ccc(CN2CCOCC2=O)cc1]

In a flask under argon, to hydroxylamine hydrochloride (3.0 equiv., 1.09 g 15.7 mmol) and ethanol (10.5 mL) was added triethylamine (3.0 equiv., 2.19 mL, 15.7 mol) at 25° C. The resultant suspension was allowed to stir for 30 minutes after which 4-[(3-oxomorpholin-4-yl)methyl]benzonitrile (1.13 g, 5.23 mmol) was introduced and the reaction mixture heated at a temperature of 50° C. for 6 hours. Ethanol was evaporated under reduced pressure and the crude reaction mixture taken up in the next step without additional purification or characterization. LC/MS (Method A) retention time=0.23 minutes, 151.0 (M+H).

Step 3: 4-[[4-[5-(trifluoromethyl)-1,2,4-oxadiazol-3-yl]phenyl]methyl]morpholin-3-one

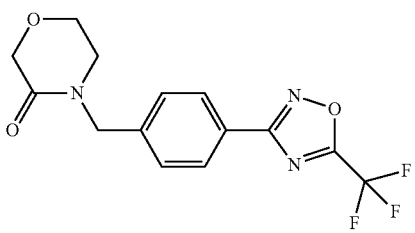 [SMILES: O=C1COCCN1Cc1ccc(-c2noc(C(F)(F)F)n2)cc1]

To a stirred solution of crude N-hydroxy-4-[(3-oxomorpholin-4-yl)methyl]benzamidine (5.23 mmol) in tetrahydrofuran (10 mL) was added drop-wise trifluoroacetic anhydride (1.5 equiv, 1.1 mL, 7.8 mmol) at 25° C. The solvent was removed under reduced pressure, affording an orange oil which was dissolved in a minimal amount of dichloromethane and then washed with a saturated aqueous sodium bicarbonate solution. The organic phase was dried over sodium sulfate, filtrated, and solvent was removed under vacuum. The crude residue was purified by combiflash chromatography over silica gel (heptane:EtOAc eluent gradient 99:1 to 90:10) to afford 850 mg (50% yield) of the title compound as colorless oil. LC/MS (Method A) retention time=0.92 minutes, 328 (M+H).

¹H NMR (400 MHz, CDCl₃) δ ppm: 8.10 (d, 2H), 7.45 (d, 2H), 4.70 (s, 2H), 4.37 (s, 2H), 3.85 (t, 2H), 3.30 (t, 2H).

¹⁹F NMR (400 MHz, CDCl₃) δ ppm: −65.33 (s).

Example 4: This Example Illustrates the Preparation of 1-[[5-[5-(trifluoromethyl)-1,2,4-oxadiazol-3-yl]-2-pyridyl]methyl]piperidin-2-one (Compound A-12 of Table A)

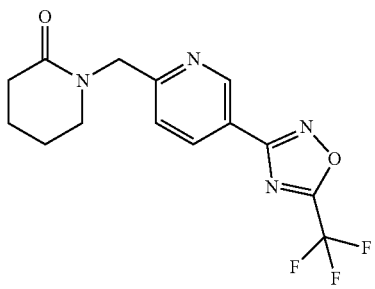 [SMILES: O=C1CCCCN1Cc1ccc(-c2noc(C(F)(F)F)n2)cn1]

Step 1:
N'-hydroxy-6-methyl-pyridine-3-carboxamidine

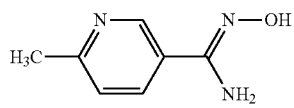

To a stirred suspension of 5-cyano-2-picoline (3.0 g, 25.4 mmol) in ethanol (86 mL) was added at RT hydroxylamine hydrochloride (5.2 g, 76.0 mmol) and triethylamine (10.6 g, 76.0 mmol). The reaction mixture was heated at 80° C. for 2 hours. The mixture was cooled to RT and the ethanol evaporated under reduced pressure. The mixture was filtered, washed with water and dried under vacuum to afford 3.8 g of the title compound used without further purification.

Step 2: Preparation of 3-(6-methyl-3-pyridyl)-5-(trifluoromethyl)-1,2,4-oxadiazole

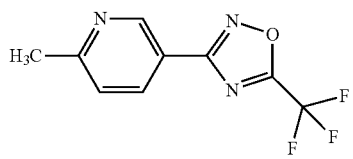 [SMILES: Cc1ccc(-c2noc(C(F)(F)F)n2)cn1]

To a stirred solution of N'-hydroxy-6-methyl-pyridine-3-carboxamidine (3.83 g, 25.3 mmol) in tetrahydrofuran (84 mL) was added TFAA (5.3 mL, 38 mmol) at 0° C. The reaction mixture was stirred at 15° C. for two hours and diluted with water. The organic layer was separated, washed successively with sodium bicarbonate solution, ammonium chloride solution and water, dried over sodium sulfate, filtered and evaporated to dryness to afford 5.8 g of the title compound as clear oil used without further purification.

LC/MS (Method A) retention time=0.97 minutes, 230 (M+H).

¹H NMR (400 MHz, CDCl₃) δ ppm: 9.23 (d, 2H), 8.26 (d, 2H), 7.35 (d, 2H), 2.66 (s, 3H).

¹⁹F NMR (400 MHz, CDCl₃) δ ppm: −65.3 (s).

Step 3a: Preparation of 3-[6-(bromomethyl)-3-pyridyl]-5-(trifluoromethyl)-1,2,4-oxadiazole

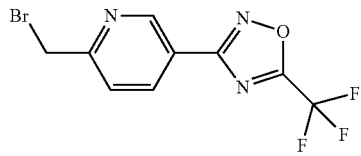

A stirred mixture of 3-(6-methyl-3-pyridyl)-5-(trifluoromethyl)-1,2,4-oxadiazole (2.2 g, 7.1 mmol) and NBS (3.5 g, 19.0 mmol) in tetrachloromethane (38 mL) under argon was heated to 70° C. AIBN (4.03 g, 24 mmol) was added portion-wise and the reaction mixture stirred at 65° C. for 18 hours. The mixture was cooled to 25° C. and diluted with dichloromethane and water. The organic layer was washed with a sodium bicarbonate solution, dried over sodium sulfate, filtered and evaporated to dryness. The crude residue was subjected to flash chromatography over silica gel with cyclohexane/EtOAc 100:0 to 80:20 to afford 2.2 g of the title compound as a white solid.

LC/MS (Method A) retention time=1.01 minutes, no mass detected

¹H NMR (400 MHz, CDCl₃) δ ppm: 9.25 (s, 1H), 8.40 (dd, 1H), 7.63 (d, 1H), 4.6 (s, 2H).

¹⁹F NMR (400 MHz, CDCl₃) δ ppm: −65.2 (s).

3-[6-(dibromomethyl)-3-pyridyl]-5-(trifluoromethyl)-1,2,4-oxadiazole (see below) was isolated as by-product as a beige oil in 44% yield (3.2 g, containing ca. 10% of 3-[6-(bromomethyl)-3-pyridyl]-5-(trifluoromethyl)-1,2,4-oxadiazole).

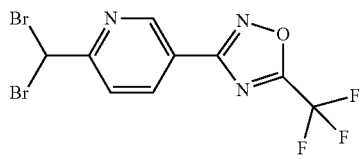 [SMILES: FC(F)(F)c1nc(-c2ccc(C(Br)Br)nc2)no1]

LC/MS (Method A) retention time=1.10 minutes, 388 (M+H).

¹H NMR (400 MHz, CDCl₃) δ ppm: 9.25 (s, 1H), 8.50 (dd, 1H), 7.98 (d, 1H), 6.71 (s, 1H).

¹⁹F NMR (400 MHz, CDCl₃) δ ppm: −65.2 (s).

Step 3b: Preparation of 3-[6-(bromomethyl)-3-pyridyl]-5-(trifluoromethyl)-1,2,4-oxadiazole

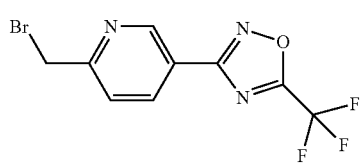 [SMILES: FC(F)(F)c1nc(-c2ccc(CBr)nc2)no1]

To a stirred 1:9 ratio mixture of 3-[6-(bromomethyl)-3-pyridyl]-5-(trifluoromethyl)-1,2,4-oxadiazole and 3-[6-(dibromomethyl)-3-pyridyl]-5-(trifluoromethyl)-1,2,4-oxadiazole (3.24 g, 8.4 mmol) in acetonitrile (35 mL), water (0.7 mL) and DIPEA (2.2 ml, 12.6 mmol) was added diethylphosphite (1.65 ml, 12.6 mmol) at 5° C. The mixture was stirred at 5-10° C. for two hours, water and 1M HCl were added, and acetonitrile evaporated under reduced pressure. The white slurry was extracted with dichloromethane and the combined organic layers dried over sodium sulfate, and filtered. The solvent was removed under reduced pressure and the resultant crude mixture subjected to combiflash chromatography over silica gel with cyclohexane/EtOAc 99:1 to 1:1 to afford 2.3 g of 3-[6-(bromomethyl)-3-pyridyl]-5-(trifluoromethyl)-1,2,4-oxadiazole.

LC/MS (Method A) retention time=1.01 minutes, no mass detected $^1$H NMR (400 MHz, CDCl$_3$) δ ppm: 9.25 (s, 1H), 8.40 (dd, 1H), 7.63 (d, 1H), 4.6 (s, 2H).

$^{19}$F NMR (400 MHz, CDCl$_3$) δ ppm: −65.2 (s).

Step 4: Preparation of 1-[[5-[5-(trifluoromethyl)-1,2,4-oxadiazol-3-yl]-2-pyridyl]methyl]piperidin-2-one

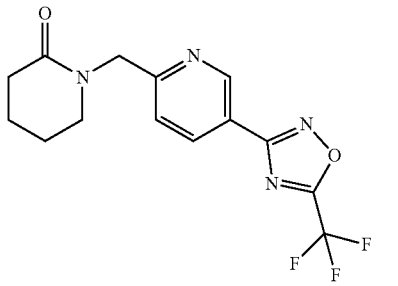 [SMILES: O=C1CCCCN1Cc1ccc(-c2noc(C(F)(F)F)n2)cn1]

To a stirred solution of n-BuLi (1.6 M in hexanes) (0.57 mL, 0.91 mmol) in THF (2.16 mL, 0.65 mmol) at −78° C. was added a solution of piperidin-2-one in THF (3.3 mL). After 20 min at −78° C., 3-[6-(bromomethyl)-3-pyridyl]-5-(trifluoromethyl)-1,2,4-oxadiazole (0.2 g, 0.65 mmol) was added and the reaction mixture stirred at −78° C. for 3.5 hours after which time the reaction mixture was left in the fridge without stirring over the weekend. LCMS showed completion. The reaction mixture was quenched at 0° C. with a sat. NH$_4$Cl solution and the solution extracted with ethyl acetate. The combined organic layers were washed with brine, dried over sodium sulfate, filtered, concentrated and purified by combiflash chromatography over silica gel using a cyclohexane/AcOEt as eluent to afford 0.21 g of the title compound as yellow oil.

LC/MS (Method A) retention time=0.89 minutes, 327 (M+H)

$^1$H NMR (400 MHz, CDCl$_3$) δ ppm: 9.25 (d, 1H), 8.35 (d, 1H), 7.45 (d, 1H), 4.78 (s, 2H), 3.40 (m, 2H), 2.48 (m, 2H), 1.83 (m, 4H)

$^{19}$F NMR (400 MHz, CDCl$_3$) δ ppm: −65.25 (s).

Example 5: This Example Illustrates the Preparation of 2-[[2-chloro-4-[5-(trifluoromethyl)-1,2,4-oxadiazol-3-yl]phenyl]methyl]-1,2-thiazolidine 1,1-dioxide (Compound B-2 of Table B)

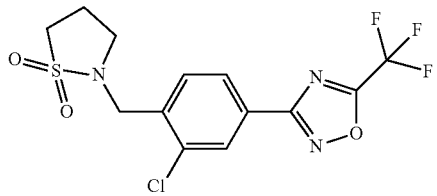 [SMILES: O=S1(=O)CCCN1Cc1ccc(-c2noc(C(F)(F)F)n2)cc1Cl]

To a stirred solution of KHMDS in THF (1M, 0.410 mL, 0.410 mmol) and THF (1 mL) at 0° C. was added a solution of 1,1-dioxo-isothiazolidine (0.044 g, 0.35 mmol) in THF (0.5 mL). The reaction mixture was stirred for 30 minutes at 0° C. and then 3-[4-(bromomethyl)-3-chloro-phenyl]-5-(trifluoromethyl)-1,2,4-oxadiazole (0.100 g, 0.293 mmol), prepared according to procedures described in example 1 using 3-chloro-4-methyl-benzonitrile as starting material, was added. The reaction mixture was stirred at 0° C. for 2 h. The reaction mixture was then quenched with water and warmed to RT. The mixture was extracted with ethyl acetate and the combined organic layers washed with brine, dried over MgSO$_4$, filtered and concentrated under reduce pressure.

LC/MS (Method A) retention time=1.07 minutes, 398 (M+OH)$^-$. The mass observed only in the negative ionization and corresponded to that of a hydrated species.

Example 6: This Example Illustrates the Preparation of 2-[4-[5-(trifluoromethyl)-1,2,4-oxadiazol-3-yl]phenyl]-1,2-thiazolidine 1,1-dioxide (Compound D-1 of Table D)

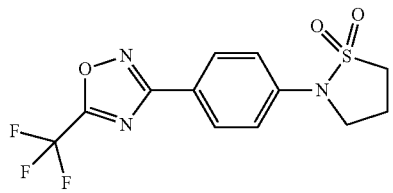 [SMILES: O=S1(=O)CCCN1c1ccc(-c2noc(C(F)(F)F)n2)cc1]

Step 1:
4-(1,1-dioxo-1,2-thiazolidin-2-yl)benzonitrile

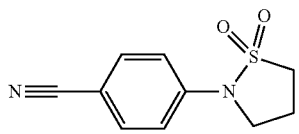 [SMILES: N#Cc1ccc(N2CCCS2(=O)=O)cc1]

A sealed tube was charged with 4-iodobenzonitrile (0.50 g, 2.2 mmol), 1,2-thiazolidine 1,1-dioxide (1.2 equiv.; 0.32 g, 2.6 mmol), dimethylethylenediamine (0.1 equiv., 0.23 mL, 0.22 mmol), cesium fluoride (2.5 equiv., 0.83 g, 5.47 mmol), copper iodide (0.05 equiv., 0.02 g, 0.10 mmol), tetrahydrofuran (4.7 mL) and the reaction contents were stirred at room temperature for 24 hours. The reaction contents were diluted with ethyl acetate and a saturated aqueous ammonium chloride solution. The layers were separated and the organic fraction was washed with water, dried over sodium sulfate, and concentrated under reduced pressure. The corresponding crude yellow oil (449 mg) was taken up in the next step without additional purification or characterization.

$^1$H NMR (400 MHz, CDCl$_3$) δ ppm: 7.85 (d, 2H), 7.30 (d, 2H), 3.82 (t, 2H), 3.28 (t, 2H), 3.30 (m, 2H).

Step 2: 4-(1,1-dioxo-1,2-thiazolidin-2-yl)-N-hydroxy-benzamidine

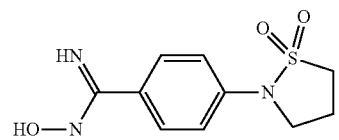 [SMILES: N=C(NO)c1ccc(N2CCCS2(=O)=O)cc1]

In a flask under argon, to hydroxylamine hydrochloride (3.0 equiv., 0.42 g 6.0 mmol) and ethanol (5 mL) was added triethylamine (3.0 equiv., 0.85 mL, 6.0 mmol) at 25° C. The resultant suspension was allowed to stir for 30 minutes after which 4-(1,1-dioxo-1,2-thiazolidin-2-yl)benzonitrile (0.45 g, 2.0 mmol) was introduced and the reaction mixture heated at a temperature of 50° C. for 6 hours. Ethanol was evaporated under reduced pressure and the crude reaction mixture taken up in the next step without additional purification or characterization.

Step 3: 2-[4-[5-(trifluoromethyl)-1,2,4-oxadiazol-3-yl]phenyl]-1,2-thiazolidine 1,1-dioxide

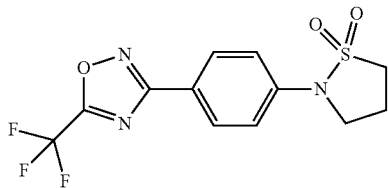 [SMILES: O=S1(=O)CCCN1c1ccc(-c2noc(C(F)(F)F)n2)cc1]

To a stirred solution of crude 4-(1,1-dioxo-1,2-thiazolidin-2-yl)-N-hydroxy-benzamidine (0.2 g, 2.0 mmol) in tetrahydrofuran (4 mL) was added dropwise trifluoroacetic anhydride (1.5 equiv, 0.43 mL, 3.0 mmol) at 25° C. The solvent was removed under reduced pressure, affording an orange oil which was dissolved in a minimal amount of dichloromethane and then washed with a saturated aqueous sodium bicarbonate solution. The organic phase was dried over sodium sulfate, filtrated, and solvent was removed under vacuum. The crude residue was purified by combiflash chromatography over silica gel (cyclohexane:EtOAc eluent gradient 9:1 to 1:9) to afford 0.21 g (50% yield) of the title compound as a beige solid (melting point range=154-158° C.).

LC/MS (Method A) retention time=0.97 minutes, 350 (M+OH)$^-$. The mass observed only in the negative ionization and corresponded to that of a hydrated species.

$^1$H NMR (400 MHz, CDCl$_3$) δ ppm: 8.11 (d, 2H), 7.35 (d, 2H), 3.86 (t, 2H), 3.44 (t, 2H), 2.60 (m, 2H).

$^{19}$F NMR (400 MHz, CDCl$_3$) δ ppm: −65.36 (s).

Example 7: This Example Illustrates the Preparation of 2 2-[4-[5-(trifluoromethyl)-1,2,4-oxadiazol-3-yl]phenyl]isoxazolidin-3-one (Compound C-2 of Table C)

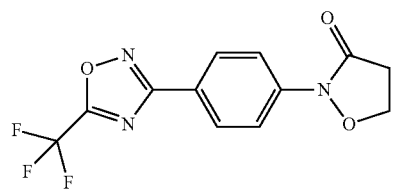 [SMILES: O=C1CCON1c1ccc(-c2noc(C(F)(F)F)n2)cc1]

Step 1: 4-(3-oxoisoxazolidin-2-yl)benzonitrile

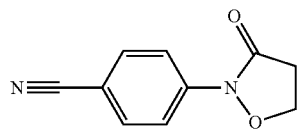 [SMILES: N#Cc1ccc(N2OCCC2=O)cc1]

A sealed tube was charged with 4-iodobenzonitrile (1.0 g, 4.4 mmol), isoxazolidin-3-one (1.2 equiv.; 0.46 g, 5.2 mmol), dimethylethylenediamine (0.1 equiv., 0.47 mL, 0.44 mmol), cesium fluoride (2.5 equiv., 1.66 g, 10.9 mmol), copper iodide (0.05 equiv., 0.04 g, 0.20 mmol), tetrahydrofuran (8 mL) and the reaction contents were stirred at room temperature for 24 hours. The reaction contents were diluted with ethyl acetate and a saturated aqueous ammonium chloride solution. The layers were separated and the organic fraction was washed with water, dried over sodium sulfate, and concentrated under reduced pressure. The crude residue was purified by combiflash chromatography over silica gel (cyclohexane:EtOAc eluent gradient 9:1 to 1:9) to afford 0.82 g (50% yield) of the title compound as an amorphous brown solid.

LC/MS (Method A) retention time=0.72 minutes, 188 (M+H)$^+$.

$^1$H NMR (400 MHz, CDCl$_3$) δ ppm: 7.83 (d, 2H), 7.65 (d, 2H), 4.59 (t, 2H), 3.07 (t, 2H), 3.30 (m, 2H).

Step 2: N-hydroxy-4-(3-oxoisoxazolidin-2-yl)benzamidine

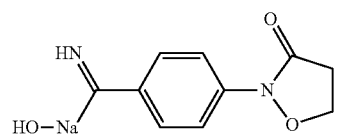

In a flask under argon, to hydroxylamine hydrochloride (3.0 equiv., 0.48 g, 7.0 mmol) and ethanol (6 mL) was added triethylamine (3.0 equiv., 0.97 mL, 7.0 mmol) at 25° C. The resultant suspension was allowed to stir for 30 minutes after which 4-(3-oxoisoxazolidin-2-yl)benzonitrile (0.44 g, 2.3 mmol) was introduced and the reaction mixture heated at a temperature of 50° C. for 6 hours. Ethanol was evaporated under reduced pressure and the crude reaction mixture taken up in the next step without additional purification or characterization.

Step 3: 2 2-[4-[5-(trifluoromethyl)-1,2,4-oxadiazol-3-yl]phenyl]isoxazolidin-3-one

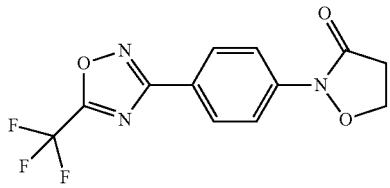 [SMILES: O=C1CCON1c1ccc(-c2noc(C(F)(F)F)n2)cc1]

To a stirred solution of crude N-hydroxy-4-(3-oxoisoxazolidin-2-yl)benzamidine (0.51 g, 2.3 mmol) in tetrahydrofuran (10 mL) was added dropwise trifluoroacetic anhydride (1.5 equiv, 0.49 mL, 3.4 mmol) at 25° C. The solvent was removed under reduced pressure, affording an orange oil which was dissolved in a minimal amount of dichloromethane and then washed with a saturated aqueous sodium bicarbonate solution. The organic phase was dried over sodium sulfate, filtrated, and solvent was removed under vacuum. The crude residue was purified by combiflash chromatography over silica gel (cyclohexane:EtOAc eluent gradient 9:1 to 1:9) to afford 0.13 g (19% yield) of the title compound as a white solid (melting point range=74-77° C.).

LC/MS (Method A) retention time=1.03 minutes, 300 (M+H)$^+$.

$^1$H NMR (400 MHz, CDCl$_3$) δ ppm: 8.13 (d, 2H), 7.87 (d, 2H), 4.59 (t, 2H), 3.07 (t, 2H).

$^{19}$F NMR (400 MHz, CDCl$_3$) δ ppm: −65.37 (s).

Example 8: This Example Illustrates the Preparation of tert-butyl 3-oxo-4-[[4-[5-(trifluoromethyl)-1,2,4-oxadiazol-3-yl]phenyl]methyl]piperazine-1-carboxylate (Compound A-30 of Table A)

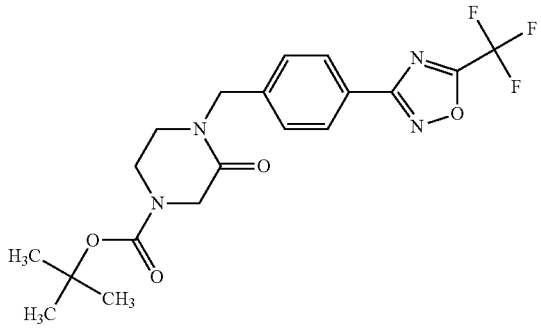 [SMILES: CC(C)(C)OC(=O)N1CCN(Cc2ccc(-c3noc(C(F)(F)F)n3)cc2)C(=O)C1]

To a stirred solution of KHMDS in THF (0.456 mL, 0.456 mmol) in THF (1.1 mL) at 0° C. was added a solution of 1-Boc-3-oxopiperazine (0.091 g, 0.456 mmol) in THF (0.33 ml). After 30 min at 0° C., 3-[4-(bromomethyl)phenyl]-5-(trifluoromethyl)-1,2,4-oxadiazole (0.100 g, 0.326 mmol) was added and the reaction mixture was stirred for 1 h at 0° C. The reaction mixture was left at 4° C. overnight without stirring. The reaction mixture was quenched at 0° C. with a 1M HCl solution and the mixture was extracted with EtOAc. The combined organic layers were washed with brine, dried over Na$_2$SO$_4$, filtered, concentrated and purified by Isco combiflash Rf using cyclohexane/AcOEt as eluent to give tert-butyl 3-oxo-4-[[4-[5-(trifluoromethyl)-1,2,4-oxadiazol-3-yl]phenyl]methyl]piperazine-1-carboxylate as a white solid.

$^1$H NMR (400 MHz, CDCl$_3$) δ ppm: 1.40 (s, 9H) 3.23 (t, J=5.1 Hz, 2H) 3.56 (t, J=5.3 Hz, 2H) 4.12 (s, 2H) 4.63 (s, 2H) 7.35 (d, J=8.4 Hz, 2H) 8.03 (d, J=8.1 Hz, 2H)

LC/MS (Method A) retention time=1.09 min, 443 [M+OH]$^-$ mp: 96-99° C.

Example 9: This Example Illustrates the Preparation of N,N-dimethyl-3-oxo-4-[[4-[5-(trifluoromethyl)-1,2,4-oxadiazol-3-yl]phenyl]methyl]piperazine-1-carboxamide (Compound A-34 of Table A)

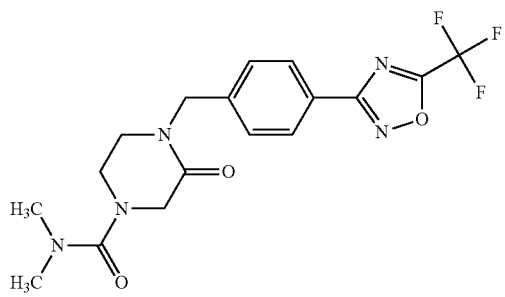 [SMILES: CN(C)C(=O)N1CCN(Cc2ccc(-c3noc(C(F)(F)F)n3)cc2)C(=O)C1]

Step 1: 1-[[4-[5-(trifluoromethyl)-1,2,4-oxadiazol-3-yl]phenyl]methyl]piperazin-2-one hydrochloride (Compound A-36 of Table A)

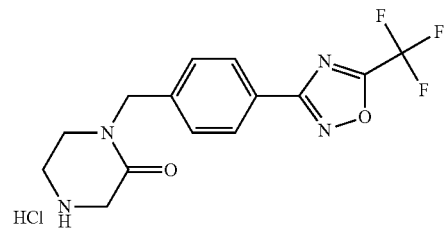 [SMILES: O=C1CNCCN1Cc1ccc(-c2noc(C(F)(F)F)n2)cc1 ; Cl]

To a solution of tert-butyl 3-oxo-4-[[4-[5-(trifluoromethyl)-1,2,4-oxadiazol-3-yl]-phenyl]methyl]piperazine-1-carboxylate (0.375 g, 0.879 mmol) (from Example 8) in THF (2.9 mL) was added HCl in dioxane (2.20 mL, 8.79 mmol). The reaction mixture was stirred for 50 min at RT and then heated to 60° C. for an additional 2 h. All the volatiles were evaporated to give 1-[[4-[5-(trifluoromethyl)-1,2,4-oxadiazol-3-yl]phenyl]methyl]piperazin-2-one hydrochloride as a white solid. The product was used in the next step without further purification.

$^1$H NMR (400 MHz, DMSO-d6) δ ppm: 3.39 (s, 2H) 3.41-3.49 (m, 2H) 3.49-3.57 (m, 2H) 4.71 (s, 2H) 7.58 (d, J=8.4 Hz, 2H) 8.07 (d, J=8.4 Hz, 2H) 9.71 (br. s., 2H)

LC/MS (Method A) retention time=0.72 min; 327 [M+H]$^+$

Step 2: N,N-dimethyl-3-oxo-4-[[4-[5-(trifluoromethyl)-1,2,4-oxadiazol-3-yl]phenyl]methyl]piperazine-1-carboxamide To a solution of 1-[[4-[5-(trifluoromethyl)-1,2,4-oxadiazol-3-yl]phenyl]methyl]piperazin-2-one hydrochloride (0.050 g, 0.14 mmol) in dichloromethane (0.5 mL) was added N,N-dimethylcarbamoyl chloride (0.025 mL, 0.28 mmol) followed by triethylamine (0.058 mL, 0.41 mmol). The reaction mixture was stirred for 2.5 h at RT, after which a saturated aq. NaHCO$_3$ solution was added and the aqueous phase was extracted with dichloromethane. The combined organic layers were dried over Na$_2$SO$_4$, filtered, concentrated and purified by Isco combiflash Rf using CH$_2$Cl$_2$/MeOH as eluent to give N,N-dimethyl-3-oxo-4-[[4-[5-(trifluoromethyl)-1,2,4-oxadiazol-3-yl]phenyl]methyl]piperazine-1-carboxamide as a white solid.

$^1$H NMR (400 MHz, CDCl$_3$) δ ppm: 2.79 (s, 6H) 3.27-3.33 (m, 2H) 3.35-3.46 (m, 2H) 3.96 (s, 2H) 4.61 (s, 2H) 7.35 (d, J=8.1 Hz, 2H) 8.02 (d, J=8.1 Hz, 2H)

LC/MS (Method A) retention time=0.91 min; 398 [M+H]$^+$ mp: 111-114° C.

Example 10: This Example Illustrates the Preparation of N,N-dimethyl-3-oxo-4-[[4-[5-(trifluoromethyl)-1,2,4-oxadiazol-3-yl]phenyl]methyl]piperazine-1-sulfonamide (Compound A-42 of Table A)

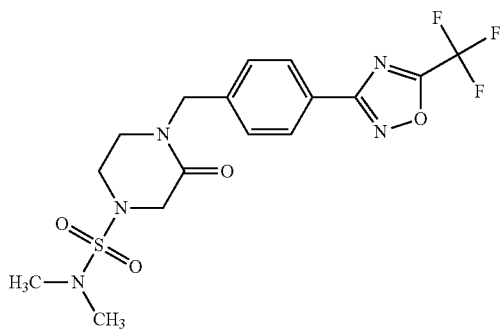 [SMILES: CN(C)S(=O)(=O)N1CCN(Cc2ccc(-c3noc(C(F)(F)F)n3)cc2)C(=O)C1]

To a solution of 1-[[4-[5-(trifluoromethyl)-1,2,4-oxadiazol-3-yl]phenyl]methyl]piperazin-2-one hydrochloride (0.050 g, 0.14 mmol) in dichloromethane (0.5 mL) was added N,N-dimethylsulfamoyl chloride (0.030 mL, 0.28 mmol) followed by triethylamine (0.058 mL, 0.41 mmol). The reaction mixture was stirred for 80 min at RT, after which a saturated aq. NaHCO$_3$ solution was added and the aqueous phase was extracted with dichloromethane. The combined organic layers were dried over Na$_2$SO$_4$, filtered, concentrated and purified by Isco combiflash Rf using CH$_2$Cl$_2$/MeOH as eluent to give N,N-dimethyl-3-oxo-4-[[4-[5-(trifluoromethyl)-1,2,4-oxadiazol-3-yl]phenyl]methyl]piperazine-1-sulfonamide as a white solid.

$^1$H NMR (400 MHz, CDCl$_3$) δ ppm: 2.80 (s, 6H) 3.28-3.34 (m, 2H) 3.39-3.46 (m, 2H) 3.88 (s, 2H) 4.64 (s, 2H) 7.35 (d, J=8.4 Hz, 2H) 8.03 (d, J=8.4 Hz, 2H)

LC/MS (Method A) retention time=1.00 min; 434 [M+H]$^+$

Example 11: This Example Illustrates the Preparation of 1-methoxy-3-[4-[5-(trifluoromethyl)-1,2,4-oxadiazol-3-yl]phenyl]imidazolidin-2-one (Compound C-3 of Table C)

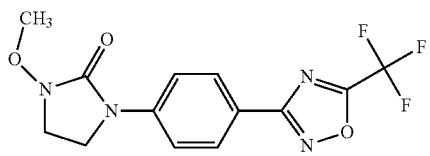 [SMILES: CON1CCN(c2ccc(-c3noc(C(F)(F)F)n3)cc2)C1=O]

Step 1: 1-methoxy-3-[4-[5-(trifluoromethyl)-1,2,4-oxadiazol-3-yl]phenyl]urea

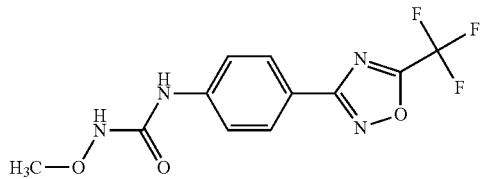 [SMILES: CONC(=O)Nc1ccc(-c2noc(C(F)(F)F)n2)cc1]

To a solution of 4-[5-(trifluoromethyl)-1,2,4-oxadiazol-3-yl]aniline (2.00 g, 8.73 mmol) in THF (29 mL) was added carbonyldiimidazole (2.12 g, 13.1 mmol) followed by methoxylamine hydrochloride (0.948 g, 11.3 mmol) and DIPEA (1.94 mL, 11.3 mmol). The reaction mixture was stirred for 5 hours at 55° C. All the solvents were then evaporated and the residue was purified by Isco combiflash Rf using cyclohexane/EtOAc as eluent to give 1-methoxy-3-[4-[5-(trifluoromethyl)-1,2,4-oxadiazol-3-yl]phenyl]urea as a white solid.

$^1$H NMR (400 MHz, CDCl$_3$) δ ppm: 7.61 (d, J=8.8 Hz, 2H) 7.66 (br. s., 1H) 8.02 (d, J=8.4 Hz, 2H).

LC/MS (Method A) retention time=0.93 min; 303 [M+H]$^+$

Step 2: 1-methoxy-3-[4-[5-(trifluoromethyl)-1,2,4-oxadiazol-3-yl]phenyl]imidazolidin-2-one To a stirred solution of 1-methoxy-3-[4-[5-(trifluoromethyl)-1,2,4-oxadiazol-3-yl]phenyl]urea (0.100 g, 0.331 mmol) in DMF (1.1 mL) at room temperature was added NaH (0.015 g, 0.364 mmol). The reaction mixture was stirred for 30 min and then 1,2-dibromoethane (0.030 mL, 0.35 mmol) was added. After an additional 30 min, a second portion of NaH (0.015 g, 0.364 mmol) was added. The reaction mixture was stirred for 1 h at RT and then poured in water and extracted with AcOEt. The combined organic layers were washed with brine, dried over Na$_2$SO$_4$, filtered, concentrated and purified by Isco combiflash Rf using cyclohexane/AcOEt. The solid obtained was further purified by recrystallization from CH$_2$Cl$_2$ and MeOH to give 1-methoxy-3-[4-[5-(trifluoromethyl)-1,2,4-oxadiazol-3-yl]phenyl]imidazolidin-2-one as white crystals.

$^1$H NMR (400 MHz, CDCl$_3$) δ ppm: 3.54-3.65 (m, 2H) 3.70-3.79 (m, 2H) 3.82 (s, 3H) 7.69 (d, J=8.8 Hz, 2H) 8.05 (d, J=8.0 Hz, 2H)

LC/MS (Method A) retention time=1.02 min; 329 [M+H]$^+$ mp: 185-190° C.

Example 12: This Example Illustrates the Preparation 1-[[4-[5-(trifluoromethyl)-1,2,4-oxadiazol-3-yl]phenyl]methyl]azepan-2-one (Compound A-70 of Table A)

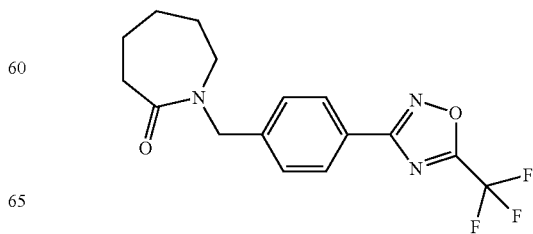

To a solution of nBuLi (1.6M in hexanes 0.712 mL, 1.14 mmol) in THF (3 mL) at −78° C. was introduced a solution of azepan-2-one (137 g, 1.22 mmol) in THF (3 mL). After 20 min at −78° C., 3-[4-(bromomethyl)phenyl]-5-(trifluoromethyl)-1,2,4-oxadiazole (0.25 g, 0.81 mmol) was added and the reaction mixture was stirred for 3 hours while warming from −78° C. to 0° C. using an ice bath. The reaction mixture was then left in the refrigerator (5° C.) overnight without stirring. Then, the reaction mixture was quenched at 0° C. with a saturated ammonium chloride solution and extracted with ethyl acetate. The total combined organic layer was washed with brine, dried over $Na_2SO_4$, filtered, and concentrated under reduced pressure. The crude residue was purified by combiflash column chromatography (cyclohexane/ethyl acetate eluent gradient 1:0 to 1:1) to give 1-[[4-[5-(trifluoromethyl)-1,2,4-oxadiazol-3-yl]phenyl]methyl]azepan-2-one as a colourless oil. (75 mg, 27% yield).

$^1$H NMR (400 MHz, $CDCl_3$) δ ppm: 8.08 (d, 2H), 7.40 (d, 2H), 4.66 (s, 2H), 3.33 (m, 2H), 2.64 (m, 2H), 1.72 (m, 4H), 1.30 (m, 2H).

LC/MS (Method A) retention time=1.06 minutes, 340 (M+H).

Where necessary, enantiomerically pure final compounds may be obtained from racemic materials as appropriate via standard physical separation techniques, such as reverse phase chiral chromatography, or through stereoselective synthetic techniques, (eg, by using chiral starting materials).

TABLE A

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-1 | 1-[[4-[5-(trifluoromethyl)-1,2,4-oxadiazol-3-yl]phenyl]methyl]pyrrolidin-2-one | 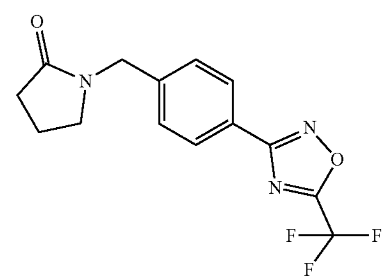 [SMILES: O=C1CCCN1Cc1ccc(-c2noc(C(F)(F)F)n2)cc1] | 0.96 | 312 | A | |
| A-2 | 1-[[4-[5-(trifluoromethyl)-1,2,4-oxadiazol-3-yl]phenyl]methyl]piperidin-2-one | 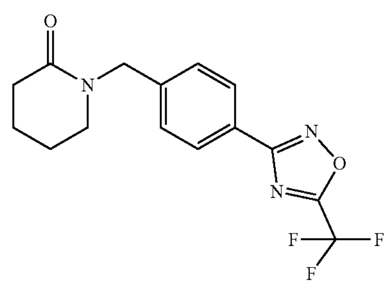 [SMILES: O=C1CCCCN1Cc1ccc(-c2noc(C(F)(F)F)n2)cc1] | 0.99 | 326 | A | 31-34 |
| A-3 | 4-[[4-[5-(trifluoromethyl)-1,2,4-oxadiazol-3-yl]phenyl]methyl]morpholin-3-one | 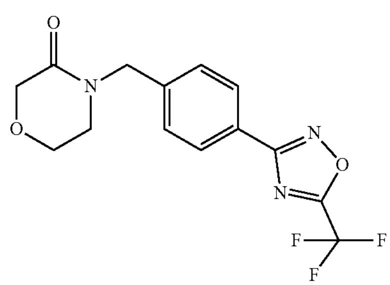 [SMILES: O=C1COCCN1Cc1ccc(-c2noc(C(F)(F)F)n2)cc1] | 0.92 | 328 | A | |
| A-4 | 4,4-dimethyl-2-[[4-[5-(trifluoromethyl)-1,2,4-oxadiazol-3-yl]phenyl]methyl]isoxazolidin-3-one | 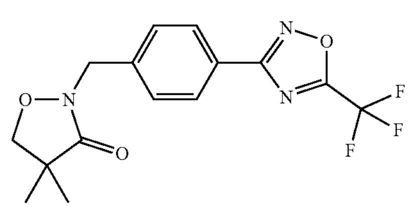 [SMILES: CC1(C)CON(Cc2ccc(-c3noc(C(F)(F)F)n3)cc2)C1=O] | 1.13 | 342 | A | 53-54 |

TABLE A-continued

Melting point (mp) and/or LC/MS data for compounds of Formula (I):

| Entry | Compound Name | Structure | $t_R$ (min) | [M + H]+ (measured) | Method | mp (° C.) |
|---|---|---|---|---|---|---|
| A-5 | 2-[[4-[5-(trifluoromethyl)-1,2,4-oxadiazol-3-yl]phenyl]methyl]isoxazolidin-3-one | 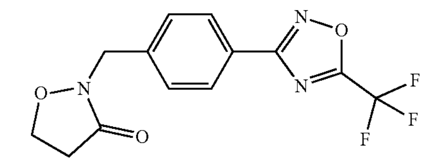 [SMILES: O=C1CCON1Cc1ccc(-c2noc(C(F)(F)F)n2)cc1] | 0.96 | 314 | A | 54-58 |
| A-6 | 5,5-dimethyl-2-[[4-[5-(trifluoromethyl)-1,2,4-oxadiazol-3-yl]phenyl]methyl]isoxazolidin-3-one | 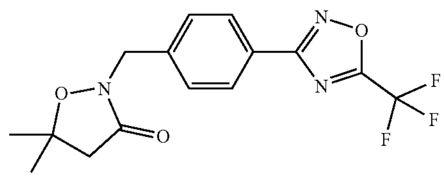 [SMILES: CC1(C)CC(=O)N(Cc2ccc(-c3noc(C(F)(F)F)n3)cc2)O1] | 1.04 | 342 | A | |
| A-7 | 3-methyl-1-[[4-[5-(trifluoromethyl)-1,2,4-oxadiazol-3-yl]phenyl]methyl]pyrrolidin-2-one | 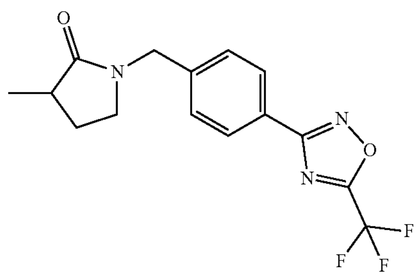 | | | | 83-88 |
| A-8 | 4-methyl-1-[[4-[5-(trifluoromethyl)-1,2,4-oxadiazol-3-yl]phenyl]methyl]pyrrolidin-2-one | 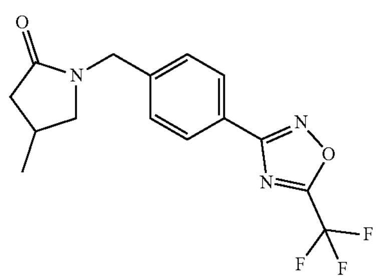 [SMILES: CC1CC(=O)N(Cc2ccc(-c3noc(C(F)(F)F)n3)cc2)C1] | 1.13 | 326 | A | |
| A-9 | 3-[[4-[5-(trifluoromethyl)-1,2,4-oxadiazol-3-yl]phenyl]methyl]-3-azabicyclo[2.2.1]hept-5-en-2-one | 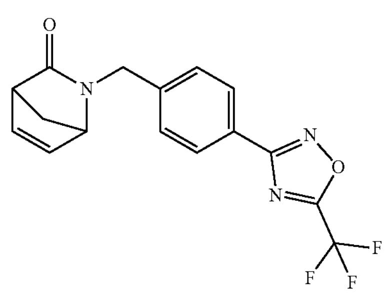 [SMILES: O=C1C2C=CC(C2)N1Cc1ccc(-c2noc(C(F)(F)F)n2)cc1] | | | | 50-53 |
| A-10 | 3-methyl-1-[[4-[5-(trifluoromethyl)-1,2,4-oxadiazol-3-yl]phenyl]methyl]piperidin-2-one | 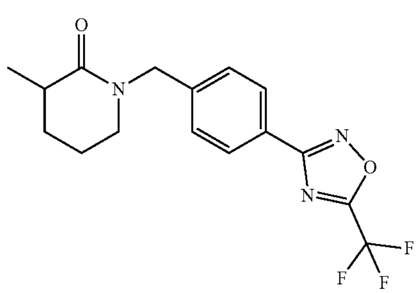 [SMILES: CC1CCCN(Cc2ccc(-c3noc(C(F)(F)F)n3)cc2)C1=O] | 1.12 | 340 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-11 | 4,4-dimethyl-1-[[4-[5-(trifluoromethyl)-1,2,4-oxadiazol-3-yl]phenyl]methyl]piperidine-2,6-dione | 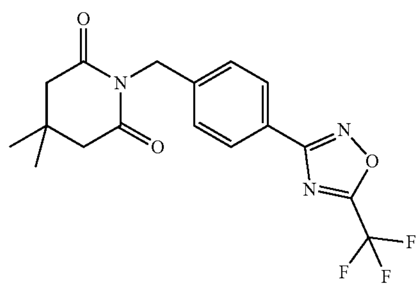 [SMILES: CC1(C)CC(=O)N(Cc2ccc(-c3noc(C(F)(F)F)n3)cc2)C(=O)C1] | 1.14 | 368 | A | |
| A-12 | 1-[[5-[5-(trifluoromethyl)-1,2,4-oxadiazol-3-yl]-2-pyridyl]methyl]piperidin-2-one | 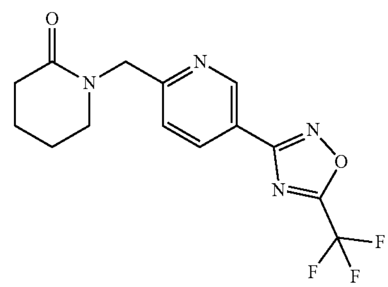 [SMILES: O=C1CCCCN1Cc1ccc(-c2noc(C(F)(F)F)n2)cn1] | | | | |
| A-13 | 5-methyl-1-[[4-[5-(trifluoromethyl)-1,2,4-oxadiazol-3-yl]phenyl]methyl]pyrrolidin-2-one | 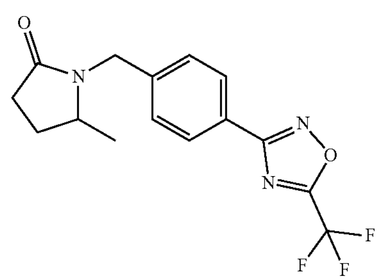 [SMILES: CC1CCC(=O)N1Cc1ccc(-c2noc(C(F)(F)F)n2)cc1] | 1.01 | 326 | A | |
| A-14 | 6-methyl-1-[[4-[5-(trifluoromethyl)-1,2,4-oxadiazol-3-yl]phenyl]methyl]piperidin-2-one | 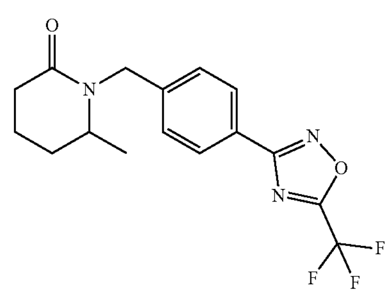 [SMILES: CC1CCCC(=O)N1Cc1ccc(-c2noc(C(F)(F)F)n2)cc1] | 1.05 | 340 | A | |
| A-15 | 3-[[4-[5-(trifluoromethyl)-1,2,4-oxadiazol-3-yl]phenyl]methyl]-3-azabicyclo[2.2.2]octan-2-one | 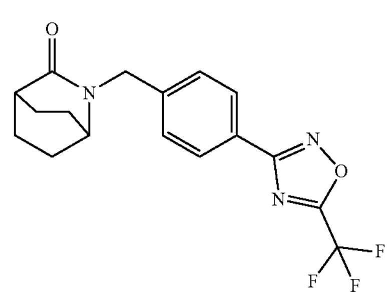 [SMILES: O=C1C2CCC(CC2)N1Cc1ccc(-c2noc(C(F)(F)F)n2)cc1] | 1.04 | 352 | A | |

TABLE A-continued

Melting point (mp) and/or LC/MS data for compounds of Formula (I):

| Entry | Compound Name | Structure | $t_R$ (min) | [M + H]+ (measured) | Method | mp (° C.) |
|---|---|---|---|---|---|---|
| A-16 | 3,3-dimethyl-1-[[4-[5-(trifluoromethyl)-1,2,4-oxadiazol-3-yl]phenyl]methyl]piperidin-2-one | 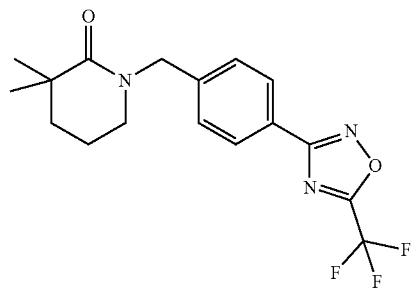 [SMILES: CC1(C)CCCN(Cc2ccc(-c3noc(C(F)(F)F)n3)cc2)C1=O] | 1.13 | 354 | A | |
| A-17 | 4-methyl-1-[[4-[5-(trifluoromethyl)-1,2,4-oxadiazol-3-yl]phenyl]methyl]piperidin-2-one | 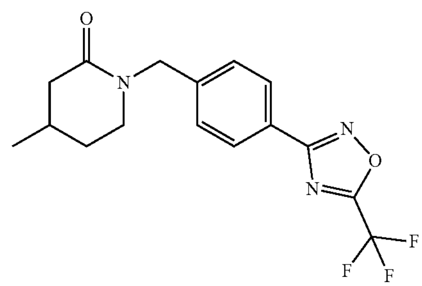 [SMILES: CC1CCN(Cc2ccc(-c3noc(C(F)(F)F)n3)cc2)C(=O)C1] | 1.06 | 340 | A | |
| A-18 | 5-methyl-1-[[4-[5-(trifluoromethyl)-1,2,4-oxadiazol-3-yl]phenyl]methyl]piperidin-2-one | 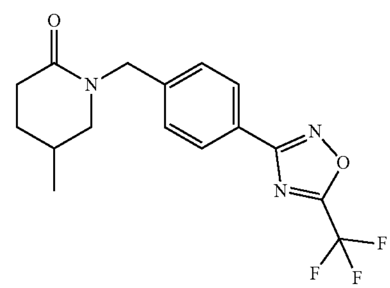 [SMILES: CC1CCC(=O)N(Cc2ccc(-c3noc(C(F)(F)F)n3)cc2)C1] | 1.06 | 340 | A | |
| A-19 | 3-methoxy-1-[[4-[5-(trifluoromethyl)-1,2,4-oxadiazol-3-yl]phenyl]methyl]piperidin-2-one | 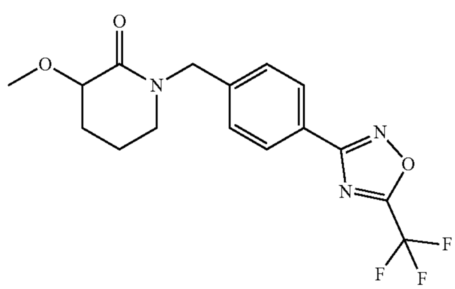 [SMILES: COC1CCCN(Cc2ccc(-c3noc(C(F)(F)F)n3)cc2)C1=O] | 1.00 | 356 | A | |
| A-20 | 4-(trifluoromethyl)-1-[[4-[5-(trifluoromethyl)-1,2,4-oxadiazol-3-yl]phenyl]methyl]azetidin-2-one | 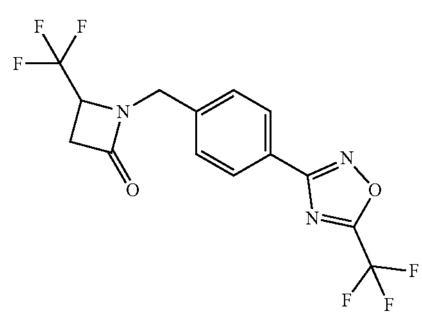 [SMILES: O=C1CC(C(F)(F)F)N1Cc1ccc(-c2noc(C(F)(F)F)n2)cc1] | 1.10 | 366 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-21 | 5-(difluoromethyl)-1-[[4-[5-(trifluoromethyl)-1,2,4-oxadiazol-3-yl]phenyl]methyl]pyrrolidin-2-one | 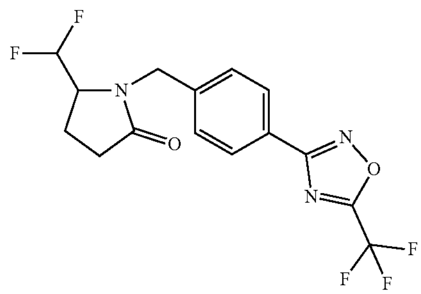 [SMILES: O=C1CCC(C(F)F)N1Cc1ccc(-c2noc(C(F)(F)F)n2)cc1] | 1.04 | 362 | A | |
| A-22 | 1-[[2-fluoro-4-[5-(trifluoromethyl)-1,2,4-oxadiazol-3-yl]phenyl]methyl]pyrrolidin-2-one | 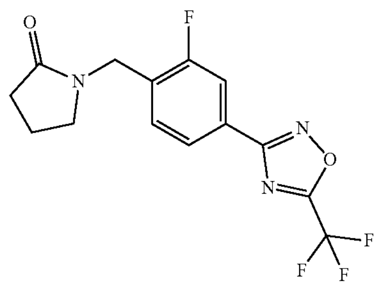 [SMILES: O=C1CCCN1Cc1ccc(-c2noc(C(F)(F)F)n2)cc1F] | | | | 55-60 |
| A-23 | 1-[[4-[5-(trifluoromethyl)-1,2,4-oxadiazol-3-yl]phenyl]methyl]azetidin-2-one | 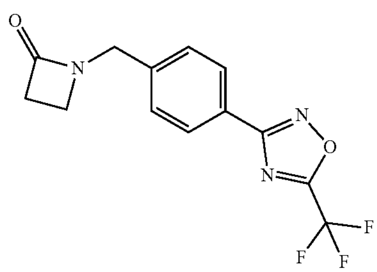 [SMILES: O=C1CCN1Cc1ccc(-c2noc(C(F)(F)F)n2)cc1] | 0.94 | 298 | A | |
| A-24 | 3-[[4-[5-(trifluoromethyl)-1,2,4-oxadiazol-3-yl]phenyl]methyl]-3-azabicyclo[2.2.1]heptan-2-one | 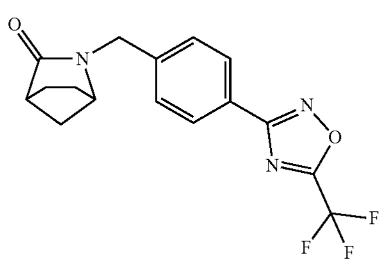 [SMILES: O=C1C2CCC(C2)N1Cc1ccc(-c2noc(C(F)(F)F)n2)cc1] | 1.02 | 338 | A | |
| A-25 | 4-[[4-[5-(trifluoromethyl)-1,2,4-oxadiazol-3-yl]phenyl]methyl]-4-azaspiro[2.5]octan-5-one | 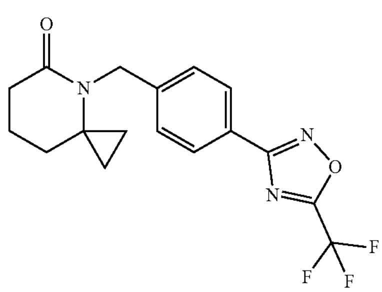 [SMILES: O=C1CCCC2(CC2)N1Cc1ccc(-c2noc(C(F)(F)F)n2)cc1] | 1.07 | 351 | A | |

TABLE A-continued

Melting point (mp) and/or LC/MS data for compounds of Formula (I):

| Entry | Compound Name | Structure | $t_R$ (min) | [M + H]⁺ (measured) | Method | mp (° C.) |
|---|---|---|---|---|---|---|
| A-26 | 1-methyl-4-[[4-[5-(trifluoromethyl)-1,2,4-oxadiazol-3-yl]phenyl]methyl]piperazine-2,5-dione | 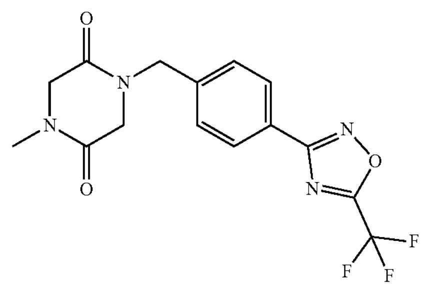 [SMILES: CN1CC(=O)N(Cc2ccc(-c3noc(C(F)(F)F)n3)cc2)CC1=O] | 0.85 | 355 | A | 134-142 |
| A-27 | 4-[[4-[5-(trifluoromethyl)-1,2,4-oxadiazol-3-yl]phenyl]methyl]-4-aza-spiro[2.4]heptan-5-one | 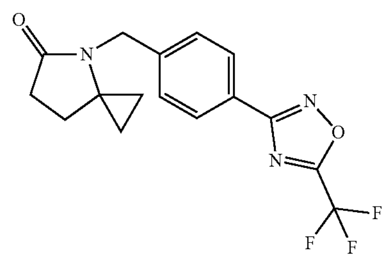 [SMILES: O=C1CCC2(CC2)N1Cc1ccc(-c2noc(C(F)(F)F)n2)cc1] | 1.03 | 338 | A | |
| A-28 | 1-[[5-[5-(trifluoromethyl)-1,2,4-oxadiazol-3-yl]-2-pyridyl]methyl]pyrrolidin-2-one | 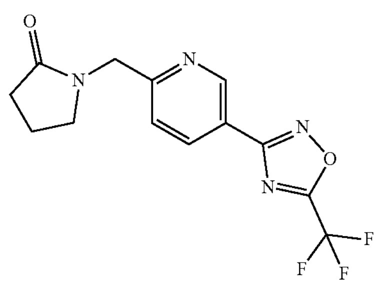 [SMILES: O=C1CCCN1Cc1ccc(-c2noc(C(F)(F)F)n2)cn1] | 0.66 | 329 Mass observed for [M + OH]⁻ | A | |
| A-29 | 1-[[2-fluoro-4-[5-(trifluoromethyl)-1,2,4-oxadiazol-3-yl]phenyl]methyl]piperidin-2-one | 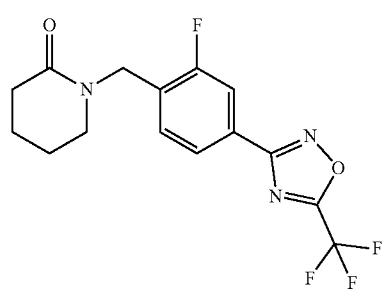 [SMILES: O=C1CCCCN1Cc1ccc(-c2noc(C(F)(F)F)n2)cc1F] | 1.60 | 344 | B | |
| A-30 | tert-butyl 3-oxo-4-[[4-[5-(trifluoromethyl)-1,2,4-oxadiazol-3-yl]phenyl]methyl]piperazine-1-carboxylate | 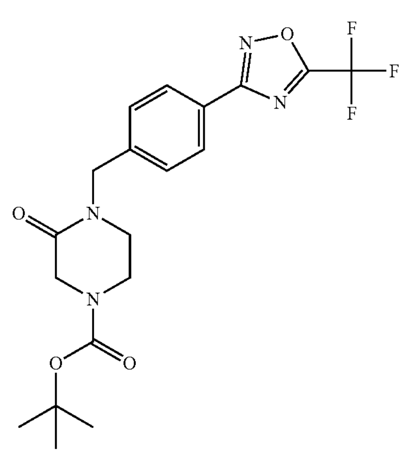 [SMILES: CC(C)(C)OC(=O)N1CCN(Cc2ccc(-c3noc(C(F)(F)F)n3)cc2)C(=O)C1] | 1.09 | [M + Na] 449 | A | 96-99 |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-31 | 4-(2-methoxyacetyl)-1-[[4-[5-(trifluoromethyl)-1,2,4-oxadiazol-3-yl]phenyl]methyl]piperazin-2-one | 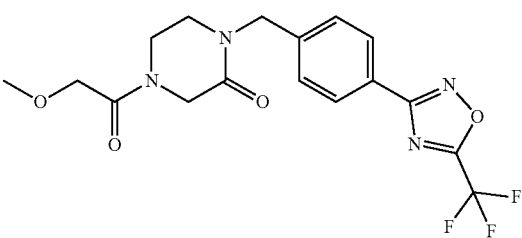 [SMILES: COCC(=O)N1CCN(Cc2ccc(-c3noc(C(F)(F)F)n3)cc2)C(=O)C1] | 0.87 | 399 | A | |
| A-32 | ethyl 3-oxo-4-[[4-[5-(trifluoromethyl)-1,2,4-oxadiazol-3-yl]phenyl]methyl]piperazine-1-carboxylate | 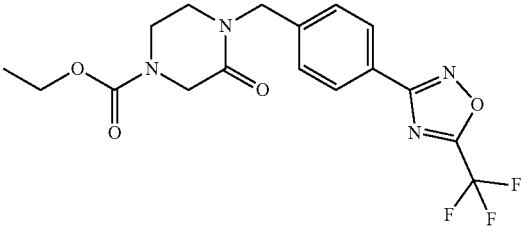 [SMILES: CCOC(=O)N1CCN(Cc2ccc(-c3noc(C(F)(F)F)n3)cc2)C(=O)C1] | 0.99 | 399 | A | |
| A-33 | N-methyl-3-oxo-4-[[4-[5-(trifluoromethyl)-1,2,4-oxadiazol-3-yl]phenyl]methyl]piperazine-1-carboxamide | 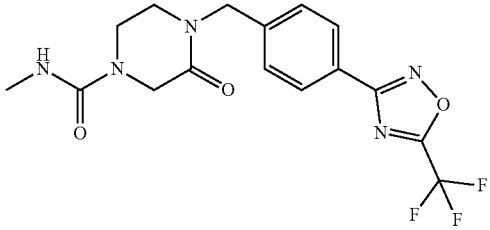 [SMILES: CNC(=O)N1CCN(Cc2ccc(-c3noc(C(F)(F)F)n3)cc2)C(=O)C1] | 0.84 | 384 | A | 114-118 |
| A-34 | N,N-dimethyl-3-oxo-4-[[4-[5-(trifluoromethyl)-1,2,4-oxadiazol-3-yl]phenyl]methyl]piperazine-1-carboxamide | 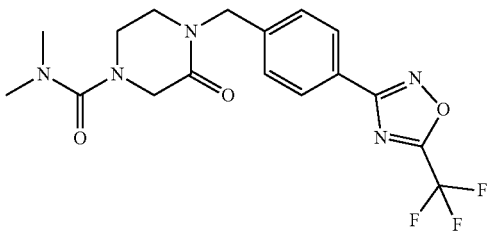 [SMILES: CN(C)C(=O)N1CCN(Cc2ccc(-c3noc(C(F)(F)F)n3)cc2)C(=O)C1] | 0.91 | 398 | A | 111-114 |
| A-35 | 4-acetyl-1-[[4-[5-(trifluoromethyl)-1,2,4-oxadiazol-3-yl]phenyl]methyl]piperazin-2-one | 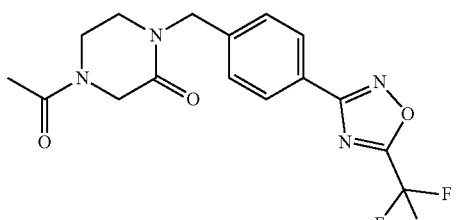 | 0.86 | 369 | A | |
| A-36 | 1-[[4-[5-(trifluoromethyl)-1,2,4-oxadiazol-3-yl]phenyl]methyl]piperazin-4-ium-2-one; chloride | 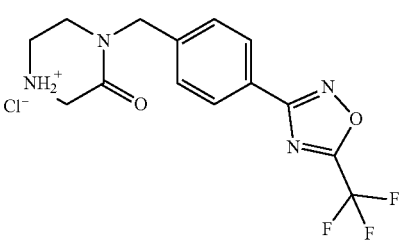 [SMILES: [Cl-] ; O=C1CNCCN1Cc1ccc(-c2noc(C(F)(F)F)n2)cc1] | 0.72 | 327 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-37 | 2-[[4-[5-(trifluoromethyl)-1,2,4-oxadiazol-3-yl]phenyl]methyl]oxazinan-3-one | 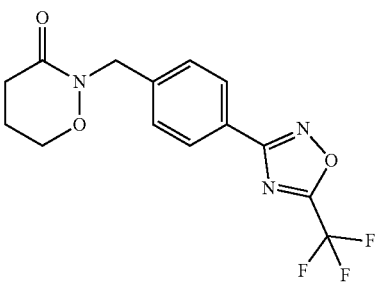 [SMILES: O=C1CCCON1Cc1ccc(-c2noc(C(F)(F)F)n2)cc1] | 0.99 | 328 | A | |
| A-38 | N-(2-methoxyethyl)-3-oxo-4-[[4-[5-(trifluoromethyl)-1,2,4-oxadiazol-3-yl]phenyl]methyl]piperazine-1-carboxamide | 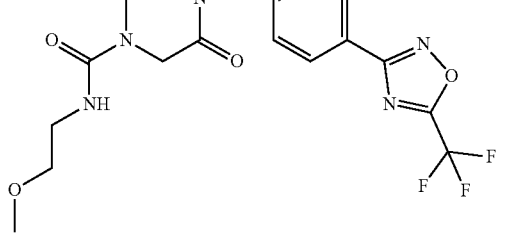 | 0.86 | 428 | A | 120-128 |
| A-39 | N-methoxy-N-methyl-3-oxo-4-[[4-[5-(trifluoromethyl)-1,2,4-oxadiazol-3-yl]phenyl]methyl]piperazine-1-carboxamide | 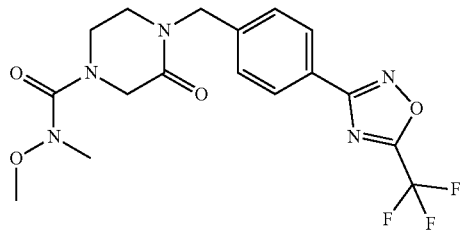 [SMILES: CON(C)C(=O)N1CCN(Cc2ccc(-c3noc(C(F)(F)F)n3)cc2)C(=O)C1] | 0.96 | 414 | A | |
| A-40 | 4-(cyclopropane-carbonyl)-1-[[4-[5-(trifluoromethyl)-1,2,4-oxadiazol-3-yl]phenyl]methyl]piperazin-2-one | 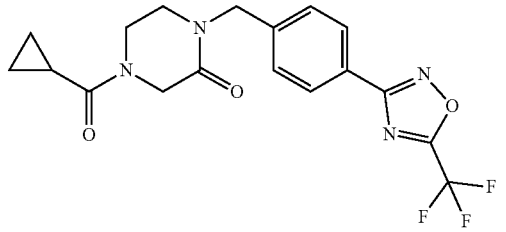 [SMILES: O=C1CN(C(=O)C2CC2)CCN1Cc1ccc(-c2noc(C(F)(F)F)n2)cc1] | 0.93 | 395 | A | |
| A-41 | 4-methylsulfonyl-1-[[4-[5-(trifluoromethyl)-1,2,4-oxadiazol-3-yl]phenyl]methyl]piperazin-2-one | 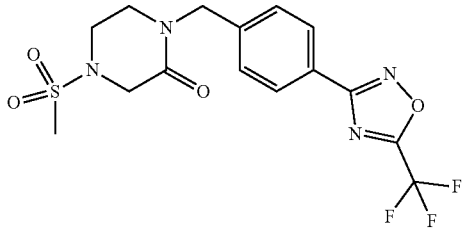 [SMILES: CS(=O)(=O)N1CCN(Cc2ccc(-c3noc(C(F)(F)F)n3)cc2)C(=O)C1] | 0.91 | 405 | A | 155-160 |
| A-42 | N,N-dimethyl-3-oxo-4-[[4-[5-(trifluoromethyl)-1,2,4-oxadiazol-3-yl]phenyl]methyl]piperazine-1-sulfonamide | 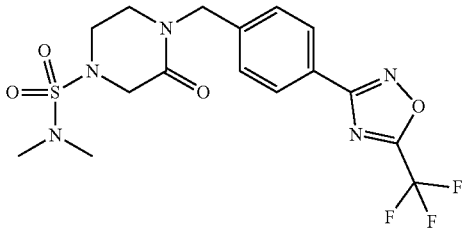 [SMILES: CN(C)S(=O)(=O)N1CCN(Cc2ccc(-c3noc(C(F)(F)F)n3)cc2)C(=O)C1] | 1.00 | 434 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-43 | N-methyl-3-oxo-4-[[4-[5-(trifluoromethyl)-1,2,4-oxadiazol-3-yl]phenyl]methyl]piperazine-1-sulfonamide | 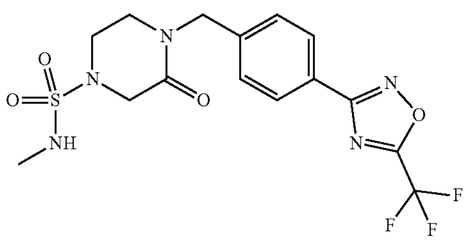 [SMILES: CNS(=O)(=O)N1CCN(Cc2ccc(-c3noc(C(F)(F)F)n3)cc2)C(=O)C1] | 0.92 | 420 | A | |
| A-44 | 1-[[3-fluoro-4-[5-(trifluoromethyl)-1,2,4-oxadiazol-3-yl]phenyl]methyl]piperidin-2-one | 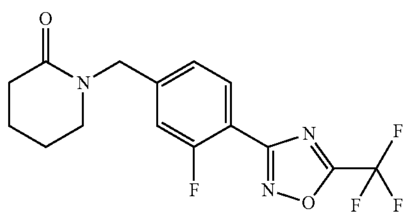 [SMILES: O=C1CCCCN1Cc1ccc(-c2noc(C(F)(F)F)n2)c(F)c1] | 1.04 | 344 | A | |
| A-45 | 3-[[4-[5-(trifluoromethyl)-1,2,4-oxadiazol-3-yl]phenyl]methyl]oxazolidin-2-one | 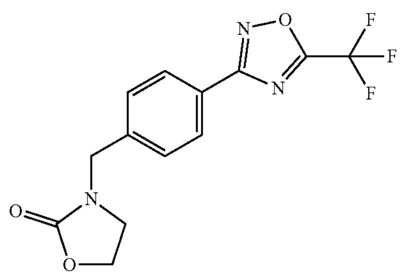 [SMILES: O=C1OCCN1Cc1ccc(-c2noc(C(F)(F)F)n2)cc1] | 0.96 | 314 | A | |
| A-46 | 1-methyl-3-[[4-[5-(trifluoromethyl)-1,2,4-oxadiazol-3-yl]phenyl]methyl]imidazolidin-2-one | 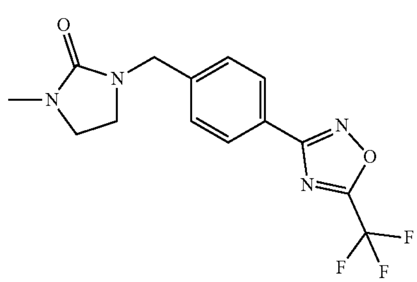 [SMILES: CN1CCN(Cc2ccc(-c3noc(C(F)(F)F)n3)cc2)C1=O] | 0.97 | 327 | A | |
| A-47 | 3-methyl-1-[[4-[5-(trifluoromethyl)-1,2,4-oxadiazol-3-yl]phenyl]methyl]imidazolidine-2,4-dione | 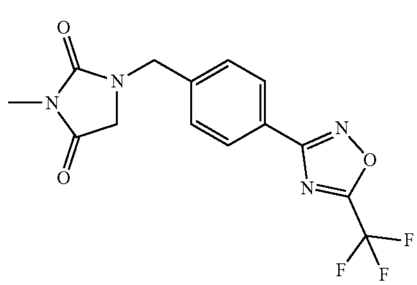 [SMILES: CN1C(=O)CN(Cc2ccc(-c3noc(C(F)(F)F)n3)cc2)C1=O] | 0.94 | 341 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-48 | 1-methyl-3-[[4-[5-(trifluoromethyl)-1,2,4-oxadiazol-3-yl]phenyl]methyl] hexahydro-pyrimidin-2-one | 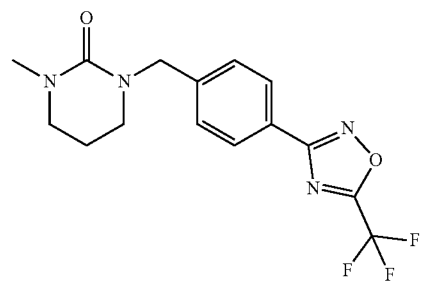 [SMILES: CN1CCCN(Cc2ccc(-c3noc(C(F)(F)F)n3)cc2)C1=O] | 0.99 | 341 | A | |
| A-49 | 1-[[4-[5-(trifluoromethyl)-1,2,4-oxadiazol-3-yl]phenyl]methyl] piperidine-2,6-dione | 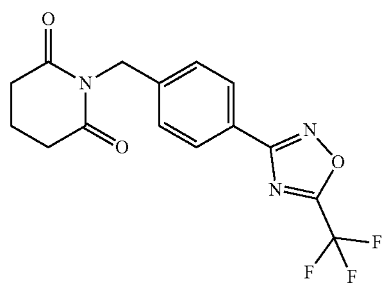 [SMILES: O=C1CCCC(=O)N1Cc1ccc(-c2noc(C(F)(F)F)n2)cc1] | 1.01 | 340 | A | 104-108 |
| A-50 | 1-methyl-3-[[4-[5-(trifluoromethyl)-1,2,4-oxadiazol-3-yl]phenyl]methyl] imidazolidine-2,4-dione | 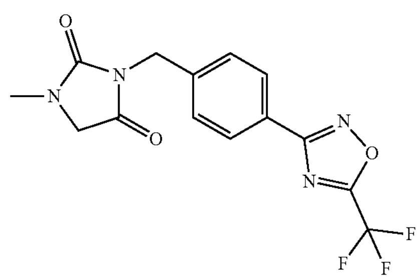 [SMILES: CN1CC(=O)N(Cc2ccc(-c3noc(C(F)(F)F)n3)cc2)C1=O] | 0.94 | 341 | A | |
| A-51 | 1-[[4-[5-(trifluoromethyl)-1,2,4-oxadiazol-3-yl]phenyl]methyl] pyrrolidine-2,5-dione | 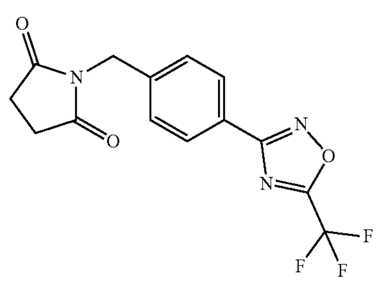 [SMILES: O=C1CCC(=O)N1Cc1ccc(-c2noc(C(F)(F)F)n2)cc1] | 0.96 | 326 | A | 113-117 |
| A-52 | 3,3-dimethyl-1-[[6-[5-(trifluoromethyl)-1,2,4-oxadiazol-3-yl]-3-pyridyl]methyl] piperidin-2-one | 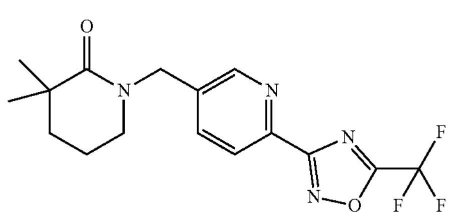 [SMILES: CC1(C)CCCN(Cc2ccc(-c3noc(C(F)(F)F)n3)nc2)C1=O] | 0.98 | 355 | A | |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-53 | 1-[[6-[5-(trifluoromethyl)-1,2,4-oxadiazol-3-yl]-3-pyridyl]methyl]piperidin-2-one | 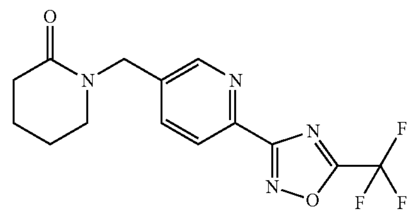 [SMILES: O=C1CCCCN1Cc1ccc(-c2noc(C(F)(F)F)n2)nc1] | | | | 80-89 |
| A-54 | 1-[[3-fluoro-4-[5-(trifluoromethyl)-1,2,4-oxadiazol-3-yl]phenyl]methyl]-3,3-dimethyl-piperidin-2-one | 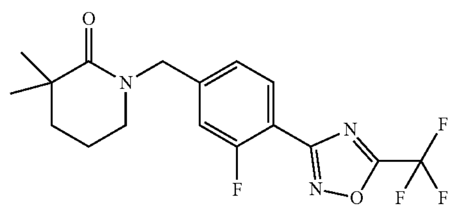 [SMILES: CC1(C)CCCN(Cc2ccc(-c3noc(C(F)(F)F)n3)c(F)c2)C1=O] | | | | 69-73 |
| A-55 | 4-acetyl-1-[[4-[5-(trifluoromethyl)-1,2,4-oxadiazol-3-yl]phenyl]methyl]piperazine-2,6-dione | 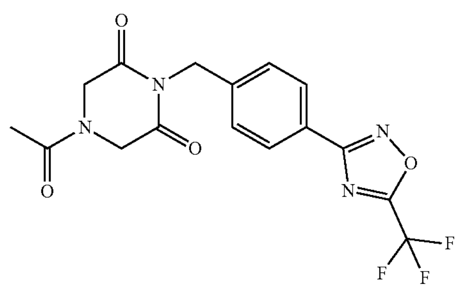 [SMILES: CC(=O)N1CC(=O)N(Cc2ccc(-c3noc(C(F)(F)F)n3)cc2)C(=O)C1] | | | | 111-114 |
| A-56 | N,N-dimethyl-3,5-dioxo-4-[[4-[5-(trifluoromethyl)-1,2,4-oxadiazol-3-yl]phenyl]methyl]piperazine-1-carboxamide | 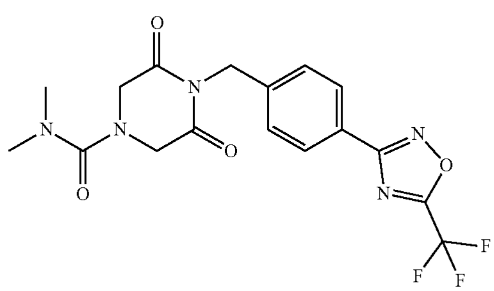 [SMILES: CN(C)C(=O)N1CC(=O)N(Cc2ccc(-c3noc(C(F)(F)F)n3)cc2)C(=O)C1] | | | | 138-141 |
| A-57 | ethyl 3,5-dioxo-4-[[4-[5-(trifluoromethyl)-1,2,4-oxadiazol-3-yl]phenyl]methyl]piperazine-1-carboxylate | 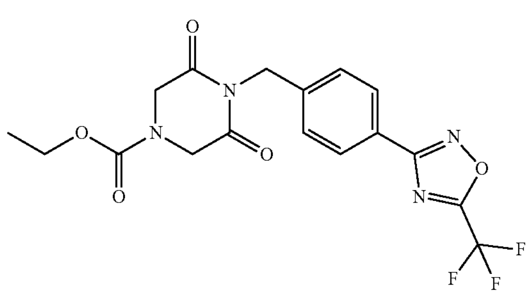 [SMILES: CCOC(=O)N1CC(=O)N(Cc2ccc(-c3noc(C(F)(F)F)n3)cc2)C(=O)C1] | | | | 89-92 |

TABLE A-continued

Melting point (mp) and/or LC/MS data for compounds of Formula (I):

| Entry | Compound Name | Structure | $t_R$ (min) | [M + H]⁺ (measured) | Method | mp (° C.) |
|---|---|---|---|---|---|---|
| A-58 | N-methyl-3,5-dioxo-4-[[4-[5-(trifluoromethyl)-1,2,4-oxadiazol-3-yl]phenyl]methyl]piperazine-1-carboxamide | 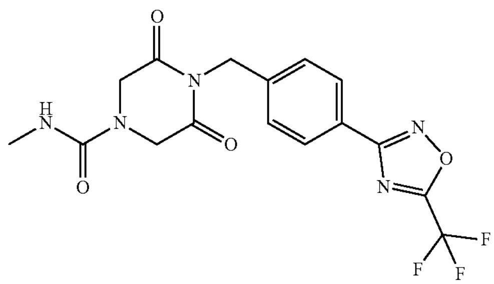 [SMILES: CNC(=O)N1CC(=O)N(Cc2ccc(-c3noc(C(F)(F)F)n3)cc2)C(=O)C1] | | | | 148-153 |
| A-59 | 4-methylsulfonyl-1-[[4-[5-(trifluoromethyl)-1,2,4-oxadiazol-3-yl]phenyl]methyl]piperazine-2,6-dione | 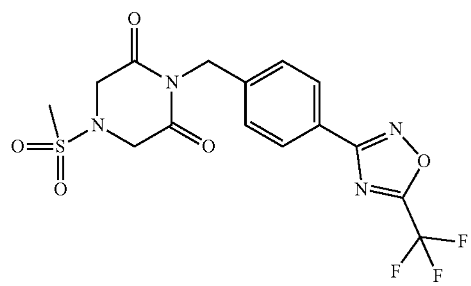 [SMILES: CS(=O)(=O)N1CC(=O)N(Cc2ccc(-c3noc(C(F)(F)F)n3)cc2)C(=O)C1] | 1.00 | 419 | A | |
| A-60 | N,N-dimethyl-3,5-dioxo-4-[[4-[5-(trifluoromethyl)-1,2,4-oxadiazol-3-yl]phenyl]methyl]piperazine-1-sulfonamide | 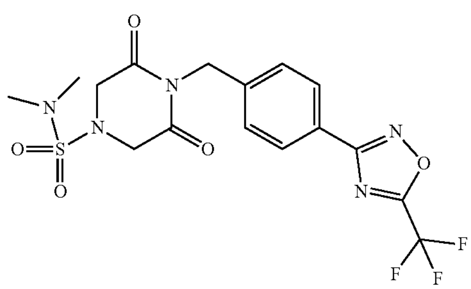 [SMILES: CN(C)S(=O)(=O)N1CC(=O)N(Cc2ccc(-c3noc(C(F)(F)F)n3)cc2)C(=O)C1] | 1.06 | 448 | A | |
| A-61 | 1-[[4-[5-(trifluoromethyl)-1,2,4-oxadiazol-3-yl]phenyl]methyl]piperazin-4-ium-2,6-dione; chloride | 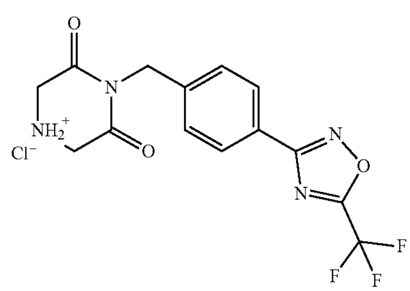 [SMILES: [Cl-] ; O=C1CNCC(=O)N1Cc1ccc(-c2noc(C(F)(F)F)n2)cc1] | 0.89 | 341 (M − Cl) | A | |
| A-62 | tert-butyl 3,5-dioxo-4-[[4-[5-(trifluoromethyl)-1,2,4-oxadiazol-3-yl]phenyl]methyl]piperazine-1-carboxylate | 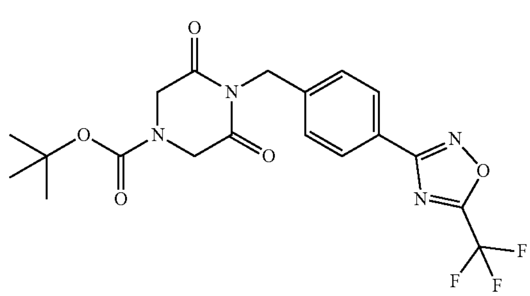 [SMILES: CC(C)(C)OC(=O)N1CC(=O)N(Cc2ccc(-c3noc(C(F)(F)F)n3)cc2)C(=O)C1] | | | | 94-102 |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-63 | 1-[[3-fluoro-4-[5-(trifluoromethyl)-1,2,4-oxadiazol-3-yl]phenyl]methyl]pyrrolidin-2-one | 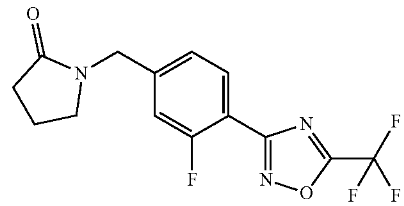 [SMILES: O=C1CCCN1Cc1ccc(-c2noc(C(F)(F)F)n2)c(F)c1] | 0.99 | 330 | A | |
| A-64 | 2-[[3-fluoro-4-[5-(trifluoromethyl)-1,2,4-oxadiazol-3-yl]phenyl]methyl]-4,4-dimethyl-isoxazolidin-3-one | 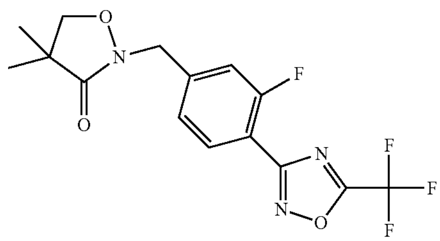 [SMILES: CC1(C)CON(Cc2ccc(-c3noc(C(F)(F)F)n3)c(F)c2)C1=O] | 0.98 | 376 (M + OH) | A | |
| A-65 | 3-[[4-[5-(trifluoromethyl)-1,2,4-oxadiazol-3-yl]phenyl]methyl]imidazolidine-2,4-dione | 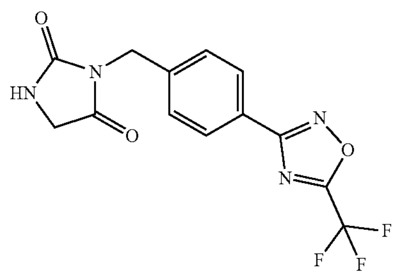 [SMILES: O=C1CNC(=O)N1Cc1ccc(-c2noc(C(F)(F)F)n2)cc1] | | | | 200-203 |
| A-66 | 2-[[2,3-difluoro-4-[5-(trifluoromethyl)-1,2,4-oxadiazol-3-yl]phenyl]methyl]isoxazolidin-3-one | 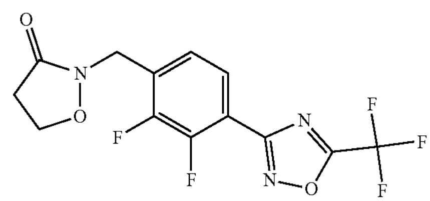 [SMILES: O=C1CCON1Cc1ccc(-c2noc(C(F)(F)F)n2)c(F)c1F] | 0.99 | 350 | A | |
| A-67 | 2-[[2,6-difluoro-4-[5-(trifluoromethyl)-1,2,4-oxadiazol-3-yl]phenyl]methyl]isoxazolidin-3-one | 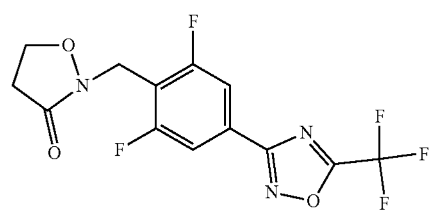 [SMILES: O=C1CCON1Cc1c(F)cc(-c2noc(C(F)(F)F)n2)cc1F] | | | | 75-80 |
| A-68 | 2-[[3-fluoro-4-[5-(trifluoromethyl)-1,2,4-oxadiazol-3-yl]phenyl]methyl]isoxazolidin-3-one | 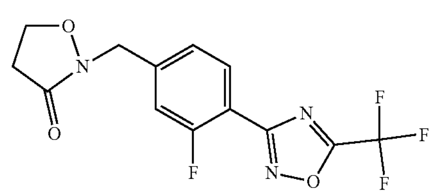 [SMILES: O=C1CCON1Cc1ccc(-c2noc(C(F)(F)F)n2)c(F)c1] | | | | 86-89 |
| A-69 | 1-[[3-fluoro-4-[5-(trifluoromethyl)-1,2,4-oxadiazol-3-yl]phenyl]methyl]azepan-2-one | 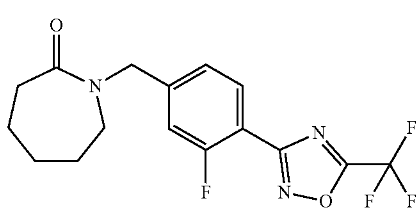 [SMILES: O=C1CCCCCN1Cc1ccc(-c2noc(C(F)(F)F)n2)c(F)c1] | | | | 80-84 |

TABLE A-continued

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| A-70 | 1-[[4-[5-(trifluoromethyl)-1,2,4-oxadiazol-3-yl]phenyl]methyl]azepan-2-one | 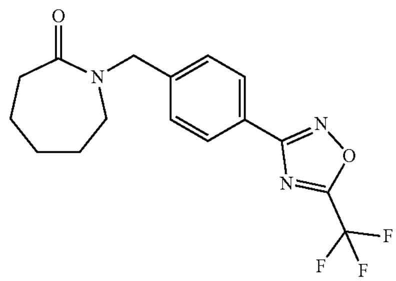 [SMILES: O=C1CCCCCN1Cc1ccc(-c2noc(C(F)(F)F)n2)cc1] | 1.06 | 340 | A | |

TABLE B

Melting point (mp) and/or LC/MS data for compounds of Formula (I):

| Entry | Compound Name | Structure | $t_R$ (min) | $[M + H]^+$ (measured) | Method | mp (° C.) |
|---|---|---|---|---|---|---|
| B-1 | 2-[[4-[5-(trifluoromethyl)-1,2,4-oxadiazol-3-yl]phenyl]methyl]-1,2-thiazolidine 1,1-dioxide | 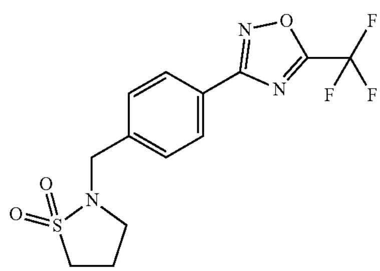 [SMILES: O=S1(=O)CCCN1Cc1ccc(-c2noc(C(F)(F)F)n2)cc1] | | | | 69-73 |
| B-2 | 2-[[2-chloro-4-[5-(trifluoromethyl)-1,2,4-oxadiazol-3-yl]phenyl]methyl]-1,2-thiazolidine 1,1-dioxide | 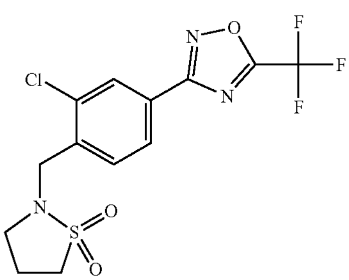 [SMILES: O=S1(=O)CCCN1Cc1ccc(-c2noc(C(F)(F)F)n2)cc1Cl] | 1.07 | 398 Observed mass for $[M + OH]^-$ | A | |
| B-3 | 2-methyl-6-[[4-[5-(trifluoromethyl)-1,2,4-oxadiazol-3-yl]phenyl]methyl]-1,2,6-thiadiazinane 1,1-dioxide | 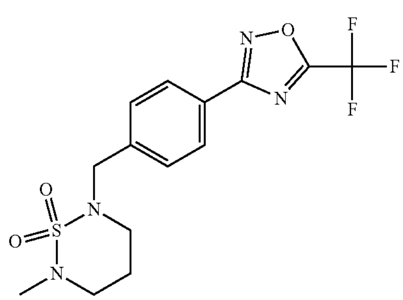 [SMILES: CN1CCCN(Cc2ccc(-c3noc(C(F)(F)F)n3)cc2)S1(=O)=O] | 1.09 | 376 | A | |

TABLE B-continued

Melting point (mp) and/or LC/MS data for compounds of Formula (I):

| Entry | Compound Name | Structure | $t_R$ (min) | [M + H]+ (measured) | Method | mp (° C.) |
|---|---|---|---|---|---|---|
| B-4 | 2-[[2-chloro-4-[5-(trifluoromethyl)-1,2,4-oxadiazol-3-yl]phenyl]methyl]-6-methyl-1,2,6-thiadiazinane 1,1-dioxide | 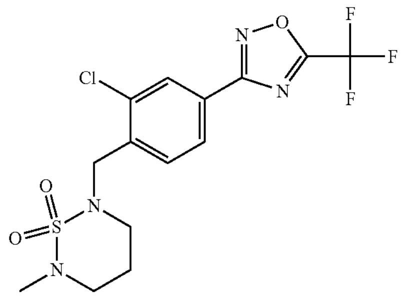 [SMILES: CN1CCCN(Cc2ccc(-c3noc(C(F)(F)F)n3)cc2Cl)S1(=O)=O] | 1.15 | 410 | A | |

TABLE C

Melting point (mp) and/or LC/MS data for compounds of Formula (I):

| Entry | Compound Name | Structure | $t_R$ (min) | [M + H]+ (measured) | Method | mp (° C.) |
|---|---|---|---|---|---|---|
| C-1 | 1-[4-[5-(trifluoromethyl)-1,2,4-oxadiazol-3-yl]phenyl]pyrrolidin-2-one | 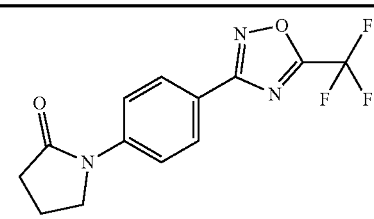 | 1.00 | 298 | A | 151-153 |
| C-2 | 2-[4-[5-(trifluoromethyl)-1,2,4-oxadiazol-3-yl]phenyl]isoxazolidin-3-one | 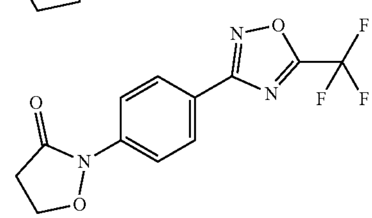 | 1.03 | 300 | A | 74-77 |
| C-3 | 1-methoxy-3-[4-[5-(trifluoromethyl)-1,2,4-oxadiazol-3-yl]phenyl]imidazolidin-2-one | 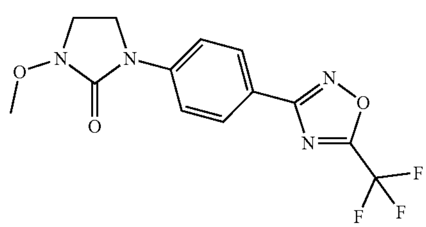 [SMILES: CON1CCN(c2ccc(-c3noc(C(F)(F)F)n3)cc2)C1=O] | 1.02 | 329 | A | 185-190 |

TABLE D

Melting point (mp) and/or LC/MS data for compounds of Formula (I):

| Entry | Compound Name | Structure | $t_R$ (min) | [M + H]+ (measured) | Method | mp (° C.) |
|---|---|---|---|---|---|---|
| D-1 | 2-[4-[5-(trifluoromethyl)-1,2,4-oxadiazol-3-yl]phenyl]-1,2-thiazolidine 1,1-dioxide | 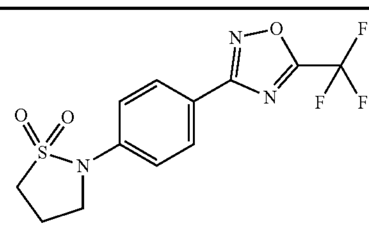 | 0.97 | 350 Observed mass for [M + OH]− | | 154-158 |

BIOLOGICAL EXAMPLES

General Examples of Leaf Disk Tests in Well Plates

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates

Mycelia fragments or conidia suspensions of a fungus, prepared either freshly from liquid cultures of the fungus or from cryogenic storage, are directly mixed into nutrient broth. DMSO solutions of the test compound (max. 10 mg/ml) is diluted with 0.025% Tween20 by a factor of 50 and 10 µl of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example 1: Fungicidal Activity Against *Glomerella lacenarium* (*Colletotrichum lagenarium*) Liquid Culture/Cucumber/Preventative (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds from Tables A to D gave at least 80% control of *Glomerella lagenarium* at 20 ppm when compared to untreated control under the same conditions, which showed extensive disease development:
Compounds (from Table A): A-1, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-37, A-39, A-40, A-41, A-42, A-43, A-44, A-45, A-46, A-47, A-48, A-49, A-50, A-51, A-52, A-54, A-55, A-56, A-57, A-58, A-59, A-61, A-62, A-63, A-64, A-65, A-66, A-67, A-68, A-69, and A-70.
Compounds (from Table B): B-1, B-2, B-3, and B-4.
Compounds (from Table C): C-1, C-2, and C-3.
Compounds (from Table D): D-1.

Example 2: Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12-14 days after application).

The following compounds from Tables A to D gave at least 80% control of *Phakopsora pachyrhizi* at 200 ppm when compared to untreated control under the same conditions, which showed extensive disease development:
Compounds (from Table A): A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-29, A-32, A-33, A-34, A-35, A-37, A-38, A-39, A-40, A-41, A-42, A-43, A-46, A-47, A-48, A-49, A-50, A-51, A-54, A-55, A-56, A-57, A-58, A-59, A-60, A-65, A-66, A-67, A-68, and A-70.
Compounds (from Table B): B-1.
Compounds (from Table C): C-1 and C-2.
Compounds (from Table D): D-1.

Example 3: Fungicidal Activity Against *Puccinia recondita* f. Sp. *Tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates are stored in darkness at 19° C. and 75% rh. The formulated test compound diluted in water is applied 1 day after inoculation. The leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (6-8 days after application).

The following compounds from Tables A to D gave at least 80% control of *Puccinia recondita* f. sp. *tritici* at 200 ppm when compared to untreated control under the same conditions, which showed extensive disease development:
Compounds (from Table A): A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-37, A-38, A-39, A-40, A-41, A-42, A-43, A-44, A-45, A-46, A-47, A-48, A-49, A-50, A-51, A-53, A-54, A-55, A-56, A-63, A-66, A-67, A-68, and A-70.
Compounds (from Table B): B-1, and B-3.
Compounds (from Table C): C-1, and C-2.
Compounds (from Table D): D-1.

Example 4: Fungicidal Activity Against *Puccinia recondita* f. Sp. *Tritici*/Wheat/Leaf Disc Preventative (Brown Rust)

Wheat leaf segments cv. Kanzler are placed on agar in multiwell plates (24-well format) and sprayed with the formulated test compound diluted in water. The leaf segments are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

The following compounds from Tables A to D gave at least 80% control of *Puccinia recondita* f. sp. *tritici* at 200 ppm when compared to untreated control under the same conditions, which showed extensive disease development:

Compounds (from Table A): A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-53, A-54, A-55, A-56, A-57, A-58, A-59, A-60, A-62, A-63, A-64, A-65, A-66, A-68, A-69, and A-70.
Compounds (from Table B): B-1, B-2, and B-3.
Compounds (from Table C): C-1 and C-2.
Compounds (from Table D): D-1.

Example 5: Fungicidal Activity Against *Uromyces viciae-Fabae*/Field Bean/Leaf Disc Preventative (*Faba*-Bean Rust)

Field bean leaf discs are placed on water agar in multiwell plates (96-well format) and 10 µl of the formulated test compound diluted in acetone and a spreader pipetted onto the leaf disc. Two hours after application leaf discs are inoculated by spraying a spore suspension on the lower leaf surface. The leaf discs are incubated in a climate cabinet at 22° C. with 18 hour day and 70% relative humidity. The activity of a compound is assessed as percent disease control compared to untreated when an appropriate level of disease damage appears in untreated check leaf disks (12 days after application).

The following compounds from Tables A to D gave at least 80% control of *Uromyces viciae-fabae* at 200 ppm when compared to untreated control under the same conditions, which showed extensive disease development:

Compounds (from Table A): A-1, A-2, and A-3.
Compounds (from Table B): B-1.
Compounds (from Table C): C-1 and C-2.
Compounds (from Table D): D-1.

The invention claimed is:
1. A compound of formula (I):

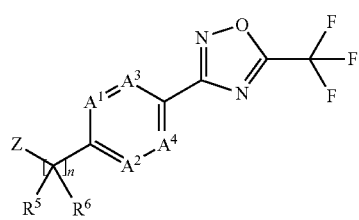

(I)

wherein
n is 1;
$A^1$ represents N or $CR^1$, wherein $R^1$ represents hydrogen, halogen, methyl, ethyl, difluoromethyl, trifluoromethyl, methoxy, ethoxy, or difluoromethoxy;

$A^2$ represents N or $CR^2$, wherein $R^2$ represents hydrogen, halogen, methyl, ethyl, difluoromethyl, trifluoromethyl, methoxy, ethoxy, or difluoromethoxy;

$A^3$ represents N or $CR^3$, wherein $R^3$ represents hydrogen or halogen;

$A^4$ represents N or $CR^4$, wherein $R^4$ represents hydrogen or halogen; and wherein no more than two of $A^1$ to $A^4$ are N;

$R^5$ and $R^6$ independently represent hydrogen, halogen, cyano, difluoromethyl, trifluoromethyl, or $C_{1-4}$alkyl, or together with the carbon atom to which they are bonded represent cyclopropyl;

Z represents a group selected from Z-1, Z-2, or Z-3:

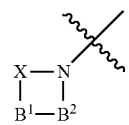

(Z-1)

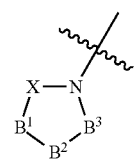

(Z-2)

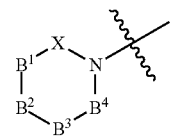

(Z-3)

wherein:
X represents C(O) or $S(O)_2$; and
(i) $B^1$ and $B^2$ in Z-1 represent $C(R^7)(R^8)$; or
(ii) $B^1$, $B^2$ and $B^3$ in Z-2 independently represent $C(R^7)(R^8)$, O, S, $NR^9$ or C(=O), wherein only one of $B^1$, $B^2$ and $B^3$ may be a group selected from O, S, $NR^9$ or C(=O); or
(iii) $B^1$, $B^2$, $B^3$ and $B^4$ in Z-3 independently represent $C(R^7)(R^8)$, O, S, $NR^9$ or C(=O), wherein only one of $B^1$, $B^2$, $B^3$ and $B^4$ may be a group selected from O, S or C(=O), and only one of $B^1$, $B^2$, $B^3$ and $B^4$ may be $NR^9$; or
(iv) $B^1$ in Z-2 is $C(R^7)(R^8)$ and $B^2$-$B^3$ is a group selected from $NR^9C(=O)$, C(=O)$NR^9$, N=N, $C(R^7)$=$C(R^8)$, $C(R^8)$=N or N=$C(R^8)$; or $B^3$ in Z-2 is $C(R^7)(R^8)$ and $B^1$-$B^2$ is a group selected from $NR^9C(=O)$, C(=O)$NR^9$, N=N, $C(R^7)$=$C(R^8)$, $C(R^8)$=N or N=$C(R^8)$; or
(v) $B^1$ and $B^2$ in Z-3 are $C(R^7)(R^8)$ and $B^3$-$B^4$ is a group selected from $NR^9C(=O)$, C(=O)$NR^9$, N=N, $C(R^7)$=$C(R^8)$, $C(R^8)$=N or N=$C(R^8)$; $B^1$ and $B^4$ in Z-3 are $C(R^7)(R^8)$ and $B^2$-$B^3$ is a group selected from $NR^9C(=O)$, C(=O)$NR^9$, N=N, $C(R^7)$=$C(R^8)$, $C(R^8)$=N or N=$C(R^8)$; or $B^3$ and $B^4$ in Z-3 are $C(R^7)(R^8)$ and $B^1$-$B^2$ is a group selected from $NR^9C(=O)$, C(=O)$NR^9$, N=N, $C(R^7)$=$C(R^8)$, $C(R^8)$=N or N=$C(R^8)$; or Z represents a group selected from Z-5, wherein Z-5 represents Z-5a, Z-5b, Z-5c, Z-5d, Z-5e, Z-5f or Z-5g:

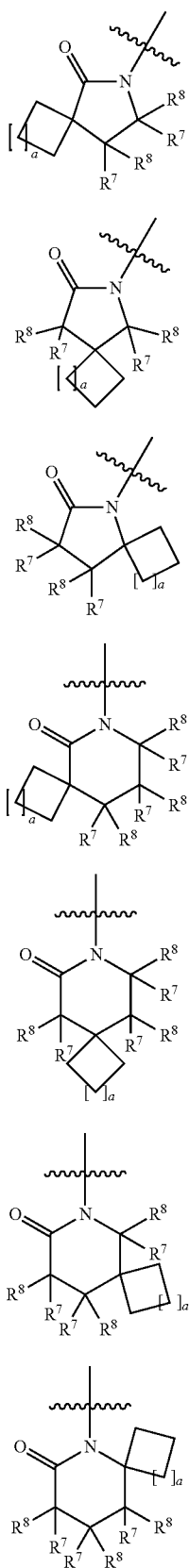

(Z-5a)

(Z-5b)

(Z-5c)

(Z-5d)

(Z-5e)

(Z-5f)

(Z-5g)

wherein a is 0, 1, 2 or 3; or

Z represents a group selected from Z-6, wherein Z-6 represents Z-6a, Z-6b, Z-6c or Z-6d:

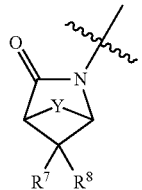

(Z-6a)

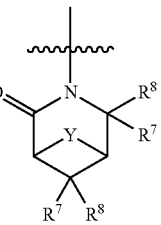

(Z-6b)

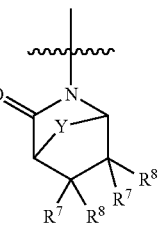

(Z-6c)

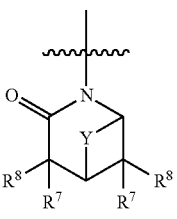

(Z-6d)

wherein Y is $C_{1-4}$alkylene or $C(R^7)=C(R^8)$;

$R^7$ and $R^8$ independently represent hydrogen, halogen, $C_1$-$C_4$alkyl, $C_1$-$C_4$haloalkyl or $C_1$-$C_4$alkoxy;

$R^9$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^{10}$, $C(O)OR^{10}$, $C(O)N(R^{10})R^{11}$, $S(O)_2R^{10}$ or $S(O)_2N(R^{10})R^{11}$, wherein $C_{1-6}$alkyl, $C_{3-6}$alkenyl, $C_{3-6}$, $C_{3-6}$cycloalkyl and $C_{1-6}$alkoxy are optionally substituted by halogen or cyano;

$R^{10}$ represents hydrogen, $C_{1-6}$alkyl, $C_{3-6}$cycloalkyl, $C_{3-6}$cycloalkyl$C_{1-2}$alkyl, $C_{1-4}$alkoxy$C_{1-4}$alkyl, wherein $C_{1-6}$alkyl, $C_{3-6}$cycloalkyl, $C_{3-6}$cycloalkyl$C_{1-2}$alkyl and $C_{1-4}$alkoxy$C_{1-4}$alkyl are optionally substituted by halogen or cyano; and $R^{11}$ represents hydrogen, $C_{1-4}$alkyl, $C_{1-4}$haloalkyl, $C_{1-4}$alkoxy or $C_{1-4}$alkoxy$C_{1-4}$alkyl; or a salt or an N-oxide thereof.

2. A compound according to claim 1, wherein:
(i) $A^1$ is $CR^1$ and $R^1$ is hydrogen, and $A^2$ is $CR^2$ and $R^2$ is hydrogen;
(ii) $A^1$ is $CR^1$ and $R^1$ is halogen, and $A^2$ is $CR^2$ and $R^2$ is hydrogen; or
(iii) $A^1$ is N and $A^2$ is $CR^2$ and $R^2$ is hydrogen.

3. A compound according to claim 1, wherein $A^1$ to $A^4$ are C—H.

4. A compound according to claim 1, wherein $R^5$ and $R^6$ are hydrogen, or $R^5$ is hydrogen and $R^6$ is methyl, or $R^5$ and $R^6$ are methyl.

5. A compound according to claim 1, wherein Z is:

Z-1 wherein $B^1$ and $B^2$ represent $C(R^7)(R^8)$;

Z-2 wherein $B^1$, $B^2$ and $B^3$ independently represent $C(R^7)(R^8)$, O, $NR^9$ or $C(=O)$, wherein only one of $B^1$, $B^2$ and $B^3$ may be O, $NR^9$ or $C(=O)$;

Z-3 wherein $B^1$, $B^2$, $B^3$ and $B^4$ independently represent $C(R^7)(R^8)$, O, $NR^9$ or $C(=O)$, wherein only one of $B^1$, $B^2$, $B^3$ and $B^4$ may be O, $NR^9$ or $C(=O)$;

Z-6a wherein Y represents $C(R^7)=C(R^8)$; or

Z-6c wherein Y represents $C_{2-4}$alkylene.

6. A compound according to claim 5, wherein Z is:

Z-2 wherein $B^1$ and $B^3$ independently represent $C(R^7)(R^8)$, O, $NR^9$ or $C(=O)$, wherein only one of $B^1$ and $B^3$ may be a O, $NR^9$ or $C(=O)$, and $B^2$ represents $C(R^7)(R^8)$;

Z-3 wherein $B^1$, $B^2$ and $B^4$ independently represent $C(R^7)(R^8)$, O, $NR^9$ or $C(=O)$, wherein only one of $B^1$, $B^2$ and $B^4$ may be a O, $NR^9$ or $C(=O)$, and $B^3$ represents $C(R^7)(R^8)$.

7. A compound according to claim 6, wherein Z is:

Z-2 wherein $B^1$ and $B^3$ independently represent $C(R^7)(R^8)$, O or $C(=O)$ wherein only one of $B^1$ and $B^3$ may be O or $C(=O)$, and $B^2$ represents $C(R^7)(R^8)$, wherein $R^7$ and $R^8$, independently of each other, are selected from hydrogen or $C_{1-4}$alkyl; or Z-3 wherein $B^1$, $B^2$ and $B^4$ independently represent $C(R^7)(R^8)$, O, $NR^9$ or $C(=O)$ wherein only one of $B^1$, $B^2$ and $B^4$ may be a O, $NR^9$ or $C(=O)$, and $B^3$ represents $C(R^7)(R^8)$, wherein $R^7$ and $R^8$, independently of each other, are selected from hydrogen or $C_{1-4}$alkyl.

8. A compound according to claim 1, wherein $R^7$ and $R^8$ independently represent hydrogen, methyl, difluoromethyl, trifluoromethyl or methoxy.

9. A compound according to claim 1, wherein $R^7$ and $R^8$ independently represent hydrogen or methyl.

10. A compound according to claim 1, wherein X is C(O).

11. An agrochemical composition comprising a fungicidally effective amount of a compound of formula (I) according to claim 1.

12. The composition according to claim 11, further comprising at least one additional active ingredient and/or an agrochemically-acceptable diluent or carrier.

13. A method of controlling or preventing infestation of useful plants by phytopathogenic microorganisms, wherein a fungicidally effective amount of a compound of formula (I) according to claim 1, or a composition comprising the compound of formula (I) as active ingredient, is applied to the plants, to parts thereof or the locus thereof.

14. The compound of claim 1, wherein the compound of formula (I) is selected from

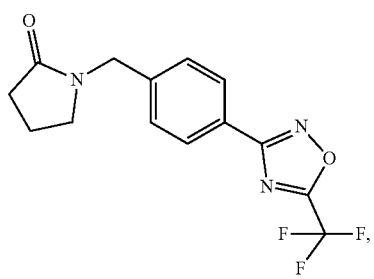

-continued

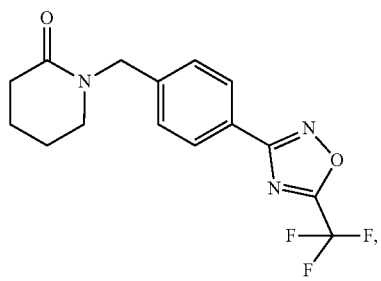

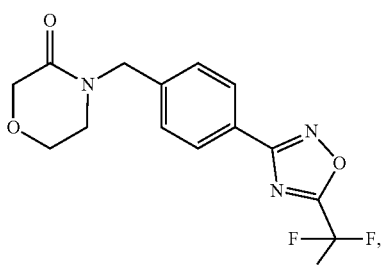

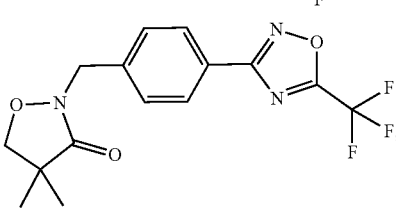

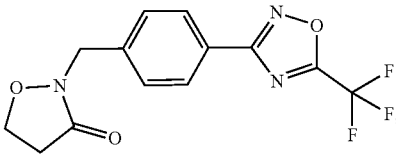

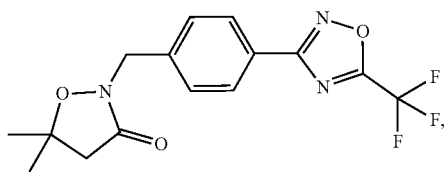

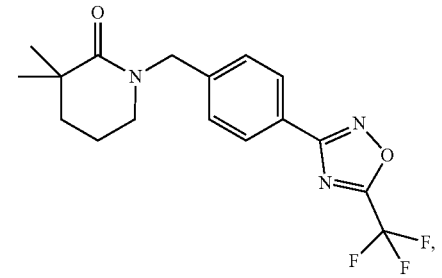

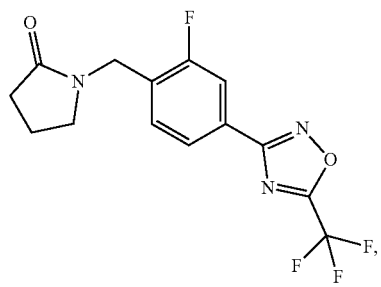

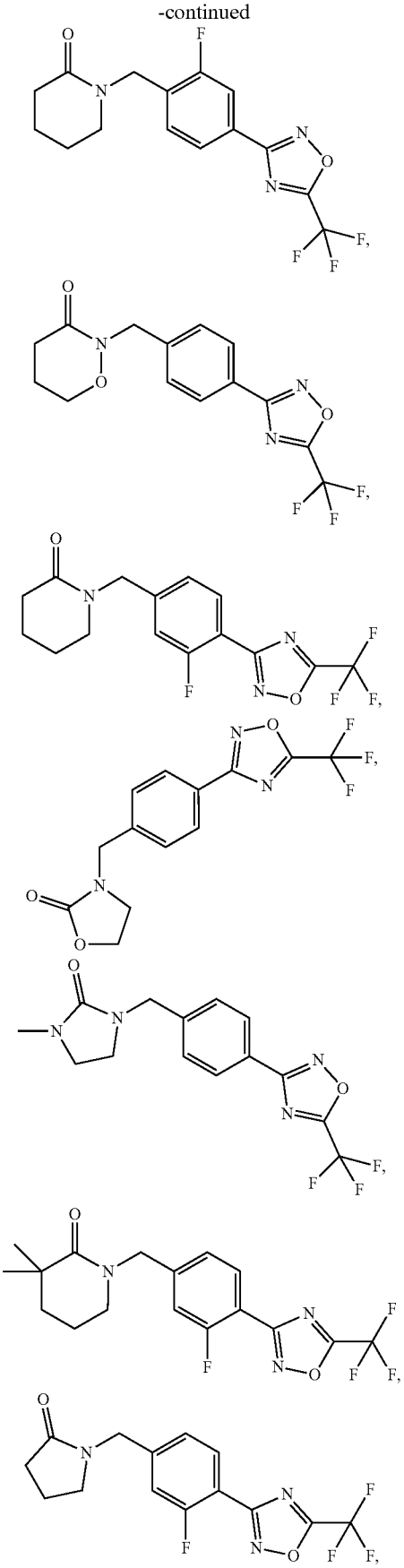
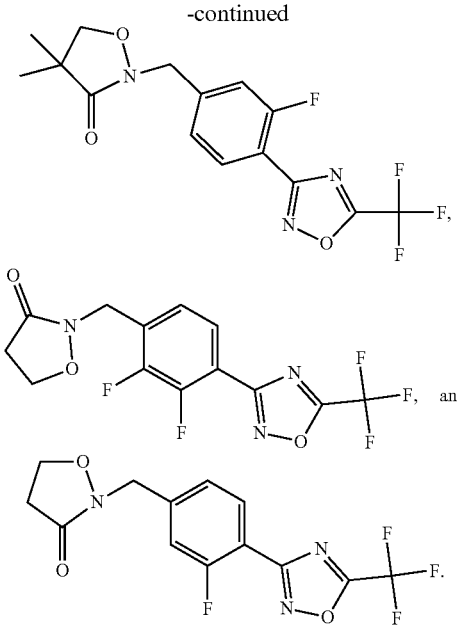

15. A compound of formula (I):

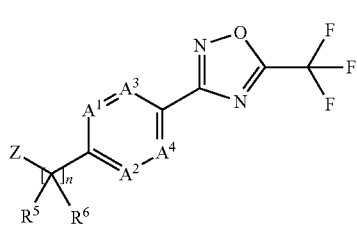

(I)

wherein
n is 0 or 1 or 2;
A$^1$ represents N or CR$^1$, wherein R$^1$ represents hydrogen, halogen, methyl, ethyl, difluoromethyl, trifluoromethyl, methoxy, ethoxy, or difluoromethoxy;
A$^2$ represents N or CR$^2$, wherein R$^2$ represents hydrogen, halogen, methyl, ethyl, difluoromethyl, trifluoromethyl, methoxy, ethoxy, or difluoromethoxy;
A$^3$ represents N or CR$^3$, wherein R$^3$ represents hydrogen or halogen;
A$^4$ represents N or CR$^4$, wherein R$^4$ represents hydrogen or halogen; and
wherein no more than two of A$^1$ to A$^4$ are N;
R$^5$ and R$^6$ independently represent hydrogen, halogen, cyano, difluoromethyl, trifluoromethyl, or C$_{1-4}$alkyl, or together with the carbon atom to which they are bonded represent cyclopropyl;
Z is Z-4:

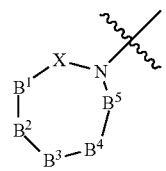

(Z-4)

wherein:
X represents C(O) or S(O)$_2$;
$B^1$, $B^2$, $B^3$, $B^4$ and B5 in Z-4 independently represent C($R^7$)($R^8$), O, S, N$R^9$ or C(=O), wherein only one of $B^1$, $B^2$, $B^3$, $B^4$ and $B^5$ may be a group selected from O, S, N$R^9$ or C(=O); or
$R^7$ and $R^8$ independently represent hydrogen, halogen, $C_1$-$C_4$alkyl, $C_1$-$C_4$haloalkyl or $C_1$-$C_4$alkoxy;
$R^9$ represents hydrogen, $C_{1-6}$alkyl, $C_{3-6}$alkenyl, $C_{3-4}$alkynyl, $C_{3-6}$cycloalkyl, $C_{1-6}$alkoxy, C(O)$R^{10}$, C(O)O$R^{10}$, C(O)N($R^{10}$)$R^{11}$, S(O)$_2$$R^{10}$ or S(O)$_2$N($R^{10}$)$R^{11}$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano;
$R^{10}$ represents hydrogen, $C_{1-6}$alkyl, $C_{3-6}$cycloalkyl, $C_{3-6}$cycloalkyl$C_{1-2}$alkyl, $C_{1-4}$alkoxy$C_{1-4}$alkyl, wherein $C_{1-6}$alkyl, $C_{3-6}$cycloalkyl, $C_{3-6}$cycloalkyl$C_{1-2}$alkyl and $C_{1-4}$alkoxy$C_{1-4}$alkyl are optionally substituted by halogen or cyano; and
$R^{11}$ represents hydrogen, $C_{1-4}$alkyl, $C_{1-4}$haloalkyl, $C_{1-4}$alkoxy or $C_{1-4}$alkoxy$C_{1-4}$alkyl; or
a salt or an N-oxide thereof.

16. The compound of claim 15, wherein the compound of formula (I) is

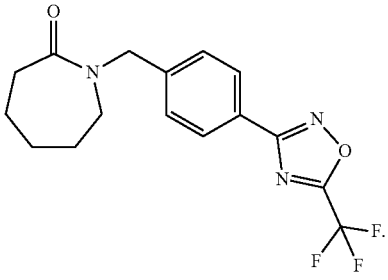 [SMILES: O=C1CCCCCN1Cc1ccc(-c2noc(C(F)(F)F)n2)cc1]

17. A compound of formula (I):

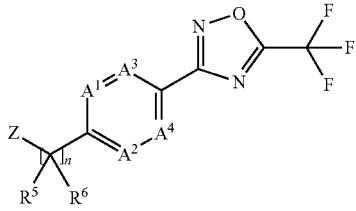

(I)

wherein
n is 0;
$A^1$ represents N or C$R^1$, wherein $R^1$ represents hydrogen, halogen, methyl, ethyl, difluoromethyl, trifluoromethyl, methoxy, ethoxy, or difluoromethoxy;
$A^2$ represents N or C$R^2$, wherein $R^2$ represents hydrogen, halogen, methyl, ethyl, difluoromethyl, trifluoromethyl, methoxy, ethoxy, or difluoromethoxy;
$A^3$ represents N or C$R^3$, wherein $R^3$ represents hydrogen or halogen;
$A^4$ represents N or C$R^4$, wherein $R^4$ represents hydrogen or halogen; and
wherein no more than two of $A^1$ to $A^4$ are N;
$R^5$ and $R^6$ independently represent hydrogen, halogen, cyano, difluoromethyl, trifluoromethyl, or $C_{1-4}$alkyl, or together with the carbon atom to which they are bonded represent cyclopropyl;

Z represents a group selected from Z-1, Z-2, or Z-3:

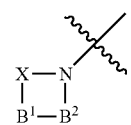
(Z-1)

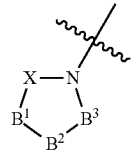
(Z-2)

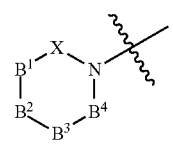
(Z-3)

wherein:
(i) X in Z-1 represents C(O) or S(O)$_2$, $B^1$ and $B^2$ in Z-1 represent C($R^7$)($R^8$); or
(ii) X in Z-2 represents S(O)$_2$, $B^1$, $B^2$ and $B^3$ in Z-2 independently represent C($R^7$)($R^8$), O, S, N$R^9$ or C(=O), wherein only one of $B^1$, $B^2$ and $B^3$ may be a group selected from O, S, N$R^9$ or C(=O); or
(iii) X in Z-2 represents C(O), $B^1$ in Z-2 represents S, N$R^9$ or C(=O), wherein $R^9$ represents hydrogen, $C_{3-6}$alkenyl, $C_{3-6}$alkynyl, $C_{1-6}$alkoxy, C(O)$R^{10}$, C(O)O$R^{10}$, C(O)N($R^{10}$)$R^{11}$, S(O)$_2$$R^{10}$ or S(O)$_2$N($R^{10}$)$R^{11}$, wherein $C_{3-6}$alkenyl, $C_{3-6}$alkynyl and $C_{1-6}$alkoxy are optionally substituted by halogen or cyano, and $B^2$ and $B^3$ in Z-2 are C($R^7$)($R^8$); or
(iv) X in Z-2 represents C(O), $B^1$ and $B^2$ in Z-2 represent C($R^7$)($R^8$), and $B^3$ in Z-2 is a group selected from O, S, N$R^9$ or C(=O); or
(v) X in Z-3 represents S(O)$_2$, $B^1$, $B^2$, $B^3$ and $B^4$ in Z-3 independently represent C($R^7$)($R^8$), O, S, N$R^9$ or C(=O), wherein only one of $B^1$, $B^2$, $B^3$ and $B^4$ may be a group selected from O, S or C(=O), and only one of $B^1$, $B^2$, $B^3$ and $B^4$ may be N$R^9$; or
(vi) X in Z-3 represents C(O), $B^1$ in Z-3 represents S, N$R^9$ or C(=O), wherein $R^9$ represents hydrogen, $C_{3-6}$alkenyl, $C_{3-6}$alkynyl, $C_{1-6}$alkoxy, C(O)$R^{10}$, C(O)O$R^{10}$, C(O)N($R^{10}$)$R^{11}$, S(O)$_2$$R^{10}$ or S(O)$_2$N($R^{10}$)$R^{11}$, wherein $C_{3-6}$alkenyl, $C_{3-6}$alkynyl and $C_{1-6}$alkoxy are optionally substituted by halogen or cyano, and $B^2$, $B^3$ and $B^4$ in Z-3 are C($R^7$)($R^8$); or
(vii) X in Z-3 represents C(O), and $B^1$, $B^2$, and $B^3$ in Z-3 represent C($R^7$)($R^8$), and $B^4$ in Z-3 is a group selected from O, S, N$R^9$ or C(=O); or
(viii) 1X in Z-2 represents C(O) or S(O)$_2$, $B^1$ in Z-2 is C($R^7$)($R^8$) and $B^2$-$B^3$ is a group selected from N$R^9$C(=O), C(=O)N$R^9$, N=N, C($R^7$)=C($R^8$), C($R^8$)=N or N=C($R^8$); or $B^3$ in Z-2 is C($R^7$)($R^8$) and $B^1$-$B^2$ is a group selected from N$R^9$C(=O), C(=O)N$R^9$, N=N, C($R^7$)=C($R^8$), C($R^8$)=N or N=C($R^8$); or
(ix) X in Z-3 represents C(O) or S(O)$_2$, $B^1$ and $B^2$ in Z-3 are C($R^7$)($R^8$) and $B^3$-$B^4$ is a group selected from N$R^9$C(=O), C(=O)N$R^9$, N=N, C($R^7$)=C($R^8$), C($R^8$)=N or N=C($R^8$); $B^1$ and $B^4$ in Z-3 are C($R^7$)($R^8$) and $B^2$-$B^3$ is a group selected from N$R^9$C(=O), C(=O)N$R^9$, N=N, C($R^7$)=C($R^8$), C($R^8$)=N or N=C(R⁸); or B³ and B⁴ in Z-3 are C(R⁷)(R⁸) and B¹-B² is a group selected from NR⁹C(=O), C(=O)NR⁹, N=N, C(R⁷)=C(R⁸), C(R⁸)=N or N=C(R⁸); or Z represents a group selected from Z-5, wherein Z-5 represents Z-5a, Z-5b, Z-5c, Z-5d, Z-5e, Z-5f or Z-5g:

(Z-5a)
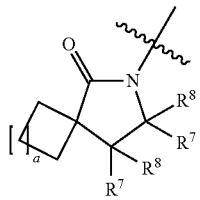

(Z-5b)
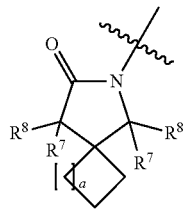

(Z-5c)
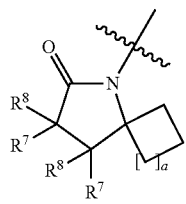

(Z-5d)
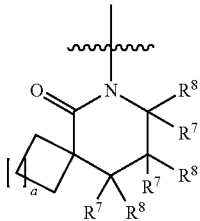

(Z-5e)
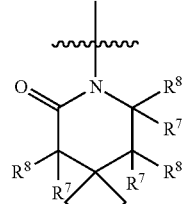

(Z-5f)
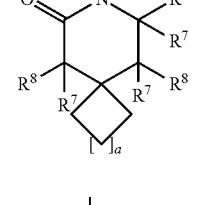

(Z-5g)
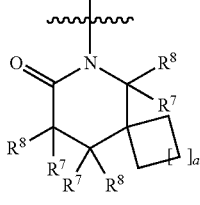

wherein a is 0, 1, 2 or 3; or

Z represents a group selected from Z-6, wherein Z-6 represents Z-6a, Z-6b, Z-6c or Z-6d:

(Z-6a)
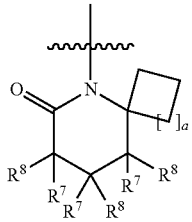

(Z-6b)
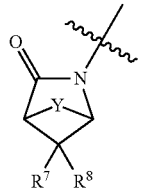

(Z-6c)
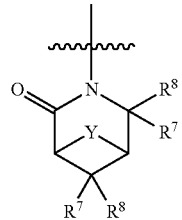

(Z-6d)
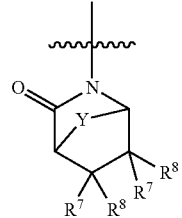

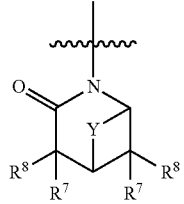

wherein Y is C₁₋₄alkylene or C(R⁷)=C(R⁸);
R⁷ and R⁸ independently represent hydrogen, halogen, C₁-C₄alkyl, C₁-C₄haloalkyl or C₁-C₄alkoxy;
R⁹ represents hydrogen, C₁₋₆alkyl, C₃₋₆alkenyl, C₃₋₆alkynyl, C₃₋₆cycloalkyl, C₁₋₆alkoxy, C(O)R¹⁰, C(O)OR¹⁰, C(O)N(R¹⁰)R¹¹, S(O)₂R¹⁰ or S(O)₂N(R¹⁰)R¹¹, wherein C₁₋₆alkyl, C₃₋₆alkenyl, C₃₋₆alkynyl, C₃₋₆cycloalkyl and C₁₋₆alkoxy are optionally substituted by halogen or cyano;
R¹⁰ represents hydrogen, C₁₋₆alkyl, C₃₋₆cycloalkyl, C₃₋₆cycloalkylC₁₋₂alkyl, C₁₋₄ alkoxyC₁₋₄alkyl, wherein C₁₋₆alkyl, C₃₋₆cycloalkyl, C₃₋₆cycloalkylC₁₋₂alkyl and C₁₋₄alkoxyC₁₋₄alkyl are optionally substituted by halogen or cyano; and R$^{11}$ represents hydrogen, C$_{1-4}$alkyl, C$_{1-4}$haloalkyl, C$_{1-4}$alkoxy or C$_{1-4}$alkoxyC$_{1-4}$alkyl; or
a salt or an N-oxide thereof.

18. A compound of formula (I):

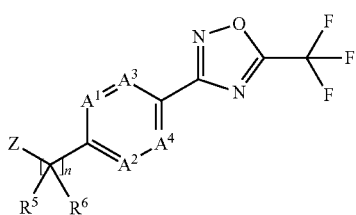

(I)

wherein
n is 2;
A$^1$ represents N or CR$^1$, wherein R$^1$ represents hydrogen, halogen, methyl, ethyl, difluoromethyl, trifluoromethyl, methoxy, ethoxy, or difluoromethoxy;
A$^2$ represents N or CR$^2$, wherein R$^2$ represents hydrogen, halogen, methyl, ethyl, difluoromethyl, trifluoromethyl, methoxy, ethoxy, or difluoromethoxy;
A$^3$ represents N or CR$^3$, wherein R$^3$ represents hydrogen or halogen;
A$^4$ represents N or CR$^4$, wherein R$^4$ represents hydrogen or halogen; and
wherein no more than two of A$^1$ to A$^4$ are N;
R$^5$ and R$^6$ independently represent hydrogen, halogen, cyano, difluoromethyl, trifluoromethyl, or C$_{1-4}$alkyl, or together with the carbon atom to which they are bonded represent cyclopropyl;
Z represents a group selected from Z-1, Z-2, or Z-3:

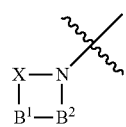

(Z-1)

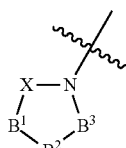

(Z-2)

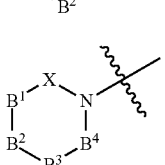

(Z-3)

wherein:
X represents C(O) or S(O)$_2$; and
(i) B$^1$ and B$^2$ in Z-1 represent C(R$^7$)(R$^8$); or
(ii) B$^1$, B$^2$ and B$^3$ in Z-2 independently represent C(R$^7$)(R$^8$), O, S, NR$^9$ or C(=O), wherein only one of B$^1$, B$^2$ and B$^3$ may be a group selected from O, S, NR$^9$ or C(=O); or
(iii) B$^1$, B$^2$, B$^3$ and B$^4$ in Z-3 independently represent C(R$^7$)(R$^8$), O, S, NR$^9$ or C(=O), wherein only one of B$^1$, B$^2$, B$^3$ and B$^4$ may be a group selected from O, S or C(=O), and only one of B$^1$, B$^2$, B$^3$ and B$^4$ may be NR$^9$; or (iv) B$^1$ in Z-2 is C(R$^7$)(R$^8$) and B$^2$-B$^3$ is a group selected from NR$^9$C(=O), C(=O)NR$^9$, N=N, C(R$^7$)=C(R$^8$), C(R$^8$)=N or N=C(R$^8$); or B$^3$ in Z-2 is C(R$^7$)(R$^8$) and B$^1$-B$^2$ is a group selected from NR$^9$C(=O), C(=O)NR$^9$, N=N, C(R$^7$)=C(R$^8$), C(R$^8$)=N or N=C(R$^8$); or (v) B$^1$ and B$^2$ in Z-3 are C(R$^7$)(R$^8$) and B$^3$-B$^4$ is a group selected from NR$^9$C(=O), C(=O)NR$^9$, N=N, C(R$^7$)=C(R$^8$), C(R$^8$)=N or N=C(R$^8$); B$^1$ and B$^4$ in Z-3 are C(R$^7$)(R$^8$) and B$^2$-B$^3$ is a group selected from NR$^9$C(=O), C(=O)NR$^9$, N=N, C(R$^7$)=C(R$^8$), C(R$^8$)=N or N=C(R$^8$); or B$^3$ and B$^4$ in Z-3 are C(R$^7$)(R$^8$) and B$^1$-B$^2$ is a group selected from NR$^9$C(=O), C(=O)NR$^9$, N=N, C(R$^7$)=C(R$^8$), C(R$^8$)=N or N=C(R$^8$); or Z represents a group selected from Z-5, wherein Z-5 represents Z-5a, Z-5b, Z-5c, Z-5d, Z-5e, Z-5f or Z-5g:

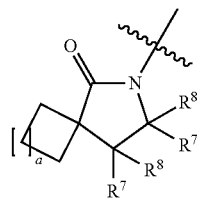

(Z-5a)

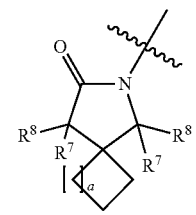

(Z-5b)

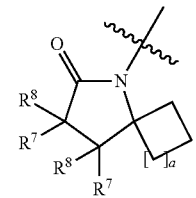

(Z-5c)

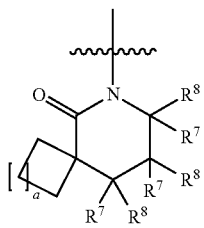

(Z-5d)

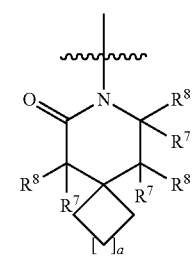

(Z-5e)

(Z-5f)

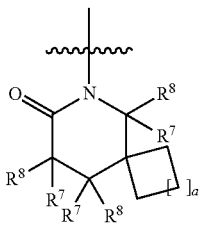

(Z-5g)

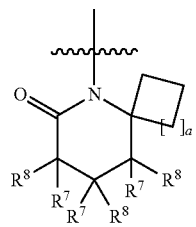

wherein a is 0, 1, 2 or 3; or

Z represents a group selected from Z-6, wherein Z-6 represents Z-6a, Z-6b, Z-6c or Z-6d:

(Z-6a)

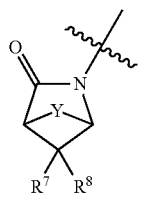

(Z-6b)

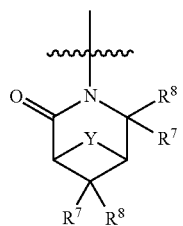

(Z-6c)

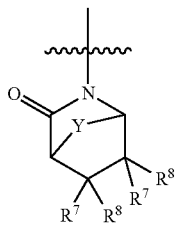

(Z-6d)

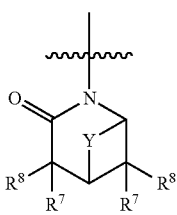

wherein Y is $C_{1-4}$alkylene or $C(R^7)=C(R^8)$;

$R^7$ and $R^8$ independently represent hydrogen, halogen, $C_1$-$C_4$alkyl, $C_1$-$C_4$haloalkyl or $C_1$-$C_4$alkoxy;

$R^9$ represents hydrogen, $C_{1-6}$alkyl, $C_{3-6}$alkenyl, $C_{3-6}$alkynyl, $C_{3-6}$cycloalkyl, $C_{1-6}$alkoxy, $C(O)R^{10}$, $C(O)OR^{10}$, $C(O)N(R^{10})R^{11}$, $S(O)_2R^{10}$ or $S(O)_2N(R^{10})R^{11}$, wherein $C_{1-6}$alkyl, $C_{3-6}$alkenyl, $C_{3-6}$alkynyl, $C_{3-6}$cycloalkyl and $C_{1-6}$alkoxy are optionally substituted by halogen or cyano;

$R^{10}$ represents hydrogen, $C_{1-6}$alkyl, $C_{3-6}$cycloalkyl, $C_{3-6}$cycloalkyl$C_{1-2}$alkyl, $C_{1-4}$ alkoxy$C_{1-4}$alkyl, wherein $C_{1-6}$alkyl, $C_{3-6}$cycloalkyl, $C_{3-6}$cycloalkyl$C_{1-2}$alkyl and $C_{1-4}$alkoxy$C_{1-4}$alkyl are optionally substituted by halogen or cyano; and $R^{11}$ represents hydrogen, $C_{1-4}$alkyl, $C_{1-4}$haloalkyl, $C_{1-4}$alkoxy or $C_{1-4}$alkoxy$C_{1-4}$alkyl; or a salt or an N-oxide thereof.

* * * * *

UNITED STATES PATENT AND TRADEMARK OFFICE
CERTIFICATE OF CORRECTION

PATENT NO. : 10,640,497 B2
APPLICATION NO. : 15/780007
DATED : May 5, 2020
INVENTOR(S) : Thomas James Hoffman et al.

It is certified that error appears in the above-identified patent and that said Letters Patent is hereby corrected as shown below:

In the Claims

In Claim 15 at Column 107, Line 3, 'B5' should read --$B^5$--.

In Claim 15 at Column 107, Lines 9-10, '$C_{3-4}$alkynyl' should read --$C_{3-6}$alkynyl--.

In Claim 17 at Column 108, Line 56, '1X' should read --X--.

Signed and Sealed this
Seventeenth Day of November, 2020

Andrei Iancu
*Director of the United States Patent and Trademark Office*